US 7,572,589 B2

(12) United States Patent
Reiner et al.

(10) Patent No.: US 7,572,589 B2
(45) Date of Patent: Aug. 11, 2009

(54) DIAGNOSIS AND TREATMENT OF INFECTIOUS DISEASES THROUGH INDEL-DIFFERENTIATED PROTEINS

(75) Inventors: Neil E. Reiner, Vancouver (CA); Artem Tcherkassov, Vancouver (CA); Devki Nandan, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 305 days.

(21) Appl. No.: 10/494,175

(22) PCT Filed: Nov. 1, 2002

(86) PCT No.: PCT/CA02/01689

§ 371 (c)(1),
(2), (4) Date: Oct. 28, 2004

(87) PCT Pub. No.: WO03/037926

PCT Pub. Date: May 8, 2003

(65) Prior Publication Data

US 2005/0095247 A1    May 5, 2005

Related U.S. Application Data

(60) Provisional application No. 60/349,371, filed on Jan. 22, 2002, provisional application No. 60/349,339, filed on Jan. 22, 2002, provisional application No. 60/393,385, filed on Jul. 5, 2002.

(30) Foreign Application Priority Data

Nov. 1, 2001   (CA)   .................................... 2360987

(51) Int. Cl.
*G01N 33/53* (2006.01)
*A61K 39/395* (2006.01)
*C07K 17/00* (2006.01)

(52) U.S. Cl. .................. 435/7.1; 424/145.1; 424/146.1; 530/388.6; 530/391.1

(58) Field of Classification Search ................ 435/69.1, 435/69.7, 7.1, 7.2; 424/146.1; 530/300, 530/350, 388.26, 391.1
See application file for complete search history.

(56) References Cited

U.S. PATENT DOCUMENTS 6,018,102 A    1/2000   Garbarino et al.

(Continued)

FOREIGN PATENT DOCUMENTS

JP    11318460 A   * 11/1999

(Continued)

OTHER PUBLICATIONS

Roitt et al, 1998, Immunology, 4th ed, Mosby, London p. 7.7-7.8.*

(Continued)

*Primary Examiner*—Robert B Mondesi
*Assistant Examiner*—Padma V Baskar
(74) *Attorney, Agent, or Firm*—Carol L. Francis; Bozicevic, Field & Francis LLP

(57) ABSTRACT

A compound capable of specifically binding to pathogen EF-1α but not host EF-1α, wherein the compound binds to any part of an amino acid sequence having at least 70% sequence identity to amino acids 240-230 of SEQ ID NO:22.

21 Claims, 3 Drawing Sheets

A. Human EF-1α    B. Leishmania EF-1α

U.S. PATENT DOCUMENTS

| | | | |
|---|---|---|---|
| 6,107,316 | A | 8/2000 | Young et al. |
| 6,127,524 | A | 10/2000 | Casipit et al. |
| 6,168,928 | B1 | 1/2001 | Read et al. |
| 6,268,160 | B1 | 7/2001 | Clough et al. |
| 6,306,663 | B1 | 10/2001 | Kenten et al. |
| 6,358,692 | B1 * | 3/2002 | Jindal et al. .................. 435/7.1 |

FOREIGN PATENT DOCUMENTS

| | | |
|---|---|---|
| WO | WO 97/01578 | 1/1997 |

OTHER PUBLICATIONS

Greenspan et al., (Nature Biotechnology 7:936-937 (1999).*
Rey Ladino 1997 et al (Experimental Parasitology, vol. 85, No. 3, 1997, pp. 249-263, see IDS ).*
Rudinger et al, in "Peptide Hormones", edited by Parsons, J.A., University Park Press, Jun. 1976, ).*
Bowie et al (Science, 1990, 257:1306-1310).*
Holmes (Exp. Opin.Invest. Drugs, 2001, 10(3):511-519.*
Mulot et al Gene 174, 19-26, 1996.*
Gupta et al (Trends in Microbiology, vol. 14, Issue 12, Dec. 2006, pp. 527-535).*
Griffiths et al (Microbiology. 2005 , 151(Pt 8):2647-57).*
Gao et al (International journal of systematic and evolutionary microbiology, 2005, vol. 55 (6), pp. 2401-2412 ).*
Genesis: Evolution and Diversity of Life edited by Joseph Seckbach ; Bacterial phylogeny, Gupta, pp. 266-276.*
Lederman et al (Molecular Immunology 28:1171-1181, 1991).*
Li et al (Proc. Natl. Acad. Sci. USA 77:3211-3214, 1980).*
Aebischer, T., et al. Proteophosphoglycan, a major secreted product of intracellular *Leishmania mexicana* amastigotes, is a poor B-cell antigen and does not elicit a specific conventional CD4+T-cell response. Infect Immun (1999) 67(10):5379-5385.
Altschul, S.F., et al. Gapped BLAST and PSI-BLAST:a new generation of protein database search programs. Nucleic Acids Res. (1997) 25(17):3389-3402.
Andersen, G.R., et al. Crystal structures of nucleotide exchange intermediates in the eEF1A-eEF1Bα complex. Nat Struct Biol (2001) 8:531:534.
Aronov, A.M., et al. Rational design of selective submicromolar inhibitors of tritrichomonas foetus hypoxanthine-guanine-xanthine phosphoribosyltransferase. Biochemistry (2000) 39(16):4684-91.
Bairoch, A. and Apweiler R. The SWISS-PROT protein sequence database: its relevance to human molecular medical research. J Mol Med (1997) 75(5):312-316.
Bairoch, A. and Apweiler, R. The SWISS-PROT protein sequence database and its supplement TrEMBL in 2000. Nucleic Acid Res (2000) 28(1):45-48.
Baldauf, S.L., et al. Animals and fungi are each other's closest relatives: congruent evidence from multiple proteins. PNAS (1993) 90:11558-62.
Baldwin, G.C., et al. Human immunodeficiency virus causes mononuclear phagocyte dysfunction. Proc Natl Acad Sci USA (1990) 87:3933-3937.
Barral, A., et al. Transforming growth factor β as a virulence mechanism for *Leishmania braziliensis*. Proc Natl Acad Sci USA (1993) 90:3442-3446.
Basu, N., et al. Down-regulation of mannose receptors on macrophages after infection with *Leishmania donovani*. Biochem J (1991) 277 (Pt 2):451-456.
Beatty, W.L., et al. Identification of mycobacterial surface proteins released into subcellular compartments of infected macrophages. Infect Immun (2000) 68(12):6997-7002.
Berg, K.L, e t al. The major SHP-1-binding, tryosine-phosphorylated protein in macrophages is a memeber of the KIR/LIR family and an SHP-1 susbstrate. Oncogene (1998) 17:2535-2541.
Beverley, S.M. Hijacking the cell: parasites in the driver's seat. Cell (1996) 87(5):787-789.
Binstadt, B.A., et al. SLP-76 is a direct substrate of SHP-1 recruited to killer cell inhibitory receptors. J Biol Chem (1998) 273(42):27518-27523.

Blanchette, J., et al. Leishmania-induced increases in activation of macrophage SHP-1, tyrosine phosphatase are associated with impaired IFN-γ-triggered JAK2 activation. Eur J Immunol (1999) 29:3737-3744.
Blasioli, J., et al. Definition of the sites of interaction between the protein tyrosine phosphatase SHP-1 and CD22*. J Biol Chem (1999) 274(4):2303-2307.
Blery, M., et al. Early signaling via inhibitory and activating NK receptors. Hum Immunol (2000) 61:51-64.
Bliska, J.B., et al. Signal transduction in the mammalian cell during bacterial attachment and entry. Cell (1993) 73(5):903-920.
Bonafonte, M.T., et al. Isolation of the gene coding for elongation factor-1alpha in *Cryptosporidium parvum*. Biochim Biophys Acta (1997) 1351(3):256-60.
Borges, M.M., et al. Potent stimulation of the innate immune system by a *Leishmania brasiliensis* recombinant protein. Infect Immun (2001) 69(9):5270-7.
Bouchard, P., et al. Phosphorylation and Identification of a major tyrosine phosphorylation site in protein tyrosine phosphatase 1C*. J Biol Chem (1994) 269(30):19585-19589.
Bousquet, C., et al. sst2 somatostatin receptor mediates negative regulation of insulin receptor signaling through the tyrosine phosphatase SHP-1*. J Biol Chem (1998) 273(12):7099-7106.
Brummel, J.H., et al. Regulation of Src homology 2-containing tyrosine phosphatase 1 during activation of human neutrophils. J Biol Chem (1997) 272(2):875-882.
Button, L.L., et al. Recombinant *Leishmania* surface glycoprotein GP63 is secreted in the baculovirus expression system as a latent metalloproteinase. Gene (1993) 134(1):75-81.
Carrero, J.C., et al. Cloning and characterization of *Entamoeba histolytica* antigens recognized by human secretory IgA antibodies. Parisitol Res (2000) 86(4):330-4.
Chan, J., et al. Lipoarabinomannan, a possible virulence factor involved in persistence of Mycobacterium tuberculosis within macrophages. Infect Immun (1991) 59(5):1755-1761.
Chen, H.E. , et al. Regulation of colony-stimulating factor 1 receptor signaling by the SH2 domain-containing tyrosine phosphatase SHPTP1. Mol Cell Biol (1996) 16(7):3685-3697.
Ciechanover, A., et al. Ubiquitin-mediated proteolysis: biological regulation via destruction. Bioessays (2000) 22:442-451.
Clayton, C., et al. Protein trafficking in kinetoplastid protozoa. Microbiol Rev (1995) 59(3):325-344.
Clough, B., et al. Antibiotic inhibitors of organellar protein synthesis in *Plasmodium falciparum*. Protist (1999) 159(2):189-95.
Coggeshall, K.M. Negative signaling in health and disease. Immunol Res (1999) 19(1):47-64.
Cohen, G.B., et al. Modular binding domains in signal transduction proteins. Cell (1995) 80(2):237-248.
Colonna, M., et al. A novel family of Ig-like receptors of HLA class I molecules that modulate function of lymphoid and myeloid cells. J Leukoc Biol (1999) 66(3):375-381.
Condeelis, J. Elongation factor 1α, translation and the cytoskeleton. Trends Biochem Sci (1995) 20:169-170.
Damen, J.E., et al. Phosphorylation of tyrosine 503 in the erythropoietin receptor (EpR) is essential for binding the P85 subunit of phosphatidylinositol OPI) 3-kinase and for EpR-associated Pi 3-kinase activity. J Biol Chem (1995) 270:23402-23408.
Darnell, J.E., Jr., et al., Jak-STAT pathways and transcriptional activation in response to IFNs and other extracellular signaling proteins. Science (1994) 264(5164):1415-1421.
David, M., et al. Differential regulation of the alpha/beta interferon-stimulated Jak/Stat pathway by the SH2 domain-containing tyrosine phosphatase SHPTP1. Mol Cell Biol (1995) 15(12):7050-7058.
David, M., et al. The SH2 domain-containing tyrosine phosphatase PTP1D is required for interferon α/β gene expression. J Biol Chem (1996) 271(27):15862-15865.
Dell, K.R., et al. Stage-specific regulation of protein phosphorylation in *Leishmania* major. Mol Biochem Parasitol (1994) 64(2):283-292.
Denny, P.W., et al. Acylation-dependent protein export in *Leishmania*. J Biol Chem (2000) 275(15):11017-11025.
Descoteaux, A., et al. c-fos and tumor necrosis factor gene expression in *Leishmania donovani*-infected macrophages. Mol and Cell Biol (1989) 9(11):5223-5227.

Deshaies, R.J. SCF and Cullin/Ring H2-based ubiquitin ligases. Annual Review in Cellular Development Biology (1999) 15:435-467.

Dong, Q., et al. Negative regulation of myeloid cell proliferation and function by the SH2 domain-containing tyrosine phosphatase-1[1]. J Immunol (1999) 162:3220-3230.

Dustin, L.B., et al. Expression of dominant-negative Src-homology domain 2-containing protein tyrosine phosphatase-1 results in increased Syk tyrosine kinase activity and b cell activation J Immunol (1999) 162:2717-2724.

Eddy, S.R. Hidden markov models. Current Opinion in Structural Biology (1996) 6(3):361-365.

Edelsbrunner, H., et al. Measuring proteins and voids in proteins. in 28th International Conference on System Science. 1995. Hawaii, pp. 256-264.

Fantl, W.J., et al. Distinct phosphotyrosines on a growth factor receptor bind ot specfic molecules that mediate different signaling pathways. Cell (1992) 69(3):413-423.

Fastame, I.G., et al. Characterization of a novel translation inhibitor from *Leishmania mexican* promastigotes. Cell Mol Biol (1998) 4493):475-81.

Fearon, D.T., et al. The instructive role of innate immunity in the acquired immune response. Science (1996) 272(5258):50-54.

Feng, G.S. et al. Phosphotyrosine phosphatases with SH2 domains: regualtors of signal transduction. Trends Genet (1994) 10(2):54-58.

Feng, G.S., et al. SH2-containing phosphotyrosine phosphatase as a target of protein-tyrosine kinases. Science (1993) 259(5101):1607-1611.

Finbloom, D.S., et al. Regulation of the Jak/STAT signalling pathway. Cell Signal (1995) 7(8):739-745.

Finlay, B.B., et al. Exploitation of mammalian host cell functions by bacterial pathogens. Science (1997) 276(5313):718-725.

Forget, G., et al. Role of host phosphotyrosine phosphatase SHP-1 in the development of murine *Leishmaniasis*, Eur J Immunol (2001) 31(11):3185-96.

Forget, G., et al. Progression of *Leishmaniasis* in SHP-1 deficient mice. Journal of Leukocyte Biology Supplement, 1999 Meeting Abstracts 31:133.

Frank, C., et al. Binding of phosphatidic acid to the protein-tyrosine phosphatase SHP-1 as a basis for activity modulation. Biochemistry (1999) 38(37):11993-12002.

Frearson, J.A. and Alexander, D.R. The role of phosphotyrosine phosphatases in haematopoietic cell signal transduction. Bioessays (1997) 19(5):417-427.

Fruth, U., et al. *Leishmania* major interferes with antigen presentation by infected macrophages. J Immunol (1993) 150(5):1857-1864.

Ganatra, J.B., et al. Viral causes fo the acute retinal necrosis syndrome. Am J Ophthalmol (2000) 129:166-172.

Gradler, U., et al. A new target for *Shigellosis*: rational design and crystallographic studies of inhibitors of tRNA-guanine transglycosylase. Journal of Molecular Biology (2001) 306(3):455-67.

Guex, N. and Peitsch, M.C. Swiss-Model and the Swiss-PdbViewer:an environment for comparative protein modeling. Electrophoresis (1997) 18:2714-2723.

Haque, S.J., et al. Receptor-associated constitutive protein tyrosine phosphatase activity controls the kinase function of JAK1. Proc Natl Acad Sci USA (1997) 94:8563-8568.

Haque, S.J., et al. Protein-tyrosine phosphatase Shp1-1 is a negative regulator of IL-4- and IL-13-dependent signal transduction. J Biol Chem (1998) 273(51):33893-33896.

Hmama, Z., et al. Attenuation of HLA-DR expression by mononuclear phagocytes infected with Mycobacterium tuberculosis is related to intracellular sequestration of immature class II heterodimers. J Immunol (1998) 161:4882-4893

Hoedemaeker, F.J., et al. Crystal structure of the C-terminal sH2 domian of the P85α regulatory subunit of phosphoinositde 3-kinase: an SH2 domain mimicking its own substrate. J Mol Biol (1999) 292:763-770.

Horta, M.F. Pore-forming proteins in pathogenic protozoan parasites. Trends Microbiol (1997) 5(9):363-366.

Hunter, T. Protein kinases and phosphatases: the yin and yang of protein phosphorylation and signaling. Cell (1995) 80(2):225-236.

Ilg, T., et al. Characterization of phosphoglycan-containing secretory products of *Leishmania*. Parasitology (1994) 108 Suppl, S63-S71.

Imani, F., et al. Interleukin-4 (IL-4) induced phosphatidylinositol 3-kinase (p85) dephosphorylation. J Biol Chem (1997) 272(12):7927-7931.

Jiao, H., et al. Direct association with the dephosphorylation of Jak2 kinase by the Sh2-domain-containing protein tyrosine phosphatase SHP-1. Mol Cell Biol (1996) 16(12):6985-6992.

Jin, Y.J., et al. Human 70-kDa SHP-1L differs from 68-kDa SHP-1 in its C-terminal structure and catalytic activity. J Biol Chem (1999) 274(40):28301-28307.

Joiner, K.A. Perspectives series: host/pathogen interactions. J Clin Invest (1997) 99(8):1814-1817.

Jones, D.T. Protein secondary structure prediction based on position-specific scoring matrices. J Mol Biol (1999) 292(2):195-202.

Joshi, P.B., et al. The gene encoding streptothricin acetyltransferase (sat) as a selectable marker for *Leishmania* expression vectors. Gene (1995) 156(1):145-9.

Joshi, P.L., et al. Targeted gene deletion of *Leishmania* major genes encoding developmental stage-specific leishmanolysin (GP63). Mol Microbiol (1998) 27(3):519-530.

Junker, V.L., et al. Representation of functional information in the SWISS-PROT data bank. Bioinformatics (1999) 15(12): 1066-1007.

Kaur, K.J. and Ruben. Protein translation elongation factor-1α from *Trypanosoma brucei* binds Calmodulin. J Biol Chem (1994) 269:23045-23050.

Kaye, P.M., et al. Regulation of macrophage accessory cell activity by mycobacterial. II. In vitro inhibition of la expression by *Mycobacterium microti*. Clin Exp Immunol (1986) 64(1):28-34.

Kelly, J.M., et al. A shuttle vector which facilitates the expression of transfected genes in *Trypanosoma cruzi* and *Leishmania*. Nucleic Acids Research (1992) 20(15):3963-9.

Kharitonenkov, A., et al. A family of proteins that inhibit signalling through tyrosine kinase receptors. Nature (1997) 386(6621):181-186.

Kishimoto, A. et al. Studies on the phosphorylation of myelin basic protein by protein kinase C and adenosin 3':5'- monophosphate-dependent protein kinase. J Biol Chem (1985) 260:12492-12499.

Klingmuller, U., et al. Specific recruitment of sH-PTP1 to the erythropoietin receptor casues inactivation of JAK2 and termination of proliferative signals. Cell (1995) 80(5):729-738.

Knutson, K.L., et al. Lipoarabinomannan of mycobacterium tuberculosis promotes protein tyrosine dephosphorylation and inhibition of mitogen-activated protein kinase in human mononuclear phagocytes. J Biol Chem (1998) 273(1):645-652.

Kurogi, Y. and O.F. Guner. Pharmacophore modeling and three-dimensional database searching for drug design using catalyst. Curr Med Chem (2001) 8(9):1035-55.

Kwan, W.C., et al. Inhibition of expression of major histocompatibility complex class II molecules in macrophages infected with *Leishmania donovani* occurs at the level of gene transcription via a cyclic AM-independent mechanism. Infect Immun (1992) 60(5):2115-2120.

Laban, A. and Wirth, D.F. Transfection of *Leishmania enriettii* and expression of chloramphenicol acetyltransferase gene. PNAS (1989) 86(23):9119-23.

Ladeira de Campos, C.B., et al. *Leishmania braziliansis*, molecular characterization of elongation factor-1alpha gene. Gene (1997) 198(1-2):281-8.

LeBowitz, J.H., et al. Development of a stable *Leishmania* expression vector and application to the study of parasite surface antigen genes. PNAS (1990) 87(24)9736-40.

Lesnick, M.L., et al. The Salmonella spvB virulence gene encodes an enzyme that ADP-ribosylates actin and destabilizes the cytoskeleton of eukaryotic cells. Mol Microbiol (2001) 39(6):1464-1470.

Long, E.O. Regulation of immune responses through inhibitory receptors. Annu Rv Immunol (1999) 17:875-904.

Lorenz, U., et al. Genetic analysis reveals cell type-specific regulation of receptor tyrosine kinase c-Kit by the protein tyrosine phosphatase SHP1. J Exp Med (1996) 184:1111-1126.

Marengere, L.E., et al. Regulation of T cell receptor signaling by tyrosine phosphatase SYP association with CTLA-4. Science (1996) 272(5265):1170-1173.

Matthews, R.J., et al. Characterization of hematopoietic intracellular protein tyrosine phosphatase: description of a phosphatase containing an SH2 domain and another enriched in proline-, gluatmic acid-, serine-, and threonine-rich sequences. Mol Cell Biol (1992) 12(5):2396-2405.

Mendonca, S.M., et al. Identification of GTPase genesin the protozoa parasites *Trypanosoma cruzi* and *Leishmania amazonensis*. Biol Res (1993) 26(1-2):3-9.

Miranker, A., et al. Functionality maps of binding sites: a multiple copy simultaneous search method. Proteins: Structure, Function, and Genetics, 1991. 11:29-34.

Miskin, J.E., et al. A viral mechanism for inhibition of the cellular phosphatase calcineurin. Science (1998) 281(5376):562-565.

Murray, J.W., et al. Bundling of actin filaments by elongation factor $1\alpha$ inhibits polymerization at filament ends. J Cell Biol (1996) 135:1309-1321.

Nandan, D., et al. Activation of phosphotyrosine phosphatase activity attenuates mitogen-activated protein kinase signaling and inhibits c-FOS and nitric oxide synthase expression in macrophages infected with *Leishmania donovani*. Infection and Immunity (1999) 67:4055-4063.

Nandan, D., et al. Exploitation of host cell signaling machinery:activation of macrophage phosphotyrosine phosphatases as a novel mechanism of molecular microbial pathogenesis. J Leukocyte Biology (2000) 67:464-470.

Nandan, D. and Reiner N.E. Attenuation of gamma interferon-induced tyrosine phosphorylation in mononuclear phagocytes infected with *Leishmania donovani*: selective inhibition of signaling through Janus knases and Stat1. Infect Immun (1995) 63(11)4495-4500.

Needleman, S.B. and Wunsch, C.D. A general method applicable to the search for similarities in the amino acid sequence of two proteins. Journal of Molecular Biology (1970) 48(3):443-453.

Nitschke, L., et al. CD22 is a negative regulator of B-cell receptor signalling. Curr Biol (1997) 7(2):133-143.

Olivier, M., et al. Modulation of interferon-γ-induced macrophage activation by phosphotyrosin phosphatases inhibition. J Biol Chem (1998) 273:13944-13949.

Olivier, M., et al. Defective stimulus-response coupling in human monocytes infected with *Leishmania donovani* is associated with altered activation and translocation of protein kinase C. Proc Natl Acad Sci SA (1992) 89:7481-7485.

Olivier, M., et al. Stimulus-response coupling in monocytes infected with *Leishmania*. Attenuation of calcium transients is related to defective agonist-induced accumulation of inositol phosphates. J Immunol (1992) 148(4):1188-1196.

Ono, M., et al. Deletion of SHIP or SHP-1 reveals two distinct pathways for inhibitory signaling. Cell (1997) 90(2):293-301.

Ooms, F. Molecular modeling and computer aided drug design. Examples of their applications in medicinal chemistry. Current Medicinal Chemistry (2000) 7(2):141-58.

Pathak, M.K and Yi, T. Sodium stibogluconate is a potent inhibitor of protein tyrosine phosphatases and aguments cytokine responses in hemopoietic cell lines. J Immunol (2001) 167(6):3391-3397.

Pawson, T. Protein modules and signalling networks. Nature (1995) 373(6515):573-580.

Pei, D., et al. Differential functions of the two Src homology 2 domains in protein tyrosine phosphatase SH-PTP1. Proc Natl Acad Sci USA (1996) 93:1141-1145.

Perkins, L.A., et al. Corkscrew encodes a putative protein tyrosine phosphatase that functions to transduce the terminal signal from the receptor tyrosine kinase torso. Cell (1992) 70(2):225-236.

Piani, A., et al. *Leishmania* major proteophosphoglycan is expressed by amastigotes and has an immunomodulatory effect on macrophage function. Microbes Infect (1999) 1(8):589-599.

Pinna, L.A. Casein kinase 2:an 'eminence gris' in cellular regulation? Biochim Biophys Acta (1990) 1054(3):267-284.

Plutzky, J., et al. Isolation of a src homology 2-containing tyrosine phosphatase. Proc Nat Acad Sci (1992) 89:1123-1127.

Reiner, N.E., Altered cell signaling and mononuclear phagocyte deactivation during intracellular infection. Immunol. Today (1994) 15:374-381.

Reiner, N.E. Host-parasite relationship in murine *Leishmaniasis*: pathophysiological ad immunological changes. Infect Immun (1982) 38:1223-1230.

Reiner, N.E., et al. Kinetcs of γ interferon binding and induction of major histocompatibility complex class II mRNA in *Leishmania*-infected macrophages. Proc Natl Acad Sci (1988) 85:4330-4334.

Reiner, N.E. et al. Modulation of in vitro monocyte cytokine responses to *Leishmania donovani*. J Clin Invest (1990) 85:1914-1924.

Reiner, N.E., et al. Arachidonic acid metabolism by murine peritoneal macrophage infected with *Leishmania dononvani*: in vitro evidence for parasite-induced alterations in cyclooxygenase and lipoxygenase pathways. J Immunol (1985) 134(1):556-563.

Rey-Ladino, J.A., et al. Expression of 65- and 67-kilodalton heat-regulated proteins and a 70-kilodalton heat shock cognate protein of *Leishmania donovani* in macrophages. Infect Immun (1993) 61(8):3265-3272.

Ridgley, E.L., et al. Genomic organization and expression of elongation factor-1α genes in *Trypanosoma brucei*. Molecular and Biochemical Parasitology (1996) 79:119-123.

Rost, B. and Sander C., Prediction of protein secondary strucutre at better than 70% accuracy. J Mol Biol (1993) 232(2):584-599.

Rost, B. and Sander, C. Improved prediction of protein secondary structure by use of sequence profiles and neural networks. Proc Natl Acad Sci USA (1993) 90(16):7558-62.

Rost, B. and Sander, C. Combining evolutionary information and neural netowrks to predict protein secondary structure. Proteins-:Structure, Function and Genetics (1994) 19(1):55-72.

Sakamoto, K.M., et al. Protacs: chimeric molecules that target proteins to the Skp1-cullin-F box complex for ubiquitination and degradation. PNAS (2001) 98(15):8554-9.

Schaible, U.E. et al. Parasitophorous vacuoles of *Leishmania mexicana* acquire macromolecules from the host cell cytosol via two independent routes. J Cell Sci (1999) 112 (pt 5):681-693.

Servidei, T., et al. Coordinate regulation of STAT signaling and c-fos expression by the tyrosine phosphatase SHP-2*. J Biol Chem (1998) 273(11):6233-6241.

Shen, S.H., et al. A protein-tyrosine phosphatase with sequence similarity to the SH2 domain of the protein-tyrosine kinases. Nature (1991) 352(6337):736-739.

Shultz, L.D., et al. Severe defects in immunity and hematopoiesis caused by SHP-1 protein-tyrosine-phosphatase deficiency. Trends Biotechnol (1997) 15(8):302-307.

Shultz, L.D., et al., Mutations at the murine motheaten locus are within the hematopoietic cell protein-tyrosine phosphatase (Hcph) gene. Cell (1993) 73(7):1445-1454.

Shultz, L.D. Pleiotropic effects of deleterious alleles at the "motheaten" locus. Curr Top Microbiol Immunol (1988) 137:216-222.

Sibley, L.D., et al. *Mycobacterium leprae*-burdened macrophages are refractory to activation by gamma interferon. Infect Immun (1987) 55(2):446-450.

Sibley, L.D., et al. Inhibition of interferon-gamma-mediated activation in mouse macrophages treated with lipoarabinomannan. Clin Exp Immunol (1990) 80(1):141-148.

Siegal, G., et al. Solution structure of the C-terminal SH2 domain of the p85 alpha regulatory subunit of phosphoinositide 3-kinase. J Mol Biol (1998) 276:461-478.

Smith, T.F. and Waterman, M.S., Identification of common molecular subsequences. Journal of Molecular Biology (1981) 147(1):195-197.

Somani, A.K., et al. Src kinase activity is regulated by the SHP-1 protein-tyrosine phosphatase. J Biol Chem (1997) 272(34):21113-21119.

Sonnenberg, M.G., e al. Definition of Mycobacterium tuberculosis culture filtrate proteins by two-dimensional polyacrylamide gel electrophoresis, N-terminal amino acid sequencing, and electrospray mass spectrometry. Infect Immun (1997) 65(11):4515-4524.

Songyang, Z., et al. SH2 domains recognize specific phosphopeptide sequences. Cell (1993) 72(5):767-778.

Stein, R.C. and Waterfield, M.D. P13-kinase inhibition: a target for drug development? Mol Med Today (2000) 6:347-357.

Su, L, et al. Positive effect of overexpressed protein-tyrosine phosphatase PTP1C on mitogen-activated signaling in 293 cells*. J Biol Chem (1996) 271(17):10385-10390.

Tabrizi, M., et al. Reduced Tyk2/SHP-1 interaction and lcak of SHP-1 mutation in a kindred of familial hemophagocytic lymphohistiocytosis. Luekemia (1998) 12(2):200-206.

Tellam, J., et al. Targeting of EBNA1 for rapid intracellular degradation overrides the inhibitory effects of the Gly-Ala repeat domain and restores CD8+ T cell recognition. Journal of Biological Chemistry (2001) 276(36):33353-60.

Tonks, N.K. , et al. From form to function: signaling by protein tyrosine phosphatases. Cell (1996) 87(3):365-368.

Tsui, H.W., et al. Motheaten and viable motheaten mice have mutations in haematopoietic cell phosphatase gene. Nature Genet (1993) 4(2)124.

Turco, S.J., et al. The lipophosphoglycan of *Leishmania* parasites. Annu Rev Microbiol (1992) 46:65-94.

Uchida, T., et al. Insulin stimulates the phosphorylation of Tyr$^{538}$ and the catalytic activity of PTP1C, a protein tyrosine phosphatase with Src homology-2 domains*. J Biol Chem (1994) 269(16):12220-12228.

Vanhaesenbroeck, B., et al. Distinct PI(3)Ks mediate mitogenic signalling and cell migration in macrophages. Nat Cell Biol (1999) 1:69-71.

Veillette, A., et al. High expression of inhibitory receptor SHPS-1 and its association with protein-tyrosine phosphatase SHP-1 in macrophages*. J Biol Chem (1998) 273(35):22719-22728.

Vinkenoog, R., et al. Malaria parasites contain two identical copies of an elongation factor 1 alpha gene. Mol Biochem Parasitol (1998) 94(1);1-12.

Wang, L.L., et al. Specificity of the SH2 domains of SHP-1 in the interaction with the immunoreceptor tyrosine-based inhibitory motif-bearing receptor gp49B J Immunol (1999) 162:1318-1323.

Webb, J.R., et al. *Leishmania* major HEXBP deletion mutants generated by double targeted gene replacement. Mol Biochem Parasitol (1994) 63(2):231-242.

Weldingh, K., et al. Two-dimensional electrophoresis for analysis of mycobacterium tuberculosis culture filtrate and purification and characterization of six novel proteins. Infection and Immunity (1998) 66(8):3492-3500.

Yeremeev, V.V., et al. The 19-dk antigen and protective immunity in a murine model of tuberculosis. Clin Exp Immunol (2000) 120:274-279.

Yetter, A., et al. Association of the interferon-dependent tyrosine kinase Tyuk-2 with the hematopoietic cell phosphatase. J Biol Chem (1995) 270(31):18179-18182.

Yi, T., et al. Hematopoietic cell phosphatase associates with the interleukin-3 (IL-3_receptor β chain and down-regulates IL-3-induced tyrosine phosphorylation and mitogenesis. Mol Cell Biol (1993) 13(12):7577-7586.

Yi, T., et al. Protein tyrosine phosphatase containing SH2 domains: characterization , preferential expression in hematopoietic cells, and localization to human chromosome 12p12-p13. Mol Cell Biol (1992) 12(2):836-846.

Yohannan, J., et al. Analysis of tyrosine phosphorylation-dependent interactions between stimulatory effector proteins and the B cell co-receptor CD22. J Biol Chem (1999) 274:18769-18776.

You, M., et al. Positive effects of SH2 domain-containing tyrosine phosphatase SHP-1 on epidermal growth factor-1 and interferon-γ-stimulated activation of STAT transcription factors in HeLa cells. J Biol Chem (1997) 272(37):23376-23381.

You, M., et al. Shp-2 tyrosine phosphatase functions as a negative regulator of the interferon-stimulated Jak/STAT pathway. Mol Cell Biol (1999) 19(3):2416-2424.

Zhang, Z.Y. Protein-tyrosine phosphatases: biological function, structural characteristics, and mechanism of catalysis. Crit Rev Biochem Mol Biol (1998) 33(1):1-52.

Database Swissprot 'Online! Brands, J.G.H.M. et al., "Elongation factor 1-alpha 1" Database accession No. P04720 (Document No. XP-002232634).

Rey-Ladino, et al., "*Leishmania* major: molecular cloning, sequencing, and expression of the heat shock protein 60 gene reveals unique carboxy terminal peptide sequences", Experimental Parasitology vol. 85, No. 3, pp. 249-263 (1997), Article No. PR964137.

Database Genembl 'Online! Nandan, D. E., et al., "*Leishmania donovani* elongation factor 1-alpha mRNA, partial cds", Database accession No. AF 416379 (Document No. XP-002232635).

Database Genembl 'Online! Billaut-Molot, O. et al., "*Trypanosoma cruzi* elongation factor 1-alpha gene", Database accession No. L76077 (Document No. XP-002232636).

Database Genembl 'Online! De Meester F., et al. "Entamoebahistolytica elongation factor- 1 alpha", Database accession No. M92073 (Document No. XP-002232637).

Database Genembl 'Online! Williamson, D. H., "*P. falciparum* MEF-1 gene for EF-1 alpha elongation factor", Database accession No. X60488 (Document No. XP-002232638).

Database Genembl 'Online! Mead, J. R., et al. "*Cryptosporidium parvum* elongation factor 1-alpha (EF-1 alpha)" Database accession No. U69697 (Document No. XP-002232639).

Database Genembl 'Online! Hashimoto, "*G. lamblia* mRNA for elongation factor 1-alpha, partial cds", Database accession No. D14342 (Document No. XP-002232640).

Nandan Devki et al., "*Leishmania* EF-1α activates the Src homology 2 domain containing tyrosine phosphatase SHP-1 leading to macrophage deactivation ", Journal of Biological Chemistry, (2002) vol. 277, No. 51, pp. 5019050197 (Document No. XP-002232633).

* cited by examiner

Figure 1A n = 135 residues

```
Entamoeba    HILLSYTLGVKQMIVGVNKMD--AIQYKQERYEEIKKEISAFLKKTGYNPDKIPFVPISGFQGDNMIEPSTNMPWYKGPTLIGALDSVTPPERP
Trypanosoma  HALLAFTLGVRQMIVGINKMD--TCEYKQSRFDEIFNEVDGYLKKVGYNTEKIPFVAISGFVGDNMVERSDKMPWYKGKTLVEALDTMEPPKRP
Crypto.      HALLAFTLGVRQMIVGINKMD--TCEYKQSRFDEIFNEVDGYLKKVGYNTEKIPFVAISGFVGDNMVERSDKMPWYKGKTLVEALDTMEPPKRP
Plasmodium   HALLAFTLGVKQIVVGVNKMD--TVKYSEDRYEEIKKEVKDYLKKVGYQADKVDFIPISGFEGDNLIEKSDKTPWYKGRTLIEALDTMEPPKRP
Leishmania   HALLAFTLGVKQMVVCCNKMDDKTVTYAQSRYDBISKEVGAYLKRVGYNPEKVRFIPISGWQGDNMIERSDNMPWYKGPTLLDALDMLEPPVRP
Giardia      HILLSYTLGVKQMIVGVNKMD--AIQYKQERYEEIKKEISAFLKKTGYNPDKIPFVPISGFQGDNMIEPSTNMPWYKGPTLIGALDSVTPPERP
Homo sapien  HALLAYTLGVKQLIVGVNKMDSTEPPYSQKRYEEIVKEVSTYIKKIGYNPDTVAFVPISGWNGDNMLEPSANMPWFKGTTLLEALDCILPPTRP
```

```
                                                                                        GWKVTRKDGNAS
                                                                                        "indel"
                                                                                        n = 212
```

Figure 1B

A. Human EF-1α

B. Leishmania EF-1α

SEQUENCE LISTING

```
<160> NUMBER OF SEQ ID NOS: 38

<210> SEQ ID NO 1
<211> LENGTH: 10
<212> TYPE: PRT
<213> ORGANISM: Leishmani donavi

<400> SEQUENCE: 1

Thr Leu Leu Asp Ala Leu Asp Met Leu Glu
1               5                   10

<210> SEQ ID NO 2
<211> LENGTH: 9
<212> TYPE: PRT
<213> ORGANISM: Leishmani donavi

<400> SEQUENCE: 2

Glu Lys Val Arg Phe Ile Pro Ile Ser
1               5

<210> SEQ ID NO 3
<211> LENGTH: 11
<212> TYPE: PRT
<213> ORGANISM: Leishmani donavi

<400> SEQUENCE: 3

Lys Thr Val Thr Tyr Ala Gln Ser Arg Tyr Asp
1               5                   10

<210> SEQ ID NO 4
<211> LENGTH: 10
<212> TYPE: PRT
<213> ORGANISM: Trypanosoma cruzi

<400> SEQUENCE: 4

Thr Leu Leu Glu Ala Leu Asp Met Leu Glu
1               5                   10

<210> SEQ ID NO 5
<211> LENGTH: 9
<212> TYPE: PRT
<213> ORGANISM: Trypanosoma cruzi

<400> SEQUENCE: 5

Glu Lys Val Arg Phe Ile Pro Ile Ser
1               5
```

```
<210> SEQ ID NO 6
<211> LENGTH: 11
<212> TYPE: PRT
<213> ORGANISM: Trypanosoma cruzi

<400> SEQUENCE: 6

Lys Ser Val Asn Phe Ala Gln Glu Arg Tyr Asp
1               5                   10

<210> SEQ ID NO 7
<211> LENGTH: 11
<212> TYPE: PRT
<213> ORGANISM: Cryptosporidium parvum

<400> SEQUENCE: 7

Thr Leu Val Glu Ala Leu Asp Thr Met Glu Pro
1               5                   10

<210> SEQ ID NO 8
<211> LENGTH: 9
<212> TYPE: PRT
<213> ORGANISM: Cryptosporidium parvum

<400> SEQUENCE: 8

Glu Lys Ile Pro Phe Val Ala Ile Ser
1               5

<210> SEQ ID NO 9
<211> LENGTH: 11
<212> TYPE: PRT
<213> ORGANISM: Cryptosporidium parvum

<400> SEQUENCE: 9

Asp Thr Cys Glu Tyr Lys Gln Ser Arg Phe Asp
1               5                   10

<210> SEQ ID NO 10
<211> LENGTH: 10
<212> TYPE: PRT
<213> ORGANISM: Plasmodium flaciparum

<400> SEQUENCE: 10

Thr Leu Ile Glu Ala Leu Asp Thr Met Glu
1               5                   10

<210> SEQ ID NO 11
<211> LENGTH: 9
<212> TYPE: PRT
<213> ORGANISM: Plasmodium flaciparum

<400> SEQUENCE: 11

Asp Lys Val Asp Phe Ile Pro Ile Ser
1               5

<210> SEQ ID NO 12
<211> LENGTH: 11
<212> TYPE: PRT
<213> ORGANISM: Plasmodium flaciparum

<400> SEQUENCE: 12

Asp Thr Val Lys Tyr Ser Glu Asp Arg Tyr Glu
1               5                   10

<210> SEQ ID NO 13
<211> LENGTH: 10
```

```
<212> TYPE: PRT
<213> ORGANISM: Entamoeba histolytica

<400> SEQUENCE: 13

Thr Leu Ile Gly Ala Leu Asp Ser Val Thr
1               5                   10

<210> SEQ ID NO 14
<211> LENGTH: 9
<212> TYPE: PRT
<213> ORGANISM: Entamoeba histolytica

<400> SEQUENCE: 14

Asp Lys Ile Pro Phe Val Pro Ile Ser
1               5

<210> SEQ ID NO 15
<211> LENGTH: 11
<212> TYPE: PRT
<213> ORGANISM: Entamoeba histolytica

<400> SEQUENCE: 15

Asp Ala Ile Gln Tyr Lys Gln Glu Arg Tyr Glu
1               5                   10

<210> SEQ ID NO 16
<211> LENGTH: 10
<212> TYPE: PRT
<213> ORGANISM: Giardia intestinalis

<400> SEQUENCE: 16

Cys Leu Ile Asp Ala Ile Asp Gly Leu Lys
1               5                   10

<210> SEQ ID NO 17
<211> LENGTH: 9
<212> TYPE: PRT
<213> ORGANISM: Giardia intestinalis

<400> SEQUENCE: 17

Glu Glu Phe Asp Tyr Ile Pro Thr Ser
1               5

<210> SEQ ID NO 18
<211> LENGTH: 11
<212> TYPE: PRT
<213> ORGANISM: Giardia intestinalis

<400> SEQUENCE: 18

Gly Gln Val Lys Tyr Ser Lys Glu Arg Tyr Asp
1               5                   10

<210> SEQ ID NO 19
<211> LENGTH: 21
<212> TYPE: PRT
<213> ORGANISM: L. braziliensis

<400> SEQUENCE: 19

Ala Cys Cys Ala Thr Gly Gly Gly Cys Ala Ala Gly Gly Ala Thr Ala
1               5                   10                  15

Ala Gly Gly Thr Gly
            20

<210> SEQ ID NO 20
```

```
<211> LENGTH: 17
<212> TYPE: PRT
<213> ORGANISM: L. braziliensis

<400> SEQUENCE: 20

Cys Thr Thr Cys Thr Thr Cys Gly Cys Ala Gly Cys Cys Thr Thr Cys
1               5                   10                  15

Gly

<210> SEQ ID NO 21
<211> LENGTH: 1347
<212> TYPE: DNA
<213> ORGANISM: Leishmania donovani

<400> SEQUENCE: 21
atgggcaagg ataaggtgca catgaacctt gtggtcgtcg gccatgtcga cgccggcaag      60
tccaccgcca ctggccactt gatctacaag tgcggtggca tcgacaagcg cacgatcgag     120
aagttcgaga aggaggccgc cgagatcggc aaggcgtcct tcaagtacgc gtgggtgctc     180
gacaagctga aggcggagcg cgagcgcggc atcacgatcg acattgcgct gtggaagttc     240
gagtcgccca gtccgtgtt cacgatcatc gatgcgcccg ccaccgcga cttcatcaag      300 aacatgatca cgggcacgtc gcaggcggac gccgccatcc tgatgatcga ctcgacgcat     360
ggtggcttcg aggctggcat ctcgaaggac ggccagaccc gcgagcacgc gctgcttgcc     420
ttcacgcttg gcgtgaagca gatggtggtg tgctgcaaca agatggacga caagaccgtg     480
acgtacgcgc agtcgcgcta cgatgagatc agcaaggagg tgggcgcgta cctgaagcgc     540
gtgggctaca ccccgagaa ggtgcgcttc atcccgatct cgggctggca gggcgacaac     600
atgatcgaga ggtcggacaa catgccgtgg tacaagggtc ccacgctgct ggacgcgctc     660
gacatgctgg agccgccggt gcgcccggtg gacaagccgc tgcgcctgcc cctgcaggac     720
gtgtacaaga tcggcggtat cgggactgtg cccgtgggcc gcgtggagac cggcatcatg     780
aagccgggcg acgtggtgac gttcgcgccc gccaacgtga cgactgaggt gaagtcgatc     840
gagatgcacc acgagcagct ggcggaggcg cagcccggcg acaacgtcgg cttcaacgtg     900
aagaacgtgt cggtgaagga catccgccgt ggcaacgtgt gcggcaactc gaagaacgac     960
ccgccgaagg aggcggccga cttcacggcg caggtgatcg tgctgaacca ccccggccag    1020
atcagcaacg gctacgcgcc ggtgctggac tgccacacga gccacattgc gtgccgcttc    1080
gcggaaatcg agtccaagat cgaccgccgc tccggcaagg agctggagaa gaaccccaag    1140
gcgatcaagt ctggcgatgc cgcgatcgtg aagatggtgc gcagaagcc gatgtgcgtg    1200 gaggtgttca cgactacgc gccgctgggc cgctttgccg tgcgcgacat gcggcagacg    1260
gtggccgtgg gcatcatcaa gggcgtgaac aagaaggagg gcagcggcgg taaggtgacc    1320
aaggcggccg cgaaggctgc gaagaag                                        1347

<210> SEQ ID NO 22
<211> LENGTH: 443
<212> TYPE: PRT
<213> ORGANISM: Leishmania donovani

<400> SEQUENCE: 22

Met Gly Lys Asp Lys Val His Met Asn Leu Val Val Val Gly His Val
1               5                   10                  15

Asp Ala Gly Lys Ser Thr Ala Thr Gly His Leu Ile Tyr Lys Cys Gly
            20                  25                  30
```

-continued

```
Gly Ile Asp Lys Arg Thr Ile Glu Lys Phe Glu Lys Glu Ala Ala Glu
            35                  40                  45

Ile Gly Lys Ala Ser Phe Lys Tyr Ala Trp Val Leu Asp Lys Leu Lys
 50                  55                  60

Ala Glu Arg Glu Arg Gly Ile Thr Ile Asp Ile Ala Leu Trp Lys Phe
 65                  70                  75                  80

Glu Ser Pro Lys Ser Val Phe Thr Ile Ile Asp Ala Pro Gly His Arg
                 85                  90                  95

Asp Phe Ile Lys Asn Met Ile Thr Gly Thr Ser Gln Ala Asp Ala Ala
                100                 105                 110

Ile Leu Met Ile Asp Ser Thr His Gly Gly Phe Glu Ala Gly Ile Ser
            115                 120                 125

Lys Asp Gly Gln Thr Arg Glu His Ala Leu Leu Ala Phe Thr Leu Gly
130                 135                 140

Val Lys Gln Met Val Val Cys Asn Lys Met Asp Asp Lys Thr Val Thr
145                 150                 155                 160

Tyr Ala Gln Ser Arg Tyr Asp Glu Ile Ser Lys Glu Val Gly Ala Tyr
                165                 170                 175

Leu Lys Arg Val Gly Tyr Asn Pro Glu Lys Val Arg Phe Ile Pro Ile
            180                 185                 190

Ser Gly Trp Gln Gly Asp Asn Ile Glu Arg Ser Asp Asn Met Pro Trp
        195                 200                 205

Tyr Lys Gly Pro Thr Leu Leu Asp Ala Leu Asp Met Leu Glu Pro Pro
    210                 215                 220

Val Arg Pro Val Asp Lys Pro Leu Arg Leu Pro Leu Gln Asp Val Tyr
225                 230                 235                 240

Lys Ile Gly Gly Ile Gly Thr Val Pro Gly Arg Val Glu Thr Gly Ile
                245                 250                 255

Met Lys Pro Gly Asp Val Val Thr Phe Ala Pro Ala Asn Val Thr Thr
            260                 265                 270

Glu Val Lys Ser Ile Glu Met His His Glu Gln Leu Ala Glu Ala Gln
        275                 280                 285

Pro Gly Asp Asn Val Gly Phe Asn Val Lys Val Ser Val Lys Asp Ile
    290                 295                 300

Arg Arg Gly Asn Val Cys Gly Asn Ser Lys Asn Asp Pro Pro Lys Glu
305                 310                 315                 320

Ala Ala Asp Phe Thr Ala Gln Val Ile Val Leu Asn His Pro Gly Gln
                325                 330                 335

Ile Ser Asn Gly Tyr Ala Pro Val Leu Asp Cys His Ser His Ile Ala
            340                 345                 350

Cys Arg Phe Ala Glu Ile Glu Ser Lys Ile Asp Arg Arg Ser Gly Lys
        355                 360                 365

Glu Leu Glu Lys Asn Pro Lys Ala Ile Lys Ser Gly Asp Ala Ala Ile
    370                 375                 380

Val Lys Met Val Pro Gln Lys Pro Met Cys Val Glu Val Phe Asn Tyr
385                 390                 395                 400

Ala Pro Leu Gly Arg Phe Ala Val Arg Asp Met Arg Gln Thr Val Ala
                405                 410                 415

Val Gly Ile Ile Lys Gly Val Asn Lys Lys Glu Gly Ser Gly Gly Lys
            420                 425                 430

Val Thr Lys Ala Ala Ala Lys Ala Ala Lys Lys
        435                 440
```

<210> SEQ ID NO 23
<211> LENGTH: 458
<212> TYPE: PRT
<213> ORGANISM: Saccharomyces cerevisiae

<400> SEQUENCE: 23

```
Met Gly Lys Glu Lys Ser His Ile Asn Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Leu Gly Lys Gly Ser Phe Lys Tyr Ala Trp Val Leu Asp Lys Leu Lys
    50                  55                  60

Ala Glu Arg Glu Arg Gly Ile Thr Ile Asp Ala Leu Trp Lys Phe
65                  70                  75                  80

Glu Thr Pro Lys Tyr Gln Val Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Ile Leu Ile Ile Ala Gly Gly Val Gly Glu Phe Glu Ala Gly Ile Ser
        115                 120                 125

Lys Asp Gly Gln Thr Arg Glu His Ala Leu Leu Ala Phe Thr Leu Gly
    130                 135                 140

Val Arg Gln Leu Ile Val Ala Val Asn Lys Met Asp Ser Val Lys Trp
145                 150                 155                 160

Asp Glu Ser Arg Phe Gln Glu Ile Val Lys Glu Thr Ser Asn Phe Ile
                165                 170                 175

Lys Lys Val Gly Tyr Asn Pro Lys Thr Val Pro Phe Val Pro Ile Ser
            180                 185                 190

Gly Trp Asn Gly Asp Asn Met Ile Glu Ala Thr Thr Asn Ala Pro Trp
        195                 200                 205

Tyr Lys Gly Trp Glu Lys Glu Thr Lys Ala Gly Val Val Lys Gly Lys
    210                 215                 220

Thr Leu Leu Glu Ala Ile Asp Ala Ile Glu Gln Pro Ser Arg Pro Thr
225                 230                 235                 240

Asp Lys Pro Leu Arg Leu Pro Leu Gln Asp Val Tyr Lys Ile Gly Gly
                245                 250                 255

Ile Gly Thr Val Pro Val Gly Arg Val Glu Thr Gly Val Ile Lys Pro
            260                 265                 270

Gly Met Val Val Thr Phe Ala Pro Ala Gly Val Thr Thr Glu Val Lys
        275                 280                 285

Ser Val Glu Met His His Glu Gln Leu Glu Gln Gly Val Pro Gly Asp
    290                 295                 300

Asn Val Gly Phe Asn Val Lys Asn Val Ser Val Lys Glu Ile Arg Arg
305                 310                 315                 320

Gly Asn Val Cys Gly Asp Ala Lys Asn Asp Pro Pro Lys Gly Cys Ala
                325                 330                 335

Ser Phe Asn Ala Thr Val Ile Val Leu Asn His Pro Gly Gln Ile Ser
            340                 345                 350

Ala Gly Tyr Ser Pro Val Leu Asp Cys His Thr Ala His Ile Ala Cys
        355                 360                 365

Arg Phe Asp Glu Leu Leu Glu Lys Asn Asp Arg Arg Ser Gly Lys Lys
    370                 375                 380
```

```
Leu Glu Asp His Pro Lys Phe Leu Lys Ser Gly Asp Ala Ala Leu Val
385                 390                 395                 400

Lys Phe Val Pro Ser Lys Pro Met Cys Val Glu Ala Phe Ser Glu Tyr
            405                 410                 415

Pro Pro Leu Gly Arg Phe Ala Val Arg Asp Met Arg Gln Thr Val Ala
            420                 425                 430

Val Gly Val Ile Lys Ser Val Asp Lys Thr Glu Lys Ala Ala Lys Val
            435                 440                 445

Thr Lys Ala Ala Gln Lys Ala Ala Lys Lys
    450                 455

<210> SEQ ID NO 24
<211> LENGTH: 462
<212> TYPE: PRT
<213> ORGANISM: Mus musculus

<400> SEQUENCE: 24

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Ser Ala Ser
210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Ser Glu Ala Leu Pro
    290                 295                 300
```

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Pro Met Glu
            325                 330                 335

Ala Ala Gly Phe Thr Ala Gln Val Ile Ile Leu Asn His Pro Gly Gln
            340                 345                 350

Ile Ser Ala Gly Tyr Ala Pro Val Leu Asp Cys His Thr Ala His Ile
        355                 360                 365

Ala Cys Lys Phe Ala Glu Leu Lys Glu Lys Ile Asp Arg Arg Ser Gly
370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
                405                 410                 415

Asp Tyr Pro Pro Leu Gly Arg Phe Ala Val Arg Asp Met Arg Gln Thr
            420                 425                 430

Val Ala Val Gly Val Ile Lys Ala Val Asp Lys Lys Ala Ala Gly Ala
            435                 440                 445

Gly Lys Val Thr Lys Ser Ala Gln Lys Ala Gln Lys Ala Lys
    450                 455                 460

<210> SEQ ID NO 25
<211> LENGTH: 462
<212> TYPE: PRT
<213> ORGANISM: Homo sapiens

<400> SEQUENCE: 25

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser

```
                210                 215                 220
Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
                260                 265                 270

Lys Pro Gly Met Val Val Thr Phe Ala Pro Val Asn Val Thr Thr Glu
            275                 280                 285

Val Lys Ser Val Glu Met His His Glu Ala Leu Ser Glu Ala Leu Pro
290                 295                 300

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Ala Gly Phe Thr Ala Gln Val Ile Ile Leu Asn His Pro Gly Gln
                340                 345                 350

Ile Ser Ala Gly Tyr Ala Pro Val Leu Asp Cys His Thr Ala His Ile
            355                 360                 365

Ala Cys Lys Phe Ala Glu Leu Lys Glu Lys Ile Asp Arg Arg Ser Gly
370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
                405                 410                 415

Asp Tyr Pro Pro Leu Gly Arg Phe Ala Val Arg Asp Met Arg Gln Thr
                420                 425                 430

Val Ala Val Gly Val Ile Lys Ala Val Asp Lys Lys Ala Ala Gly Ala
            435                 440                 445

Gly Lys Val Thr Lys Ser Ala Gln Lys Ala Gln Lys Ala Lys
        450                 455                 460

<210> SEQ ID NO 26
<211> LENGTH: 14
<212> TYPE: PRT
<213> ORGANISM: Homo sapiens

<400> SEQUENCE: 26

Gly Trp Lys Val Thr Arg Lys Asp Gly Asn Ala Ser Gly Thr
1               5                   10

<210> SEQ ID NO 27
<211> LENGTH: 449
<212> TYPE: PRT
<213> ORGANISM: Leishmania donovani
<220> FEATURE:
<221> NAME/KEY: MISC_FEATURE
<222> LOCATION: (1)..(449)
<223> OTHER INFORMATION: Xaa = any amino acid

<400> SEQUENCE: 27

Met Gly Lys Asp Lys Val His Met Asn Leu Val Val Val Gly His Val
1               5                   10                  15

Asp Ala Gly Lys Ser Thr Ala Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45
```

Ile Gly Lys Ala Xaa Xaa Xaa Tyr Ala Xaa Val Leu Asp Lys Leu Lys
            50                  55                  60

Ala Glu Arg Glu Arg Gly Ile Thr Ile Asp Ile Ala Leu Trp Lys Phe
 65                  70                  75                  80

Glu Ser Pro Lys Ser Val Phe Thr Ile Ile Asp Ala Pro Gly His Arg
                 85                  90                  95

Asp Phe Ile Lys Asn Met Ile Thr Gly Thr Ser Gln Ala Asp Ala Ala
            100                 105                 110

Ile Leu Met Ile Asp Ser Thr His Gly Gly Phe Glu Ala Gly Ile Ser
            115                 120                 125

Lys Asp Gly Gln Thr Arg Glu His Ala Leu Leu Ala Phe Thr Leu Gly
130                 135                 140

Val Lys Gln Met Val Val Cys Cys Asn Lys Met Asp Asp Lys Thr Val
145                 150                 155                 160

Thr Tyr Ala Gln Ser Arg Tyr Asp Glu Ile Ser Lys Glu Val Gly Ala
                165                 170                 175

Tyr Leu Lys Arg Val Gly Tyr Asn Pro Glu Lys Val Arg Phe Ile Pro
            180                 185                 190

Ile Ser Gly Trp Gln Gly Asp Asn Met Ile Glu Arg Ser Asp Asn Met
            195                 200                 205

Pro Trp Tyr Lys Gly Pro Thr Leu Leu Asp Ala Leu Asp Met Leu Glu
210                 215                 220

Pro Pro Val Arg Pro Val Asp Lys Pro Leu Arg Leu Pro Leu Gln Asp
225                 230                 235                 240

Val Tyr Lys Ile Gly Gly Ile Gly Thr Val Pro Val Gly Arg Val Glu
                245                 250                 255

Thr Gly Ile Met Lys Pro Gly Asp Val Val Thr Phe Ala Pro Ala Asn
            260                 265                 270

Val Thr Thr Glu Val Lys Ser Ile Glu Met His His Glu Gln Leu Ala
            275                 280                 285

Glu Ala Gln Pro Gly Asp Asn Val Gly Phe Asn Val Lys Asn Val Ser
290                 295                 300

Val Lys Asp Ile Arg Arg Gly Asn Val Cys Gly Asn Ser Lys Asn Asp
305                 310                 315                 320

Pro Pro Lys Glu Ala Ala Asp Phe Thr Ala Gln Val Ile Val Leu Asn
                325                 330                 335

His Pro Gly Gln Ile Xaa Xaa Xaa Tyr Ala Xaa Val Leu Asp Cys His
            340                 345                 350

Thr Ser His Ile Ala Cys Arg Phe Ala Glu Ile Glu Ser Lys Ile Asp
            355                 360                 365

Arg Arg Ser Gly Lys Glu Leu Glu Lys Asn Pro Lys Ala Ile Lys Ser
370                 375                 380

Gly Asp Ala Ala Ile Val Lys Met Val Pro Gln Lys Pro Met Cys Val
385                 390                 395                 400

Glu Val Phe Asn Asp Tyr Ala Pro Leu Gly Arg Phe Ala Val Arg Asp
                405                 410                 415

Met Arg Gln Thr Val Ala Val Gly Ile Ile Lys Gly Val Asn Lys Lys
            420                 425                 430

Glu Gly Ser Gly Gly Lys Val Thr Lys Ala Ala Lys Ala Ala Lys
            435                 440                 445

Lys

<210> SEQ ID NO 28

<211> LENGTH: 447
<212> TYPE: PRT
<213> ORGANISM: Leishmania Brazileinsis
<220> FEATURE:
<221> NAME/KEY: MISC_FEATURE
<222> LOCATION: (1)..(447)
<223> OTHER INFORMATION: Xaa = any amino acid

<400> SEQUENCE: 28

```

```
Arg Ser Gly Lys Asp Val Glu Lys Asn Pro Lys Ala Ile Lys Ser Gly
        370                 375                 380

Asp Ala Ala Ile Val Lys Met Val Pro Gln Lys Pro Met Cys Val Glu
385                 390                 395                 400

Val Phe Asn Asp Tyr Pro Pro Leu Gly Arg Phe Ala Val Arg Asp Met
                405                 410                 415

Arg Arg Thr Val Ala Val Gly Ile Ile Lys Ala Val Ser Lys Lys Asp
            420                 425                 430

Gly Ser Arg Lys Val Thr Lys Ala Ala Ala Lys Ala Ala Lys Lys
        435                 440                 445

<210> SEQ ID NO 29
<211> LENGTH: 449
<212> TYPE: PRT
<213> ORGANISM: Trypanosome brucei
<220> FEATURE:
<221> NAME/KEY: MISC_FEATURE
<222> LOCATION: (1)..(449)
<223> OTHER INFORMATION: Xaa = any amino acid

<400> SEQUENCE: 29

Met Gly Lys Glu Lys Val His Met Asn Leu Val Val Gly His Val
1               5                   10                  15

Asp Ala Gly Lys Ser Thr Ala Thr Gly His Leu Ile Tyr Lys Cys Gly
                20                  25                  30

Gly Ile Asp Lys Arg Thr Ile Glu Lys Phe Glu Lys Glu Ala Ala Asp
            35                  40                  45

Ile Gly Lys Ala Xaa Xaa Xaa Tyr Ala Xaa Val Leu Asp Lys Leu Lys
        50                  55                  60

Ala Glu Arg Glu Arg Gly Ile Thr Ile Asp Ile Ala Leu Trp Lys Phe
65                  70                  75                  80

Glu Ser Pro Lys Ser Val Phe Thr Ile Ile Asp Ala Pro Gly His Arg
                85                  90                  95

Asp Phe Ile Lys Asn Met Ile Thr Gly Thr Ser Gln Ala Asp Ala Ala
            100                 105                 110

Ile Leu Ile Ile Ala Ser Ala Gln Gly Glu Phe Glu Ala Gly Ile Ser
        115                 120                 125

Lys Asp Gly Gln Thr Arg Glu His Ala Leu Leu Ala Phe Thr Leu Gly
130                 135                 140

Val Lys Gln Met Val Val Cys Cys Asn Lys Met Asp Asp Lys Thr Val
145                 150                 155                 160

Asn Tyr Gly Gln Glu Arg Tyr Asp Glu Ile Val Lys Glu Val Ser Ala
                165                 170                 175

Tyr Ile Lys Lys Val Gly Tyr Asn Val Glu Lys Val Arg Phe Val Pro
            180                 185                 190

Ile Ser Gly Trp Gln Gly Asp Asn Met Ile Glu Lys Ser Glu Lys Met
        195                 200                 205

Pro Trp Tyr Lys Gly Pro Thr Leu Leu Glu Ala Leu Asp Met Leu Glu
210                 215                 220

Pro Pro Val Arg Pro Ser Asp Lys Pro Leu Arg Leu Pro Leu Gln Thr
225                 230                 235                 240

Cys Thr Lys Ile Gly Gly Ile Gly Thr Val Pro Val Gly Arg Val Glu
                245                 250                 255

Thr Gly Val Met Lys Pro Gly Asp Val Val Thr Phe Ala Pro Ala Asn
            260                 265                 270

Val Thr Thr Glu Val Lys Ser Ile Glu Met His His Glu Gln Leu Ala
```

```
                    275                 280                 285
Glu Ala Thr Pro Gly Asp Asn Val Gly Phe Asn Val Lys Asn Val Ser
            290                 295                 300
Val Lys Asp Ile Arg Arg Gly Asn Val Cys Gly Asn Thr Lys Asn Asp
305                 310                 315                 320
Pro Pro Lys Glu Ala Asp Phe Thr Ala Gln Val Ile Ile Leu Asn
                325                 330                 335
His Pro Gly Gln Ile Gly Xaa Xaa Tyr Ala Xaa Val Leu Asp Cys His
                340                 345                 350
Thr Ser His Ile Ala Cys Arg Phe Ala Glu Ile Glu Ser Lys Ile Asp
            355                 360                 365
Arg Arg Ser Gly Lys Glu Leu Glu Lys Ala Pro Lys Ser Ile Lys Ser
        370                 375                 380
Gly Asp Ala Ala Ile Val Arg Met Val Pro Gln Lys Pro Met Cys Val
385                 390                 395                 400
Glu Val Phe Asn Asp Tyr Ala Pro Leu Gly Arg Phe Ala Val Arg Asp
                405                 410                 415
Met Arg Gln Thr Val Ala Val Gly Ile Ile Lys Ala Val Thr Lys Lys
            420                 425                 430
Asp Gly Ser Gly Gly Lys Val Thr Lys Ala Ala Val Lys Ala Ser Lys
        435                 440                 445
Lys

<210> SEQ ID NO 30
<211> LENGTH: 462
<212> TYPE: PRT
<213> ORGANISM: Homo spaiens
<220> FEATURE:
<221> NAME/KEY: MISC_FEATURE
<222> LOCATION: (1)..(462)
<223> OTHER INFORMATION: Xaa = any amino acid

<400> SEQUENCE: 30

Met Gly Lys Glu Lys Thr His Ile Asn Ile Val Val Ile Gly His Val
1               5                   10                  15
Asp Ser Gly Lys Ser Thr Thr Thr Gly His Leu Ile Tyr Lys Cys Gly
            20                  25                  30
Gly Ile Asp Lys Arg Thr Ile Glu Lys Phe Glu Lys Glu Ala Ala Glu
        35                  40                  45
Met Gly Lys Gly Xaa Xaa Xaa Tyr Ala Xaa Val Leu Asp Lys Leu Lys
    50                  55                  60
Ala Glu Arg Glu Arg Gly Ile Thr Ile Asp Ile Ser Leu Trp Lys Phe
65                  70                  75                  80
Glu Thr Ser Lys Tyr Tyr Val Thr Ile Ile Asp Ala Pro Gly His Arg
                85                  90                  95
Asp Phe Ile Lys Asn Met Ile Thr Gly Thr Ser Gln Ala Asp Cys Ala
            100                 105                 110
Val Leu Ile Val Ala Ala Gly Val Gly Glu Phe Glu Ala Gly Ile Ser
        115                 120                 125
Lys Asp Gly Gln Thr Arg Glu His Ala Leu Leu Ala Phe Thr Leu Gly
    130                 135                 140
Val Lys Gln Met Val Val Gly Val Asn Lys Met Asp Ser Thr Glu Pro
145                 150                 155                 160
Pro Tyr Ser Gln Lys Arg Tyr Glu Glu Ile Val Lys Glu Val Ser Thr
                165                 170                 175
```

```
Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Ser Glu Ala Leu Pro
290                 295                 300

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Met Glu
                325                 330                 335

Ala Ala Gly Phe Thr Ala Gln Val Ile Ile Leu Asn His Pro Gly Gln
            340                 345                 350

Ile Xaa Ala Xaa Tyr Ala Xaa Val Leu Asp Cys His Thr Ala His Ile
        355                 360                 365

Ala Cys Lys Phe Ala Glu Leu Lys Glu Lys Ile Asp Arg Arg Ser Gly
370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
                405                 410                 415

Asp Tyr Pro Pro Leu Gly Arg Phe Ala Val Arg Asp Met Arg Gln Thr
            420                 425                 430

Val Ala Val Gly Val Ile Lys Ala Val Asp Lys Ala Ala Gly Ala
        435                 440                 445

Gly Lys Val Thr Lys Ser Ala Gln Lys Ala Gln Lys Ala Lys
    450                 455                 460

<210> SEQ ID NO 31
<211> LENGTH: 92
<212> TYPE: PRT
<213> ORGANISM: Entamoeba histolytica

<400> SEQUENCE: 31

His Ile Leu Leu Ser Tyr Thr Leu Gly Val Lys Gln Met Ile Val Gly
1               5                   10                  15

Val Asn Lys Met Asp Ala Ile Gln Tyr Lys Gln Glu Arg Tyr Glu Glu
                20                  25                  30

Ile Lys Lys Glu Ile Ser Ala Phe Leu Lys Lys Thr Gly Tyr Asn Pro
            35                  40                  45

Asp Lys Ile Pro Phe Val Pro Ile Ser Gly Phe Gln Gly Asp Asn Met
        50                  55                  60

Ile Glu Pro Ser Thr Asn Met Pro Trp Tyr Lys Gly Pro Thr Leu Ile
65                  70                  75                  80

Gly Ala Leu Asp Ser Val Thr Pro Pro Glu Arg Pro
                85                  90
```

<210> SEQ ID NO 32
<211> LENGTH: 92
<212> TYPE: PRT
<213> ORGANISM: Trypanosoma cruzi

<400> SEQUENCE: 32

His Ala Leu Leu Ala Phe Thr Leu Gly Val Arg Gln Met Ile Val Gly
1               5                   10                  15

Ile Asn Lys Met Asp Thr Cys Glu Tyr Lys Gln Ser Arg Phe Asp Glu
            20                  25                  30

Ile Phe Asn Glu Val Asp Gly Tyr Leu Lys Val Gly Tyr Asn Thr
        35                  40                  45

Glu Lys Ile Pro Phe Val Ala Ile Ser Gly Phe Val Gly Asp Asn Met
    50                  55                  60

Val Glu Arg Ser Asp Lys Met Pro Trp Tyr Lys Gly Lys Thr Leu Val
65                  70                  75                  80

Glu Ala Leu Asp Thr Met Glu Pro Pro Lys Arg Pro
                85                  90

<210> SEQ ID NO 33
<211> LENGTH: 92
<212> TYPE: PRT
<213> ORGANISM: Cryptosporidium parvum

<400> SEQUENCE: 33

His Ala Leu Leu Ala Phe Thr Leu Gly Val Arg Gln Met Ile Val Gly
1               5                   10                  15

Ile Asn Lys Met Asp Thr Cys Glu Tyr Lys Gln Ser Arg Phe Asp Glu
            20                  25                  30

Ile Phe Asn Glu Val Asp Gly Tyr Leu Lys Lys Val Gly Tyr Asn Thr
        35                  40                  45

Glu Lys Ile Pro Phe Val Ala Ile Ser Gly Phe Val Gly Asp Asn Met
    50                  55                  60

Val Glu Arg Ser Asp Lys Met Pro Trp Tyr Lys Gly Lys Thr Leu Val
65                  70                  75                  80

Glu Ala Leu Asp Thr Met Glu Pro Pro Lys Arg Pro
                85                  90

<210> SEQ ID NO 34
<211> LENGTH: 92
<212> TYPE: PRT
<213> ORGANISM: Plasmodium

<400> SEQUENCE: 34

His Ala Leu Leu Ala Phe Thr Leu Gly Val Lys Gln Ile Val Val Gly
1               5                   10                  15

Val Asn Lys Met Asp Thr Val Lys Tyr Ser Glu Asp Arg Tyr Glu Glu
            20                  25                  30

Ile Lys Lys Glu Val Lys Asp Tyr Leu Lys Lys Val Gly Tyr Gln Ala
        35                  40                  45

Asp Lys Val Asp Phe Ile Pro Ile Ser Gly Phe Glu Gly Asp Asn Leu
    50                  55                  60

Ile Glu Lys Ser Asp Lys Thr Pro Trp Tyr Lys Gly Arg Thr Leu Ile
65                  70                  75                  80

Glu Ala Leu Asp Thr Met Glu Pro Pro Lys Arg Pro
                85                  90

```
<210> SEQ ID NO 35
<211> LENGTH: 94
<212> TYPE: PRT
<213> ORGANISM: Leishmania donova

<400> SEQUENCE: 35

His Ala Leu Leu Ala Phe Thr Leu Gly Val Lys Gln Met Val Val Cys
1               5                   10                  15

Cys Asn Lys Met Asp Asp Lys Thr Val Thr Tyr Ala Gln Ser Arg Tyr
            20                  25                  30

Asp Glu Ile Ser Lys Glu Val Gly Ala Tyr Leu Lys Arg Val Gly Tyr
        35                  40                  45

Asn Pro Glu Lys Val Arg Phe Ile Pro Ile Ser Gly Trp Gln Gly Asp
    50                  55                  60

Asn Met Ile Glu Arg Ser Asp Asn Met Pro Trp Tyr Lys Gly Pro Thr
65                  70                  75                  80

Leu Leu Asp Ala Leu Asp Met Leu Glu Pro Pro Val Arg Pro
                85                  90

<210> SEQ ID NO 36
<211> LENGTH: 92
<212> TYPE: PRT
<213> ORGANISM: Giardia lamblia

<400> SEQUENCE: 36

His Ile Leu Leu Ser Tyr Thr Leu Gly Val Lys Gln Met Ile Val Gly
1               5                   10                  15

Val Asn Lys Met Asp Ala Ile Gln Tyr Lys Gln Glu Arg Tyr Glu Glu
            20                  25                  30

Ile Lys Lys Glu Ile Ser Ala Phe Leu Lys Lys Thr Gly Tyr Asn Pro
        35                  40                  45

Asp Lys Ile Pro Phe Val Pro Ile Ser Gly Phe Gln Gly Asp Asn Met
    50                  55                  60

Ile Glu Pro Ser Thr Asn Met Pro Trp Tyr Lys Gly Pro Thr Leu Ile
65                  70                  75                  80

Gly Ala Leu Asp Ser Val Thr Pro Pro Glu Arg Pro
                85                  90

<210> SEQ ID NO 37
<211> LENGTH: 106
<212> TYPE: PRT
<213> ORGANISM: Homo sapiens

<400> SEQUENCE: 37

His Ala Leu Leu Ala Tyr Thr Leu Gly Val Lys Gln Leu Ile Val Gly
1               5                   10                  15

Val Asn Lys Met Asp Ser Thr Glu Pro Pro Tyr Ser Gln Lys Arg Tyr
            20                  25                  30

Glu Glu Ile Val Lys Glu Val Ser Thr Tyr Ile Lys Lys Ile Gly Tyr
        35                  40                  45

Asn Pro Asp Thr Val Ala Phe Val Pro Ile Ser Gly Trp Asn Gly Asp
    50                  55                  60

Asn Met Leu Glu Pro Ser Ala Asn Met Pro Trp Phe Lys Gly Trp Lys
65                  70                  75                  80

Val Thr Arg Lys Asp Gly Asn Ala Ser Gly Thr Thr Leu Leu Glu Ala
                85                  90                  95

Leu Asp Cys Ile Leu Pro Pro Thr Arg Pro
```

-continued

```
<210> SEQ ID NO 38
<211> LENGTH: 23
<212> TYPE: PRT
<213> ORGANISM: Artificial
<220> FEATURE:
<223> OTHER INFORMATION: Chimeric Indel Peptide

<400> SEQUENCE: 38

Gly Trp Lys Val Thr Arg Lys Asp Gly Asn Ala Ser Gly Asp Arg His
1               5                   10                  15

Asp Ser Gly Leu Asp Ser Met
            20
```

DIAGNOSIS AND TREATMENT OF INFECTIOUS DISEASES THROUGH INDEL-DIFFERENTIATED PROTEINS

FIELD OF INVENTION

The present invention is related to the field of treatment and diagnosis of infectious disease pathogens

BACKGROUND OF THE INVENTION

Despite advances in the treatment, infectious diseases remain a significant factor in worldwide mortality and morbidity. Mortality has risen and the emergence and re-emergence of diseases such as acquired immunodeficiency syndrome, Ebola virus, hantavirus, and tuberculosis demonstrate that the dangers of infectious disease are not static. The role of infectious disease in the etiology of diseases once believed to be non-infectious is only now being recognized. For example, the causative agent of peptic ulcers was only recently discovered to be a bacteria species termed Helicobacter pylori. Medical advances against infectious disease have also been hindered by changes in the patient population. The most susceptible group of individuals to infectious disease are immuno-compromised as a result of immuno-suppressant treatment for organ transplant, individuals undergoing chemotherapy, or most notably those infected by HIV.

The principle agent behind biological weapons is infectious disease. The bacteria Bacillus anthracis has appeared on World Health Organization lists for bioterrorism agents, and it has been reported that 50 kg of the bacillus released up wind of a city of 500,000 would result in over 95,000 fatalities and the incapacitation of 125,000 individuals. Smallpox, Yersinia pestis (plague), Francisella tularensis (tularemia), and viral hemorrhagic agents such as Ebola and Marburg viruses are also potential biological weapons.

While treatment for many infectious diseases does exist, rapid and simple diagnostics are needed in order to avoid death or significant complications. Unfortunately the majority of detection methods rely on microscopic visualization and culturing of the pathogen in order to obtain enough phenotypic data to differentially diagnose the infectious disease. These methods are imprecise, time consuming, and rely on highly-trained laboratory personnel. Other methods and systems that exist for diagnosis of some pathogens include: biological signals (unique or toxic components of a microorganism are differentiated from the normal physical environment); detection systems (used to sense a signal and discriminate between the signal and background noise; a detector can range from a trained set of eyes to sensitive electronic instruments designed to detect immunofluorescence, chemiluminescence, light absorbance, flame ionization detection, etc); and, amplification (techniques include polymerase chain reaction, which is able to detect and amplify sufficient unique pathogen DNA or RNA to allow for sensitive analysis and discrimination).

By way of example, protozoan pathogens are responsible for a wide variety of infectious diseases, typically tropical in nature. These pathogens exist as intracellular parasites in a host and include organisms that appear to be protozoan in nature such as Pneumocystis. An example of such protozoan pathogens is the genus Leishmania, which causes a spectrum of tropical and subtropical diseases known as the leishmaniases. Leishmania live as either extracellular, flagellated promastigotes in the digestive tract of their sand fly vector or as non-flagellated amastigotes within macrophages, where they survive and replicate within phagolysosomes. During both the innate and acquired immune responses, macrophages respond to extracellular signals to become activated for enhanced antimicrobial activity. This is a critical step in elimination of intracellular pathogens by the host. However, leishmania and other intracellular pathogens have developed mechanisms to interfere with cell signaling pathways, thereby preventing macrophages from becoming effectively activated [1;2]. As a result, these organisms are able to survive and successfully multiply within the otherwise hostile intracellular milieu of macrophages.

L. donovani is the major causative agent of human visceral leishmaniasis. This disease is progressive and often fatal if untreated. Macrophages infected with L. donovani show a phenotype of impaired cell signaling and cell deactivation. For example, interferon-□ signaling through the Jak-Stat1 pathway [3] and mitogen-activated protein kinase signaling leading to iNOS induction and c-FOS expression are attenuated in leishmania infected cells [4]. This phenotype is reversed in cells that are incubated with the protein tyrosine phosphatase (PTP) inhibitor sodium orthovandate prior to infection [4]. The Src-homology 2 (SH2) domain containing protein tyrosine phosphatase-1 (SHP-1) appears to be involved in the pathogenesis of leishmania infections [4-7]. In particular, SHP-1 has been shown to become activated in leishmania infected cells [4;6] and leishmania infection is attenuated under conditions of SHP-1 deficiency [7]. Moreover, it has recently been shown that the conventional anti-leishmanial agent used (sodium stibogluconate) is an inhibitor of SHP-1 [8].

SUMMARY OF THE INVENTION

Until this invention, conserved proteins were not viewed as markers for infectious diseases or as therapeutic targets. Assays for the conserved protein would be expected to reveal the presence of host protein as a false positive result. Since conserved proteins are usually essential to both host and pathogen, targeting a conserved protein with a therapeutic agent would be expected to be deleterious to the host. An example of such a protein is elongation factor alpha (EF-1α). EF-1α is a conserved protein in all cells, whether eukaryotic or prokaryotic, whose function involves the assembly of polypeptides from amino acids based upon the translation of mRNA by ribosomes. EF-1α, or close homologue, shepards amino-acyl-tRNA molecules to the ribosomal complex attached to an mRNA strand, where the amino-acyl-tRNA is loaded onto the ribosome A-site following hydrolysis of GTP to GDP by EF-1α. Without EF1-α, protein synthesis ceases, as does cell viability. The basis of this invention involves the detection or identification of indel (insertion/deletion) sequences between otherwise conserved proteins present both in host and in infectious pathogens. An indel is defined herein as an insertion or deletion of 4 or more consecutive amino acids. As an insertion, an indel may form a secondary or tertiary structure upon protein folding and thereby may overly in whole or in part a region of the protein that is termed herein an "indel complementarity region". The indel complementarity region is exposed on a homologous conserved protein that lacks the insertion. Thus there exists between conserved proteins with noted indels, regions that are differentially displayed between host and pathogen that serve as the basis for diagnostic testing and treatment of a particular infectious disease.

For purposes of this invention, an infectious pathogen is an organism that infects a host and a host is an organism that an infectious pathogen is capable of infecting. Such pathogens include parasites and disease causing microorganism pathogens such as protozoa, bacteria, fungi and viruses. Hosts include higher organisms infected by such pathogens (including plants and animals), and of particular importance in the use of this invention are mammalian hosts, including humans.

Conserved proteins for purposes of this invention have at least 70% sequence identity as determined by suitable algorithms, including BLAST (National Center for Biotechnology Information, www.ncbi.nlm.nih.gov). Preferably, conserved proteins for the purposes of this invention have greater than 70% sequence identity and more preferably, will exhibit sequence identity equivalent to or approximately equivalent to any integer from 71-99. Examples of preferred sequence identities between conserved proteins, generally from least to more preferable are: about 75, about 80, about 85, about 90 and greater than 90%.

BRIEF DESCRIPTION OF THE DRAWINGS

FIG. 1A. Multiple Alignment of peptide sequence of the EF-1α (EF) from *L. donovani* (*L. don*) [Accession #AF416379]; *L. brazileinsis* (*L. braz*) [Accession #U72244]; *Trypanosome brucei* (*T. bruc*) [Accession #P41166]; and *Homo sapiens* [Accession # P04720]. The human sequence contains 12 extra amino acids compared with the EF-1α from trypanosomatids (capital letters in box). Important amino acid changes between human EF-1α and EF-1α from the trypanosomatids (bold letters and highlighted in gray), include the replacement of glycine and valine in human EF-1α at positions 151 and 152 with two cysteines in each trypanosomatid EF-1α. Two ITIM motifs, sites for binding to SH2-domain-containing proteins are shown in bold and italic letters. Motifs typical of GTP binding proteins are underlined and sites of post-translational modification are shown bold with larger font.

FIG. 1B. Multiple alignment of partial EF-1α peptide sequences from different protozoan sources. This drawing demonstrates high degree of homology (no less than 70%) between EF-1α proteins from divergent origins. The symbol (*) indicates identical amino acids. The symbol (~) indicates amino acids with similar properties. The last line of the drawing sets out an aligned human partial sequence and the location of the indel sequence following amino acid 212 present in the human but not in the protozoan protein. The following are the species and accession numbers for the protozoan sources referred to in the Figure:

D14342 *Giardia lamblia*
AF416379 *Leishmania donova*
AJ224154 *Plasmodium*
U71180 *Cryptosporidium parvum*
L76077 *Trypanosoma cruzi*
M92073 *Entamoeba histolytica*

Figure 2:
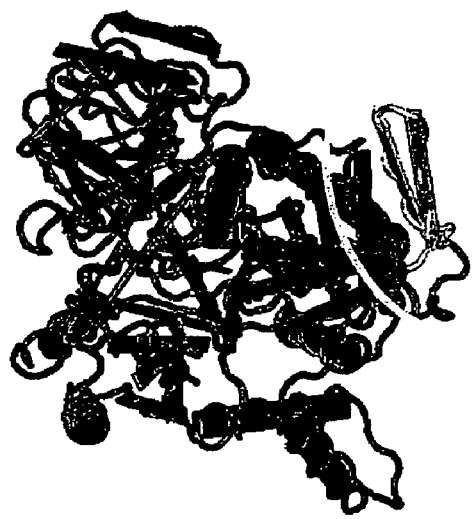
Figure 2:

FIG. 2. Molecular modeling of human and pathogen EF-1α. Modeling of the structure of *leishmania* EF-1α was done using the SwissPDB Viewer™ package (11) combined with the Molecular Operation Environment (MOE™) software package (Version 2001.01, Chemical Computing Group, Inc., Montreal, Canada) as described below. Homology templates used for modeling were retrieved from the Expasy™ server (www.expasy.ch). Shown are structures for EF-1α from human (A) and *L. donovani* (B) with location of indel (hairpin insert) indicated in an oval for (A) and the indel complementarity region for (B).

Figure 3:
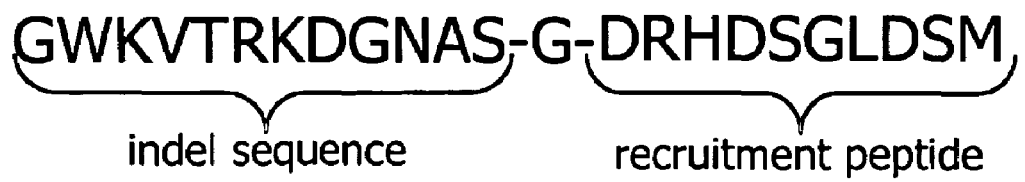

FIG. 3. Peptide sequence of chimeric indel. The "indel" portion is for selective binding to pathogenic EF-1α protein and is based on SEQ ID NO:26. The "recruitment" position is for ubiquitination.

DETAILED DESCRIPTION OF THE INVENTION

This invention includes methods for detecting, characterizing, testing, or assaying moieties for specific binding to indel differentiated proteins. This includes methods for determining whether a putative specific binding moiety binds to a pathogenic homologue, but not to a host homologue. This may be done in vitro or by computer implemented modeling. For example, a first three-dimensional model of a pathogenic indel differentiated protein or part of the protein representing an indel complementarity region (should the indel be a deletion) or the indel itself (should it be present as an insertion), and a second three-dimensional model of a putative specific binding moiety may be used whereby positioning both three-dimensional models to form a third three-dimensional model of a specific binding complex may be performed allowing one to determine whether a binding complex is favourable (for example, without unacceptable hindrances such as steric, electrostatic, and hydrophobic hindrances). The latter method may also be used for designing a specific binding moiety for pathogenic indel differentiated proteins whereby a three-dimensional model of a putative specific binding moiety is altered to optimize binding between said moiety and said indel differentiated protein.

This invention also includes moieties capable of specific binding to pathogenic indel differentiated proteins and complexes of such moieties with a pathogenic protein. By "specific binding" it is meant that the moiety is capable of preferentially binding to a pathogenic indel differentiated protein, and not to a host homologue. Preferably such a moiety will exhibit substantially or essentially no binding to the host homologue. Specific binding moieties of this invention may be chemical moieties designed to bind with contact residues in the indel complementarity region, or the indel itself, depending on the presence or absence of the indel on the identified pathogenic indel differentiated protein. Such moieties may be peptides or non-peptide molecules. Such moieties may be antibodies or antibody fragments capable of binding to the antigenic determinant of an indel complementarity region or the indel itself, depending on the presence or absence of the indel on the identified pathogenic indel differentiated protein.

Compounds of this invention may bind specifically to an indel complementarity region on a pathogen protein and disrupt its function, particularly a virulence function, without interfering with essential function of a host homologue. Such compounds are useful as therapeutics. In addition, compounds that bind to a pathogen homologue, but not to a host homologue can be used for diagnostic tests. Such therapeutic and diagnostic compounds include antibodies, peptides, proteins and small molecule compounds.

This invention also includes diagnostic systems which may include a detection system that is able to amplify a signal from a small number of pathogens to an observable threshold. An example could be, but not limited to, an enzyme linked immunological sandwich assay (ELISA) whereby homologous proteins are bound to a fixed, non-differentiated antibody, and a second indel differentiated antibody detects the presence of the pathogen, indel differentiated protein. The indel differentiated diagnostic test could also be based on a variety of proteomic assays such as, but not limited to, protein chips, substrate assays (enzyme attached to binding moiety that converts substrate to detectable compound), or purification.

The invention provides methods of characterizing indel differentiated proteins between pathogen and host, which proteins are otherwise conserved and share a high degree of homology. In pathogen indel differentiated proteins lacking an indel, the indel complementarity region is targeted for development of a moiety that displays specific binding to that region. In pathogen indel differentiated proteins containing an indel, the indel itself is targeted for development of a moiety that displays specific binding to that region. Such moieties are useful as diagnostic and therapeutic compounds and in the making of such compounds.

By way of example, a pathogenic form of EF-1α from protozoan sources is characterized herein. Host (e.g. human) EF-1α contains a 12 amino acid insertion upon its surface, whereas EF-1α from pathogens does not. The pathogen EF-1α contains an indel complementarity region which is otherwise covered or masked by the insertion in host EF-1α. Thus there is a significant region of differentially exposed amino acids in the pathogen protein in comparison to the human protein. Based upon the results shown in the Examples below, and the known phylogeny of protozoan and protozoan-like organisms, pathogens that lack the aforementioned indel in EF-1α include: *leishmania* (agent of leishmaniasis), *Trypanosoma brucei* and *Trypanosoma cruzi* (respective agents of sleeping sickness and Chagas disease), *cryptosporidium* (agent of cryptosporidiosis), *entamoeba* (agent of amebiasis), *Giardia* (agent of giardiasis), *plasmodium* (agent of malaria), *Toxoplasma gondi* (agent of toxoplasma), and *Pneumocystitis carinis* (an agent of pneumocystitus).

Pathogen EF-1α is now shown to play at least two essential roles, these being the regulation of protein synthesis and as a virulence factor. A virulence factor renders a host cell permissive for infection and may possess one or more of the following: a component of a pathogen that when deleted specifically impairs virulence but not viability; a microbial product that permits a pathogen to cause disease; a component of a pathogen that damages the host; or an effector molecule that 1) produces changes in target cells outside of the organism itself, 2) is found only in pathogenic species or variety of the organism, and 3) is located on the surface of the organism or is secreted by the organism.

The 12 amino acid EF-1α indel forms a hairpin loop structure on the surface of the human homologue that is closely opposed to the main-body of the protein and is further stabilized by ionic interactions between several highly charged amino acids residues on both the indel and the main body. The indel complementarity region comprises the highly charged amino acids on the main body of the pathogen EF-1α protein, which is otherwise concealed in host cells by the presence of the indel. This region is a unique specific site to which binding moieties will bind to pathogen EF-1α, but not the corresponding host EF-1α homologue. Such specific binding moieties include antibodies, antibody fragments, peptides, proteins and small molecule compounds.

This invention includes methods for identifying, detecting, characterizing, testing or assaying EF-1α proteins which include determining whether a protein having homology to EF-1α binds SHP-1; or, determining whether such an EF-1α protein comprises an EF-1α indel as described herein, including an indel having 70, 75, 80, 85, 90, or greater than 90% sequence identity to the human EF-1α indel described herein, or forms a structure such as an anti-parallel β structure (including a hairpin loop) that shields an indel complementarity region, wherein absence of such an indel is indicative of pathogenicity. These methods may be performed, for example, by assaying for SHP-1 binding and/or activation as described herein, or by sequencing (actual or predicted) and comparison of such sequence to pathogenic EF-1α sequences, including those pathogenic sequences disclosed herein from protozoa.

This invention includes methods for identifying, detecting, testing or assaying moieties for specific binding to pathogenic EF-1α or an ability to modulate the activity of pathogenic EF-1α, which methods include determining whether a putative specific binding moiety binds to a pathogenic EF-1α and not to human EF-1α (or binds to said pathogenic EF-1α to a greater extent than the human form); or, utilizing a first three-dimensional model of a pathogenic EF-1α indel complementarity region and a second three-dimensional model of a putative specific binding moiety, positioning both said three-dimensional models to form a third three-dimensional model of a specific binding complex and determining whether said binding complex is favourable (for example, without unacceptable hindrances such as steric, electrostatic, and hydrophobic hindrances). The latter methods may also be used for designing a specific binding moiety for pathogenic EF-1α wherein a three-dimensional model of a putative specific binding moiety is altered to optimize binding between said moiety and said indel complementarity region. The indel complementarity region may comprise regions of contiguous amino acids from the following regions of *leishmania* EF-1α or from corresponding (homologous) regions of another pathogenic EF-1α (for example, as shown in FIG. 1). Examples of regions of contiguous amino acids from indel complementarity regions of the pathogens shown in FIG. 1 are as follows.

*Leishmania donavi* (accession AAL08019, gi:15788964)

| amino acids 215-224 | TLLDALDMLE | (SEQ ID NO: 1) |
| amino acids 186-194 | EKVRFIPIS | (SEQ ID NO: 2) |
| amino acids 158-168 | KTVTYAQSRYD | (SEQ ID NO: 3) |

*Trypanosoma cruzi* (accession JC5117, gi:2133383) or *Trypanosoma brucei*

| amino acids 215-224 | TLLEALDMLE | (SEQ ID NO: 4) |
| amino acids 186-194 | EKVRFIPIS | (SEQ ID NO: 5) |
| amino acids 158-168 | KSVNFAQERYD | (SEQ ID NO: 6) |

*Cryptosporidium parvum* (accession AAC47526, gi:1737177)

| amino acids 211-221 | TLVEALDTMEP | (SEQ ID NO: 7) |
| amino acids 182-190 | EKIPFVAIS | (SEQ ID NO: 8) |
| amino acids 154-164 | DTCEYKQSRFD | (SEQ ID NO: 9) |

*Plasmodium flaciparum* (accession CAD52691, gi:23615699)

| amino acids 213-222 | TLIEALDTME | (SEQ ID NO: 10) |
| amino acids 184-192 | DKVDFIPIS | (SEQ ID NO: 11) |
| amino acids 156-166 | DTVKYSEDRYE | (SEQ ID NO: 12) |

*Entamoeba histolytica* (accession AAA29096, gi:158939)

```
amino acids 213-222    TLIGALDSVT    (SEQ ID NO: 13)

amino acids 184-192    DKIPFVPIS     (SEQ ID NO: 14)

amino acids 156-166    DAIQYKQERYE   (SEQ ID NO: 15)
```

*Giardia intestinalis* (accession BAA03276, gi:285802)

```
amino acids 196-205    CLIDAIDGLK    (SEQ ID NO: 16)

amino acids 167-175    EEFDYIPTS     (SEQ ID NO: 17)

amino acids 138-148    GQVKYSKERYD   (SEQ ID NO: 18)
```

The specific binding moiety may be capable of binding with, or such binding may be optimized to occur with one or more contact residues such as any of the following amino acids from the *leishmania* EF-1α indel complementarity region, or a similarly placed charged or polar amino acid from another pathogenic EF-1α indel complementarity region.

Glutamate (E) 186
Lysine (K) 187
Arginine (R) 189
Aspartate (D) 218
Aspartate (D) 221
Methionine (M) 222
Glutamate (E) 224

The aforementioned methods may additionally comprise one or more of: synthesizing a specific binding moiety, and combining a specific binding moiety with a pathogenic indel differentiated protein. These methods may further comprise methods of detecting, characterizing, testing or assaying binding of a moiety to a pathogen protein.

This invention also includes moieties capable of specific binding to pathogen EF-1α, including those described in the Examples. The moieties are capable of preferentially binding to pathogen EF-1α as compared to human EF-1α. Preferably, such a moiety will exhibit substantially no binding to human EF-1α. Such binding moieties may be employed in assays for EF-1α and as specific targeting ligands (e.g. for labeling or directing a further moiety to the location of EF-1α). In some embodiments, such moieties modulate an activity of EF-1α, including the activity of pathogen EF-1α in protein translation in the pathogen; activity as a pathogen virulence factor, and/or binding or activation of SHP-1. Specific binding moieties of this invention may be chemical moieties designed to bind with contact residues in the indel complementarity region as defined herein. Such moieties may be peptides or non-peptide molecules. Such moieties may be antibodies or antibody fragments capable of binding to an antigenic determinant of an indel complementarity region. In addition, specific binding moieties of this invention may shield the indel complementarity region without directly binding to said region. Specific binding moieties of this invention include therapeutic moieties for treatment of infections by organisms possessing pathogenic EF-1α, in particular protozoan organisms. Accordingly, this invention includes the use of such therapeutic moieties in treatment and provides pharmaceutical compositions and formulations comprising specific binding moieties of this invention together with one or more acceptable pharmaceutical carriers.

This invention also includes methods for modulating the activity a pathogen protein as defined herein comprising contacting the protein with a specific binding moiety capable of modulating a function of the protein but not the host homologue. The contacting may be done by expressing the binding moiety in a cell through use of a recombinant expression vector. Preferably, said modulation comprises antagonism of a pathogenic activity, including one or more of: pathogen protein translation, pathogenic virulence, SHP-1 binding and/or activation.

The "unshielded" indel complementarity region of pathogen EF-1α, which is concealed by a hairpin loop in the human protein, contains several highly polar residues with exposed side chains. Small molecules and peptides may be designed (using conventional modeling techniques and available software) to specifically bind to this unshielded region. Such a specific binding moiety will have a binding site containing one or more binding elements, which may be one or more chemical groups capable of forming a hydrogen or ionic bond or participate in a hydrophobic interaction with one or more contact residues in the unshielded region of EF-1α. Preferably, two or more such bonds and/or interactions will exist. The aforementioned bonds may exist between a group on the specific binding moiety and atoms in the polypeptide backbone or in an amino acid side chain at the unshielded region, in the presence of or the absence of water molecules between the binding moiety and the unshielded region. Preferably, the distance between a binding element in the moiety and a contact residue will be 5 Angstroms or less, more preferably from 1-4 or from 2-3 Angstroms. Preferably, a contact residue will be selected from one or more amino acids in the unshielded region, capable of forming a hydrogen bond or which have polar side chains, such as amino acids corresponding to one or more of $Asp^{218\ or\ 221}$, $Glu^{186\ or\ 224}$, $Met^{222}$, $Lys^{187}$ and $Arg^{189}$ of *leishmania* EF-1α. The specific binding moiety may have the capacity of binding other regions of EF-1α by hydrophobic or polar interactions, particularly with the regions corresponding to amino acids 182-191 and 226-236 of yeast EF-1α (such as $Leu^{184}$) or amino acids 158-168, 186-194, and 215-224 of *leishmania* EF-1α. The atomic coordinates of EF-1α as set out in Table 4 below may be used to design the three-dimensional shape and thus composition of the specific binding moiety. A formation of binding of such a moiety to the unshielded region of pathogenic EF-1α may be construed by computer modeling or by x-ray crystallography of EF-1α with and without the bound moiety (e.g. see: U.S. Pat. Nos. 6,127,524 and 6,168,928).

In addition to small molecules/peptides, specific binding moieties according to this invention may be antibodies or antibody fragments including single chain antibodies, specific for the unshielded region of pathogen EF-1α or which otherwise specifically bind to the pathogen form. Antibodies and antibody fragments may be generated by well known techniques, including those exemplified herein.

The specific binding moieties described above may cause a change in function of pathogenic EF-1α (e.g. by affecting SHP-1 binding or by affecting EF-1α's role in protein translation) or the moiety may simply bind with specificity to the pathogenic form. In the latter instance, the moiety may be used as a targeting ligand in assays for the label or pathogenic form (e.g. with a radiolabel or other moiety which facilitates detection) or as a targeting ligand for therapeutic moieties that themselves bring about an affect on the pathogenic protein. In the case of a moiety that binds but does not inhibit the protein synthesis function or the virulence factor properties of EF-1α, alternative strategies may be used to therapeutically target the pathogen. An example is the use of intracellular trafficking to destroy the pathogen EF-1α protein. A specific example of such a strategy is one which utilizes aspects of the ubiquitin pathway responsible for the majority of protein turnover within a eukaryotic cell.

Typically ubiquitin is ligated to proteins targeted for destruction and serves as a marker for transport to lysosomes and subsequent proteolysis. Both strategies take advantage of the capacity of a synthetic indel peptide based upon the human EF-1α sequence to selectively bind the exposed epitopes available on the surface of *leishmania* EF-1α, but not on the human protein. The synthetic indel could contain either a terminal signal for ubiquitination or the protein sequence for ubiquitin. One of the ubiquitination complexes that has been well characterized governs the turnover of IκBα, the inhibitor of NFκB. NFκB controls expression of many genes associated with inflammation. The protein IκBα is recruited to the ubiquitination complex by virtue of a 10 amino acid sequence (hereafter referred to as 'recruitment peptide') that is phosphorylated in response to inflammatory signals [32]. Thus, at the onset of inflammation upon infection, the inhibitor to inflammatory gene expression is destroyed, and upregulation of NF-κB controlled genes expression occurs and the recruitment peptide is activated. The recruitment peptide may be added onto the C-terminal of a specific binding moiety as described above which may be the actual 12 amino acid indel, joined by an amino acid to the recruitment peptide (see FIG. 3). The chimeric indel may be delivered to *leishmania* infected macrophages using either liposomes or a protein targeting reagent such as Profect-1™. *Leishmania* viability in macrophages may be monitored and compared to control treated cells (introduction of an irrelevant peptide sequence of identical size and linked to the recruitment peptide).

An alternative strategy uses expression of a recombinant peptide comprised of an N-terminal ubiquitin sequence and a C-terminal indel peptide. The C-terminal sequence of ubiquitin may be mutated from a glycine to an alanine to prevent cleavage of the ubiquitin protein [33]. The cDNA for human ubiquitin may be amplified by PCR from a human cDNA library using specific 5' and 3' oligonucleotide primers to facilitate cloning of the ubiquitin gene into the prokaryotic expression vector pBlueBac4.5/V5-His Transfer Vector (Invitrogen), permitting expression in an insect cell line. The 3' oligonucleotide will contain the appropriate mutation to convert the glycine$^{76}$ codon to alanine. The nucleic acid coding sequence for the indel may be synthesized as two complementary oligonucleotides and ligated in frame with the ubiquitin gene to allow for expression of a recombinant ubiquitin-indel protein. Purified ubiquitin-indel protein may be delivered to *leishmania* infected macrophages as described above for chimeric proteins, followed by assessment of parasite survival.

Pure EF-1α may be expressed in a recombinant baculovirus system and purified by affinity chromatography. A full length *L. donovani* EF-1α gene may be PCR amplified using oligonucleotide primers, which contain restriction endonuclease sites to facilitate ligation into a baculovirus expression vector. A baculovirus system is preferable over prokaryotic expression systems [42] since EF-1α protein appears to undergo post-translational modifications, including methylation of lysine residues and glycerolphosphoryl-ethanolamine additions, not possible in bacteria. Human EF-1α may also be cloned, expressed, and purified using this methodology. By way of example, *L. donovani* EF-1α-EK-His coding sequence may be sub-cloned into the pBlueBac4.5™ expression vector (Invitrogen) and cotransfected with the Bac-N-Blue vector (Invitrogen) into Sf9 insect cells and the viral supernatant harvested at day three. Plaque assays may be performed to isolate pure virus that will be screened by PCR to identify recombinant virus. High titer virus stocks will be prepared and used to infect Sf9 insect cells for high level expression of *L. donovani* EF-1α [42]. Cell lysates may be prepared and the rEF-1α purified by affinity chromatography using ProBond columns (Invitrogen). After elution, rEF-1α may be treated with enterokinase (enteropeptidase) (New England Biolabs) to remove the His tag, purified by FPLC gel exclusion chromatography and used for functional analysis. Affinity purified, baculovirus-expressed EF-1α may be incubated with GST-SHP-1 to examine its ability to bind to and activate the enzyme by phosphatase assay as described above. Synthetic phosphopeptides derived from the primary sequence of the two ITIMs of EF-1α, including five amino acids on either side of each, may be biotin conjugated and used to bind to and activate SHP-1 in vitro. These peptides may be compared with peptides in which tyrosine has been replaced by phenylalanine. The peptides may also be employed to compete with full length EF-1α for binding to SHP-1. PCR-based, site-directed mutagenesis [42] may be used to produce full length protein in which either one or both tyrosines have been changed to phenylalanine to abolish SHP-1 binding.

Crystals of *leishmania* and human EF-1α may be grown following known protocols for yeast EF-1α crystallization. Crystals of *leishmania* and human EF-1α may be grown by the hanging drop method, for example by combining equal volumes (2 μl) of the protein stock and mother liquor (e.g. 20% polyethylene glycol 8000, 0.1 M cacodylate, pH 6.5) at room temperature. Crystals may be subjected to vitrification in 30% polyethylene glycol 8000, 0.1 M cacodylate, pH 6.5 and 15% glycerol using liquid propane. Diffraction data may be collected, for example by using a Mar345 Image Plate detector with osmic mirrors mounted on a Rigaku RU-200 rotating anode x-ray generator. Data may be processed using HKL programs. Molecular replacement may be performed using CCP4 software, and subsequent refinement of the model may be done using the CNS program. An alternative expression system for the synthesis of recombinant proteins in *leishmania* may also be used [34-37], followed by purification and x-ray crystallography.

Bioinformatic programs [38-41] may be used to screen the conformations of known small molecules for potential fit within a pathogen indel or indel complementarity region such as that of *leishmania* EF-1α. In addition, potential binding moieties may be incubated in solution with EF-1α protein crystals, and the complementarity region once more defined by crystallography to determine fit of the therapeutic molecule.

EXAMPLES

Detection and Characterization of Pathogen and Host Indel-Differentiated Proteins

Reagents, Chemicals and Cell Lines

RPMI 1640, Hanks balanced salt solution (HBSS) and protease inhibitors (phenylmethylsulfonyl fluoride, aprotinin, pepstatin A, and leupeptin) and calmodulin-agarose were obtained from Sigma Chemical Co. (St. Louis, Mo.). Medium 199 was from Gibco-BRL (Grand Island, N.Y.). The RAW 264.7 cell line was from the American Type Culture Collection (Rockville, Md.). Horseradish peroxidase-conjugated goat anti-mouse antibodies, protein G-agarose and electrophoresis reagents and supplies were from Bio-Rad (Hercules, Calif.). Enhanced chemiluminescence (ECL) reagents were from Amersham International (Oakville. Ontario, Canada). Preparation of the GST-SHP-1 construct, its expression and purification has previously been described [9]. Pre-treatment sera from visceral leishmaniasis patients were kindly provided by Clarisa Palatnik-de-Souza and Cristina Vidal Pessolani, Laboratorio de Hanseniase, Instituto Osvaldo Cruz, Fundacao Oswaldo Cruz (FIOCRUZ), Rio de Janeiro, Brazil. Total cell lysates of *Trypanosoma brucei brucei*, *Trypanosoma congolense* and *Trypanosoma cruzi* were provided by T. W Pearson, Department of Biochemistry, University of Victoria, Victoria, BC, Canada.

*L. donovani*

Amastigotes of the Sudan strain 2S of *L. donovani* were maintained by serial intra-cardiac inoculation of amastigotes into female Syrian hamsters. Amastigotes were isolated from the spleens of hamsters infected four to six weeks earlier as described previously [10]. Promastigotes were prepared by culture at room temperature of freshly isolated, spleen derived amastigotes in medium 199 supplemented with 10% (v/v) heat-inactivated fetal bovine serum, penicillin (100 U/ml), streptomycin (100 µg/ml), adenosine (1 mM), folic acid (10 µg/ml) and hemin (6 µg/ml). Promastigotes were maintained in the laboratory by transferring every third day in medium 199 containing supplements as described above. Organisms in stationary growth phase (day five containing approximately $50\times10^6$ per ml) were used.

Cell Culture

The murine macrophage cell line RAW 264.7 was cultured in RPMI 1640 medium supplemented with 10% heat-inactivated fetal bovine serum, penicillin (100 U/ml) and streptomycin (100 µg/ml) at 37° C. in a humidified atmosphere (5% $CO_2$).

Cloning of *L. donovani* EF-1α cDNA

Total RNA was isolated from stationary phase *L. donovani* promastigotes using TRIzol™ reagent (Gibco-BRL) according to the manufacturer's instructions followed by treatment with RNase free DNase. Five micrograms of total RNA was reverse transcribed into cDNA with Maloney murine leukemia virus reverse transcriptase (Gibco-BRL) and oligo d(T)$_8$ primers. PCR was used to amplify EF-1α from total cDNA. Sequences of oligonucleotide primers used in PCR amplifications were as follows: sense, 5'-ACCATGGGCAAG-GATAAGGTG-3' (*L. braziliensis*) SEQ ID NO:19; and antisense 5'-CTTCTTCGCAGCCTTCG-3' (*L. braziliensis*) SEQ ID NO:20. Thirty cycles were run for 1 min each at 94° C., 1 min at 55° C., and 3 min at 72° C. followed by a 10 min extension at 72° C. Upon completion of the amplification, the PCR product was analyzed by ethidium bromide staining in agarose gels. The product of correct size was sub-cloned into a TA™ cloning vector (Invitrogen Corporation, Carlsbad, Calif.) according to the manufacturer's instructions. Plasmids from three independent clones were sequenced (DNA Sequencing Laboratory, University of British Columbia, Canada).

Infection of RAW Cells with *L. donovani*

Exponentially growing RAW 264.7 cells were infected with either stationary phase promastigotes or freshly isolated amastigotes at parasite-to-cell ratios of approximately 10:1. After incubation at 37° C. for two hours, non-internalized parasites were removed by washing with HBSS. To determine the rate of infection, cytospin preparations were prepared from dislodged cells and stained with Diff-Quik™.

Immunoprecipitation and Immunoblotting.

*L. donovani* promastigotes in stationary phase were collected by centrifugation and washed twice with Tris-buffered saline, pH 7.4 and immediately processed for immunoprecipitation. For immunoprecipitation of EF-1α, parasites were lysed on ice in lysis buffer [50 mM Tris (pH 7.4), 1% Triton X-100™, 0.15 M NaCl, 1 mM EGTA, 5 mM NaF, 1 mM sodium orthovanadate, 1 mM phenylmethylsulfonylfluoride, 10 µg aprotinin/ml, 10 µg leupeptin/ml, and 2 µg of pepstatin A/ml]. Cell lysates were clarified by centrifugation in a microcentrifuge at maximum speed for 20 min at 4° C. The resulting supernatants were incubated with anti-EF-1α antibodies for 16 to 18 h at 4° C. Protein G-agarose was then added for 2 h at 4° C. for recovery of immune complexes. After extensive washing, immune complexes were released by boiling agarose beads in SDS-sample buffer without β-mercaptoethanol. Samples were analyzed by 7.5% SDS-polyacrylamide gel electrophoresis and electroblotted onto nitrocellulose membranes. The membranes were blocked with 3% non-fat dry milk in phosphate buffered saline followed by incubation with anti-EF-1α antibodies. After washing, the blots were incubated with anti-mouse horseradish peroxidase-conjugated antibody and developed using the ECL detection system.

Cell Fractionation.

Stationary phase *L. donovani* promastigotes were collected by centrifugation and washed with Tris-buffered saline, resuspended in hypotonic fractionation buffer [10 mM Tris (pH 7.4), 1 mM sodium orthovanadate, 5 mM NaF, 1 mM phenylmethylsulfonylfluoride, 10 µg of aprotinin/ml, 10 µg of leupeptin/ml, and 2 µg of pepstatin A/ml] and lysed by sonication. For RAW cell fractionation, exponentially growing cells were washed with HBSS and scraped into hypotonic buffer and lysed by sonication. Lysates were then centrifuged at 100,000×g at 4° C. for 20 min to separate cytosolic from particulate fractions. The resulting pellets were extracted in fractionation buffer containing 1% Triton X-100™ and 0.15 mM NaCl at 4° C. for 20 min while rotating. Suspensions were then centrifuged (100,000×g, 20 min, 4° C.) to separate Triton-soluble and insoluble material. The Triton-insoluble pellet was extracted in 2×SDS-sample buffer.

Purification of EF-1α.

Exponentially growing RAW264.7 cells or stationary phase *leishmania* promastigotes were washed in Hanks balanced salt solution and collected in ice cold buffer B [50 mM Tris (pH 7.5), 1 mM EDTA, 1 mM DTT and 20% glycerol] containing 50 mM KCl and a cocktail of protease and phosphatase inhibitors. Cells were sonicated to prepare lysates and centrifuged at 100,000×g for 20 min at 4° C. The supernatants were applied to DEAE-Sepharose columns connected to CM-Sepharose columns previously equilibrated in buffer B containing 50 mM KCl. The columns were washed with equilibration buffer until all non-bound proteins had eluted. After disconnection of the CM-Sepharose columns, bound proteins on these columns were eluted with increasing concentrations of KCl in buffer B. The fractions containing EF-1α as analyzed by SDS-PAGE and immunoblotting using anti-EF-1α antibodies were pooled and dialyzed overnight against buffer B without KCl. The pooled samples were applied to phosphocellulose columns and bound proteins were eluted with increasing concentrations of KCl in buffer B. The fractions were analysed for the presence of EF-1α by separation on SDS-PAGE followed by immunoblotting using anti-EF-1α antibodies. The fractions containing near homogeneous EF-1α (as judged by silver staining) were pooled and dialyzed overnight against buffer B.

Identification of the 56 kDa SHP-1 Binding Protein as EF-1α.

Pomastigotes ($2-3\times10^9$) were lysed in ice cold lysis buffer A (50 mM Tris [pH 7.5], 0.5% Triton X-100™ and 20 mM NaCl) containing a cocktail of protease inhibitors for 20 min on ice. All subsequent steps were performed at 4° C. Lysates were centrifuged in a microcentrifuge at maximum speed for 10 min and supernatants were incubated with GST-SHP-1 affinity beads with end-over-end rotation for 2 hr. [9]. After incubation, affinity beads were transferred to a column and washed extensively. Bound proteins were released with buffer A containing 0.5 M NaCl. An aliquot of partially purified SHP-1 bound proteins was subjected to SDS-PAGE (12%) followed by silver staining. Positions of SHP-1 binding proteins were determined to be about 56 kDa and about 44 kDa. An aliquot of GST-SHP-1 binding proteins, 50 µg of total detergent promastigote lysate and 50 µg of total lysate from the human carcinoma line A431 were separated on SDS-PAGE, transferred to nitrocellulose and probed with anti-EF-1α. Affinity chromatography of *leishmania* lysates using GST-SHP-1 coupled to glutathione-sepharose showed two prominent proteins of approximate subunit size 56 and 44 kDa specifically bound to GST-SHP-1. A parallel affinity column consisting of GST-glutathione-sepharose, showed no detectable binding proteins. The 56 kDa silver stained band was excised for sequencing and tryptic peptide digests were analyzed by mass spectrometry. Eight of the peptides were found to match elongation factor 1-alpha of *Leishmania braziliensis* (NCBInr accession number 5834626) and covered 16.2% of the sequence. An antibody to EF-1α detected single bands of identical size in both the total *leishmania* lysate applied to the column and in the GST-SHP-1 affinity column eluate, thus confirming the internal protein sequence data indicating that the 56 kDa SHP-1 binding protein band contained EF-1α. This shows that *leishmania* EF-1α is a SHP-1 binding protein.

In Vivo Association of *leishmania* EF-1α with Host-SHP-1.

*Leishmania* promastigotes were washed three times with excess of buffer D (20 mM HEPES (pH 7.2) containing 0.15 M NaCl) to remove serum proteins. Washed promastigotes ($5 \times 10^8$/ml) were resuspended in buffer D containing 10 µg/ml soybean trypsin inhibitor and incubated for 4 hr. To detect the presence of EF-1α, the concentrated culture medium was separated on SDS-PAGE, transferred to a nitrocellulose membrane and probed with anti-EF-1α for immunoreactivity with antiphosphotyrosine antibody 4G10, and for SHP-1 activator activity by pNPP assay. Macrophages were infected with promastigotes for 14-16 hrs. Cytosolic fractions were then prepared from control and infected cells for immunoprecipitation of SHP-1. Immune complexes were separated by SDS-PAGE under non-reducing conditions followed by transfer to nitrocellulose. Immunoblot analysis carried out using anti-EF-1α showed that *leishmania* EF-1α associated with SHP-1 in vivo, whereas the association of host-EF-1α with host SHP-1 was minimal. This shows that *leishmania* EF-1α is a selective SHP-1 binding protein during infection. EF-1α was purified to near homogeneity from murine macrophages and from *leishmania* promastigotes.

For immunoprecipitation of *leishmania* EF-1α, promastigotes were lysed in cold lysis buffer supplemented with protease and phosphatase inhibitors and incubated with either anti-EF-1α or isotype-matched irrelevant mAb. Protein G-agarose was added to recover immune complexes and after washing, immune complexes were released by boiling agarose beads in SDS-sample buffer without β-mercaptoethanol. Samples were separated on 7.5% SDS-PAGE and transferred to nitrocellulose and probed with anti-EF-1α mAb. The same blot was reprobed with anti-phosphotyrosine mAb 4G10 and showed that the upper band of EF-1α was tyrosine phosphorylated. Macrophages were either left untreated or infected with *leishmania* promastigotes at an approximate parasite to cell ratio of 15:1. After overnight (16 h) incubation, control and infected cells were washed and cytosolic fractions were prepared. Cells were treated with cold hypotonic buffer (20 mM Tris pH 7.5) containing protease and phosphatase inhibitors and passed through a 22-gauge needle to disrupt cells. Cell debris was removed by low speed centrifugation and cytosolic fractions were prepared by centrifuging supernatants at 100,000×g for 20 min at 4° C. The cytosolic fractions were supplemented with NaCl to a final concentration of 0.15 M and incubated with either rabbit anti-SHP-1 antibodies or normal rabbit serum for ip. Immune complexes were separated on non-reduced SDS-PAGE followed by transfer to nitrocellulose and probed with anti-EF-1α.

For binding assays, purified EF-1α from either *leishmania* or macrophages was incubated with 25 µl (packed volume) of glutathione-agarose beads containing equal amounts of GST-SHP-1. Binding was accomplished by mixing in 100 µl of binding buffer (50 mM HEPES [pH 7.5], 0.15 M NaCl, 1 mM EDTA, 1 mM DTT, 0.01% Triton X-100™ and 1% glycerol) for 2 h at 4° C. The beads were collected by centrifugation and washed four times with binding buffer. Bound EF-1α was eluted by boiling beads in Laemmli sample buffer, separated on SDS-PAGE followed by immunoblotting using anti-EF-1α. Binding of EF-1α to calmodulin-agarose was performed essentially as described above for GST-SHP-1 except that binding buffer contained 0.2 mM $CaCl_2$ instead of EDTA. Also, after incubation, non-bound proteins were removed and affinity beads were assayed for SHP-1 phosphatase activity using pNPP as a substrate. Relative phosphatase activity was assessed by measuring changes in absorbance at 405 nm.

Approximately 1 µg of purified EF-1α from *leishmania* or macrophages or an equivalent amount of BSA were incubated separately with Profect 1™ reagent (Targety Systems, Santee, Calif., USA) in serum free media to prepare protein-Profect-1™ complexes for delivery to macrophages (approximately $2 \times 10^6$) according to the manufacturer's instructions. After 2-3 hr of incubation, cells were lysed in buffer C (50 mM Tris [pH 7.5], 1% Triton X-100™ and 0.15M NaCl) containing a cocktail of protease inhibitors for 20 min on ice and incubated with anti-SHP-1 for 2 h end-over-end at 4° C. Immune complexes were recovered using protein A-sepharose and after extensive washing with buffer C, immune complexes were assayed for phosphatase activity using pNPP as a substrate.

Also after incubation for 2 h, macrophages into which *leishmani* or macrophage EF-1α was introduced were stimulated with 5U of murine interferon-γ for 5 h at 37° C. Cells were then processed for the expression of iNOS essentially as previously described [14]. The same blot was stripped and reprobed with anti-actin to control for protein loading.

Binding assays performed using the purified proteins and GST-SHP-1 glutathione-sepharose beads showed that EF-1α from *leishmania* bound directly and selectively to SHP-1 as comparatively little binding of host EF-1α was detected. In contrast, both *leishmania* and macrophage EF-1α bound directly and with similar affinities to calmodulin, a known EF-1α binding protein. This shows that the purified host EF-1α was functionally intact and also confirmed that *leishmania* EF-1α is a selective SHP-1 binding protein. Purified EF-1α proteins introduced into macrophages resulted in SHP-1 activation in vivo. In contrast, activation of SHP-1 was not observed when purified macrophage EF-1α or BSA were used as control proteins. Delivery of purified, native *leishmania* EF-1α, but not the corresponding host protein into cells blocked induction of iNOS expression in response to cell treatment with the interferon. Thus, *leishmania* EF-1α is able to recapitulate the deactivated phenotype of leishmania-infected macrophages. This shows that leishmania EF-1α but not the mammalian homologue is a selective activator of SHP-1 capable of inducing macrophage deactivation. EF-1α is detected as a tyrosine phosphorylated protein in promastigote growth medium in the absence of parasite lysis, indicating that it is exported. Furthermore, concentrated promastigote growth medium is able to activate SHP-1. When leishmania infected macrophages are subjected to selective lysis to preserve phagosome integrity, followed by immunoprecipitation of cytosolic SHP-1, EF-1α is identified in these complexes. Thus, these molecules do associate in vivo thereby providing an opportunity for activation of SHP-1.

Determination of Amino Acid Sequence of Pathogen EF1-α

The nucleotide (SEQ ID NO:21) and predicted amino acid sequence (SEQ ID NO:22) of EF-1α from L. donovani are shown in Table 1. These sequences were compared with other pathogens and with the human sequence (FIG. 1). Multiple alignment comparison showed that a high degree of homology extended through the complete sequence. The GTP-binding consensus motifs and the three lysine residues that are usually post-tranlationally modified [26-28] were found to be conserved. However, there were several important differences observed in the trypanosomatid sequences as compared to the human sequence. For example, at position 151-152 the replacement of glycine and valine in the human sequence with cysteines in the trypanosomatid sequences, suggests possible differences in folding of the proteins. Human EF-1α was found to contain a twelve extra amino acid insert when compared with the pathogen EF-1α sequences (FIG. 2). The protein sequence of L. donovani shows the presence of two previously unrecognized putative immunoreceptor tyrosine-based inhibitory motifs (ITIMs) as shown in italics. These specialized motifs are known to be present in signaling molecules with the capability of binding to Src homology 2 domains (SH2 domains) [12-14].

The Molecular Mass of Trypanosomatid EF-1α is Higher than Mammalian EF-1α

Initial immunoblot analysis of EF-1α in Triton X-100™ cell lysates of L. donovani promastigotes and the human carcinoma cell line A431 showed that the apparent molecular size of EF-1α of L. donovani was distinctly higher than the human homolog. To determine whether this was a specific characteristic of the leishmania protein or a more general property of the trypanosomatid family of which L. donovani is a member, Triton X-100™ cell lysates of several trypanosomatid and mammalian cell lines were separated on SDS-PAGE, transferred to nitrocellulose and probed with anti-EF-1α antibodies. The apparent molecular size of EF-1α from trypanosomatids was found to be approximately 56 kDa as compared to 50 kDa for EF-1α of mammalian origin. The molecular mass of EF-1α did not change when lysates of L. donovani promastigotes were taken at different stages of growth (exponential and stationary phases).

The Sub-cellular Distribution of Pathogen EF-1α is Distinct from Macrophage EF-1α

Cytosolic, Triton-soluble and Triton-insoluble fractions were prepared from L. donovani promastigotes and macrophages, separated by SDS-PAGE, transferred to nitrocellulose and probed with anti-EF-1α. In leishmania promastigotes, the majority of EF-1α was in the Triton-insoluble fraction, whereas in macrophages, EF-1α was predominantly cytosolic.

Sera from Patients with Visceral Leishmaniasis Recognize leishmania, but not Host EF-1α

EF-1α was immunoprecipitated from Triton X-100™ lysates of L. donovani promastigotes using anti-EF-1α antibodies. Immune complexes were separated by SDS-PAGE under non-reduced conditions followed by transfer to nitrocellulose membranes. Immunoblot analysis was carried out using either anti-EF-1α, normal human sera or sera from visceral leishmaniasis patients. Leishmania EF-1α was recognized by sera from patients infected with L. donovani. Importantly, EF-1α immunoprecipitated from cells of the human mononuclear phagocytic cell line THP-1, was not recognized by sera from L. donovani infected patients. This shows that the primary amino acid sequence differences between leishmania EF-1α compared with human EF-1α are sufficiently distinct that corresponding structural differences contribute to the formation of epitopes in the leishmania protein that are processed and recognized by the immune system. EF-1α of leishmania was a closely spaced doublet when separated on SDS-PAGE under non-reduced conditions.

Leishmania Infection Alters the Subcellular Distribution of Both Macrophage and leishmania EF-1α.

EF-1α is known to be involved in a variety of cellular processes in addition to regulation of protein synthesis [15-18]. Macrophages were incubated with L. donovani stationary phase promastigotes for 16 to 18 h at a parasite-to-cell ratio of approximately 10:1. This resulted in infection rates of >95% with approximately four to eight promastigotes per cell. To determine the sub-cellular distribution of EF-1α in non-infected and L. donovani infected macrophages, cytosolic, Triton-soluble and Triton-insoluble fractions were prepared as described above and analyzed for EF-1α by immunoblotting. In contrast to its predominant distribution in the Triton-insoluble fraction in promastigotes, leishmania EF-1α is principally cytosolic in infected macrophages. Simultaneously, infection of macrophages with leishmania results in a redistribution of host EF-1α to the cytosol, thereby increasing its overall abundance in this fraction. Similar results are obtained when cells were infected with leishmania amastigotes. The effect of leishmania infection on redistribution of EF-1α is specific, as phagocytosis by macrophages of Staphylococcus aureus do not cause redistribution of host EF-1α.

Summary

Pathogen EF-1α is a Src-homology 2 domain containing protein tyrosine phosphatase-1 (SHP-1) binding and activating protein. The pathogen protein is shorter than mammalian EF-1α a by a twelve amino acid deletion but the apparent molecular mass of the pathogen protein is higher than its mammalian counterpart. There is nearly complete sequence conservation amongst EF-1α proteins from pathogens when compared to mammalian EF-1α sequences. However, the sub-cellular distributions of pathogen EF-1α and host EF-1α are strikingly different. In the pathogen, the majority of EF-1α is Triton-X100™-insoluble, whereas macrophage EF-1α is predominantly cytosolic. Infection of macrophages with the pathogen causes redistribution of host as well as pathogen EF-1α. In contrast to its predominant distribution in the Triton-insoluble fraction in promastigotes and amastigotes, pathogen EF-1α is essentially completely cytosolic in infected macrophages. In addition, infection results in further redistribution of host EF-1α to the cytosol.

TABLE 1

```
   1 atgggcaaggataaggtgcacatgaaccttgtggtcgtcggccatgtcgacgccggcaag
     M  G  K  D  K  V  H  M  N  L  V  V  V  G  H  V  D  A  G  K   20

61 tccaccgccactggccacttgatctacaagtgcggtggcatcgacaagcgcacgatcgag
     S  T  A  T  G  H  L  I  Y  K  C  G  G  I  D  K  R  T  I  E   40

121 aagttcgagaaggaggccgccgagatcggcaaggcgtccttcaagtacgcgtgggtgctc
     K  F  E  K  E  A  A  E  I  G  K  A  S  F  K  Y  A  W  V  L   60

181 gacaagctgaaggcggagcgcgagcgcggcatcacgatcgacattgcgctgtggaagttc
     D  K  L  K  A  E  R  E  R  G  I  T  I  D  I  A  L  W  K  F   80

241 gagtcgcccaagtccgtgttcacgatcatcgatgcgcccggccaccgcgacttcatcaag
     E  S  P  K  S  V  F  T  I  I  D  A  P  G  H  R  D  F  I  K  100

301 aacatgatcacgggcacgtcgcaggcggacgccgccatcctgatgatcgactcgacgcat
     N  M  I  T  G  T  S  Q  A  D  A  A  I  L  M  I  D  S  T  H  120

361 ggtggcttcgaggctggcatctcgaaggacggccagacccgcgagcacgcgctgcttgcc
     G  G  F  E  A  G  I  S  K  D  G  Q  T  R  E  H  A  L  L  A  140

421 ttcacgcttggcgtgaagcagatggtggtgtgctgcaacaagatggacgacaagaccgtg
     F  T  L  G  V  K  Q  M  V  V  C  C  N  K  M  D  D  K  T  V  160

481 acgtacgcgcagtcgcgctacgatgagatcagcaaggaggtgggcgcgtacctgaagcgc
     T  Y  A  Q  S  R  Y  D  E  I  S  K  E  V  G  A  Y  L  K  R  180

541 gtgggctacaaccccgagaaggtgcgcttcatcccgatctcgggctggcagggcgacaac
     V  G  Y  N  P  E  K  V  R  F  I  P  I  S  G  W  Q  G  D  N  200

601 atgatcgagaggtcggacaacatgccgtggtacaagggtccacgctgctggacgcgctc
     M  I  E  R  S  D  N  M  P  W  Y  K  G  P  T  L  L  D  A  L  220

661 gacatgctggagccgccggtgcgcccggtggacaagccgctgcgcctgccctgcaggac
     D  M  L  E  P  P  V  R  P  V  D  K  P  L  R  L  P  L  Q  D  240

721 gtgtacaagatcggcggtatcgggactgtgcccgtgggccgcgtggagaccggcatcatg
     V  Y  K  I  G  G  I  G  T  V  P  V  G  R  V  E  T  G  I  M  260

781 aagccgggcgacgtggtgacgttcgcgcccgccaacgtgacgactgaggtgaagtcgatc
     K  P  G  D  V  V  T  F  A  P  A  N  V  T  T  E  V  K  S  I  280

841 gagatgcaccacgagcagctggcggaggcgcagcccggcgacaacgtcggcttcaacgtg
     E  M  H  H  E  Q  L  A  E  A  Q  P  G  D  N  V  G  F  N  V  300

901 aagaacgtgtcggtgaaggacatccgccgtggcaacgtgtgcggcaactcgaagaacgac
     K  N  V  S  V  K  D  I  R  R  G  N  V  C  G  N  S  K  N  D  320

961 ccgccgaaggaggcggccgacttcacggcgcaggtgatcgtgctgaaccaccccggccag
     P  P  K  E  A  A  D  F  T  A  Q  V  I  V  L  N  H  P  G  Q  340

1021 atcagcaacggctacgcgccggtgctggactgccacacgagccacattgcgtgccgcttc
     I  S  N  G  Y  A  P  V  L  D  C  H  T  S  H  I  A  C  R  F  360

1081 gcggaaatcgagtccaagatcgaccgccgctccggcaaggagctggagaagaaccccaag
     A  E  I  E  S  K  I  D  R  R  S  G  K  E  L  E  K  N  P  K  380

1141 gcgatcaagtctggcgatgccgcgatcgtgaagatggtgccgcagaagccgatgtgcgtg
     A  I  K  S  G  D  A  A  I  V  K  M  V  P  Q  K  P  M  C  V  400

1201 gaggtgttcaacgactacgcgccgctgggccgctttgccgtgcgcgacatgcggcagacg
     E  V  F  N  D  Y  A  P  L  G  R  F  A  V  R  D  M  R  Q  T  420

1261 gtggccgtgggcatcatcaagggcgtgaacaagaaggagggcagcggcggtaaggtgacc
     V  A  V  G  I  I  K  G  V  N  K  K  E  G  S  G  G  K  V  T  440

1321 aaggcggccgcgaaggctgcgaagaag
     K  A  A  A  K  A  A  K  K                                    449
```

Molecular Modeling of EF-1α

Modeling of the structure of *leishmania* EF-1α was done using the SwissPDB Viewer™ package [11]. A homology template search was done in which the amino acid sequence of *leishmania* EF-1α (SEQ ID NO:22) in Fasta format was downloaded into the software environment of SwissPDB™. The EF-1α sequence was then submitted to the Expasy™ server (www.expasy.ch) to search against the database of proteins of known sequence. The server returned the sequence of *Saccharomyces cerevisiae* EF-1α (1G7CA) as a high homology search result. Three other PDB entries (1F60A, 1IJEA, 1IJFA) corresponding to EF-1α proteins from *S. cerevisiae* were also identified as possible modeling templates and were used for homology modeling of *L. donovani* EF-1α. Also see Tables 2 and 3 for sequence identities of EF-1α as between different organisms. Table 4 shows the three-dimensional coordinates relative to the space occupied by all *leishmania* EF-1α atoms, for the atoms in amino acids 150-230, as generated by the Expasy™ server using the sequence from the Swiss-PDB Viewer™.

For homology modeling, the templates for 1G7C, 1F60A, 1IJEA, 1IJFA were downloaded from the ExPasy™ server and imported into SwissPDB™ program The template backbones were superimposed by using "SwissPDB|Fit|Magic Fit™" procedure. The structure of 1G7CA was used as a master template. To derive a preliminary structural estimate for EF-1α from *L. donovani*, the templates for 1G7C, 1F60A, 1IJEA, 1IJFA were superimposed and the sequence of the *leishmania* protein was fitted into the composite using "SwissPDB|Fit|Raw Sequence™" procedure. Consecutive use of procedures "SwissPDB|Fit|Magic Fit™", "SwissPDB|Fit|Improve Fit™" and "SwissPDB|Fit|Best™" allowed the predicted structure to be improved. In order to refine this preliminary structure further, the side chains and terminal chains were modeled. This was done using the Molecular Operation Environment (MOE™) software package (Version 2001.01, Chemical Computing Group, Inc., Montreal, Canada). The homology model of *leishmania* EF-1α previously built by the SwissPDB Viewer™ was used as a template and the curated PDB file 1G7C from the PDB database provided with the MOE™ package was used as a second template. The 1G7C template from the curated PDB database was imported by command "MOE|File|Protein Database™" and the sequence of *leishmania* EF-1α and its preliminary SwissPDB™ homology model were downloaded using option "MOE|File|Open™". The MOE™ Sequence Editor was then used for iterative sequence alignment with Gonnet substitution matrix. Secondary structure elements were not used for the sequence alignment. The MOE™ command "Seq. Editor|Homology|Align™" was used to perform the alignment. Homology modeling of *leishmania* EF-1α was then carried out with the highest degree of protein structure optimization. The previously derived SwissPDB™ model of the *leishmania* protein was used as a template. The final structure was derived as a Cartesian average of the top ten scored, non-minimized intermediate models. The estimated top ten homology models built for *leishmania* EF-1α were saved in MOE™ database*.mdb format to be viewed by the MOE™ database viewer called by "MOE|Open|*.mdb™". The final 3-D structure of the protein was averaged over the top ten scoring models.

Once the refined 3-D model of the EF-1α protein from *L. donovani* was created, the homology modeling procedure was repeated on a modeling template of EF-1α from *S. cerevisiae* (PDB file 1G7CA). The modeling routine was carried out in the exact same way as previously described for *L. donovanis* EF-1α with all numerical parameters the same. This step was taken in order to justify the accuracy and to build terminal chains not previously modeled by the SwissPDB Viewer™. The homology model of the protein EF-1α from *L. donovani* created on the 1G7CA template by MOE™ resembled the SwissPDB™ model with very high accuracy. The two structures of the *leishmania* protein created by MOE™ on the templates of 1G7CA and of the SwissPDB™ model had a high degree of resemblance with a calculated RMSD between the two structures of 0.69A. Based upon this analysis, the 3-D structure of EF-1α from *L. donovani* built using MOE™ on a template of the SwissPDB™ model was accepted as final. Lastly, since EF-1α proteins from *Mus musculus* and *Homo sapiens* share 99.8% identity and have 81.1% sequence identity with 1G7C, homology modeling of these proteins was done in the same manner as for *L. donovani* EF-1α.

TABLE 2

The amino acid sequences set out below are:
a) EF-1α from *Leishmania donovani*, b) EF-1α from *Saccharomyces Cerevisiae*, c) EF-1α from *Mus musculus*, d) EF-1α from *Homo sapiens*.

a) EF-1α leishmania protein
MGKDKVHMNLVVVGHVDAGKSTATGHLIYKCGG    (SEQ ID NO: 22)

IDKRTIEKFEKEAAEIGKASFKYAWVLDKLKAE

RERGITIDIALWKFESPKSVFTIIDAPGHRDFI

KNMITGTSQADAAILMIDSTHGGFEAGISKDGQ

TREHALLAFTLGVKQMVVCNKMDDKTVTYAQSR

YDEISKEVGAYLKRVGYNPEKVRFIPISGWQGD

NIERSDNMPWYKGPTLLDALDMLEPPVRPVDKP

LRLPLQDVYKIGGIGTVPGRVETGIMKPGDVVT

FAPANVTTEVKSIEMHHEQLAEAQPGDNVGFNV

KVSVKDIRRGNVCGNSKNDPPKEAADFTAQVIV

LNHPGQISNGYAPVLDCHSHIACRFAEIESKID

RRSGKELEKNPKAIKSGDAAIVKMVPQKPMCVE

VFNYAPLGRFAVRDMRQTVAVGIIKGVNKKEGS

GGKVTKAAAKAAKK b) EF-1α YEAST
MGKEKSHINVVVIGHVDSGKSTTTGHLIYKCGG    (SEQ ID NO: 23)

IDKRTIEKFEKEAAELGKGSFKYAWVLDKLKAE

RERGITIDIALWKFETPKYQVTVIDAPGHRDFI

KNMITGTSQADCAILIIAGGVGEFEAGISKDGQ

TREHALLAFTLGVRQLIVAVNKMDSVKWDESRF

QEIVKETSNFIKKVGYNPKTVPFVPISGWNGDN

MIEATTNAPWYKGWEKETKAGVVKGKTLLEAID

AIEQPSRPTDKPLRLPLQDVYKIGGIGTVPVGR

VETGVIKPGMVVTFAPAGVTTEVKSVEMHHEQL

EQGVPGDNVGFNVKNVSVKEIRRGNVCGDAKND

PPKGCASFNATVIVLNHPGQISAGYSPVLDCHT

AHIACRFDELLEKNDRRSGKKLEDHPKFLKSGD

TABLE 2-continued

The amino acid sequences set out below are:
a) EF-1α from *Leishmania donovani*, b)
EF-1α from *Saccharomyces Cerevisiae*, c) EF-1α
from *Mus musculus*, d) EF-1α from *Homo sapiens*.

AALVKFVPSKPMCVEAFSEYPPLGRFAVRDMRQ

TVAVGVIKSVDKTEKAAKVTKAAQKAAKK c) EF-1α MOUSE
MGKEKTHINIVVIGHVDSGKSTTTGHLIYKCGG (SEQ ID NO: 24)

IDKRTIEKFEKEAAEMGKGSFKYAWVLDKLKAE

RERGITIDISLWKFETSKYYVTIIDAPGHRDFI

KNMITGTSQADCAVLIVAAGVGEFEAGISKNGQ

TREHALLAYTLGVKQLIVGVNKMDSTEPPYSQK

RYEEIVKEVSTYIKKIGYNPDTVAFVPISGWNG

DNMLEPSANMPWFKGWKVTRKDGSASGTTLLEA

LDCILPPTRPTDKPLRLPLQDVYKIGGIGTVPV

GRVETGVLKPGMVVTFAPVNVTTEVKSVEMHHE

ALSEALPGDNVGFNVKNVSVKDVRRGNVAGDSK

NDPPMEAAGFTAQVIILNHPGQISAGYAPVLDC

HTAHIACKFAELKEKIDRRSGKKLEDGPKFLKS

GDAAIVDMVPGKPMCVESFSDYPPLGRFAVRDM

RQTVAVGVIKAVDKKAAGAGKVTKSAQKAQKAK d) EF-1α HUMAN
MGKEKTHINIVVIGHVDSGKSTTTGHLIYKCGG (SEQ ID NO: 25)

IDKRTIEKFEKEAAEMGKGSFKYAWVLDKLKAE

RERGITIDISLWKFETSKYYVTIIDAPGHRDFI

KNMITGTSQADCAVLIVAAGVGEFEAGISKNGQ

TABLE 2-continued

The amino acid sequences set out below are:
a) EF-1α from *Leishmania donovani*, b)
EF-1α from *Saccharomyces Cerevisiae*, c) EF-1α
from *Mus musculus*, d) EF-1α from *Homo sapiens*.

TREHALLAYTLGVKQLIVGVNKMDSTEPPYSQK

RYEEIVKEVSTYIKKIGYNPDTVAFVPISGWNG

DNMLEPSANMPWFKGWKVTRKDGNASGTTLLEA

LDCILPPTRPTDKPLRLPLQDVYKIGGIGTVPV

GRVETGVLKPGMVVTFAPVNVTTEVKSVEMHHE

ALSEALPGDNVGFNVKNVSVKDVRRGNVAGDSK

NDPPMEAAGFTAQVIILNHPGQISAGYAPVLDC

HTAHIACKFAELKEKIDRRSGKKLEDGPKFLKS

GDAAIVDMVPGKPMCVESFSDYPPLGRFAVRDM

RQTVAVGVIKAVDKKAAGAGKVTKSAQKAQKAK

TABLE 3

Pair wise percentage residue identity between sequences of EF-1α proteins from four organisms.

| | EF1α | EF11_HU | 1G7C.A | AAH0406 |
|---|---|---|---|---|
| EF-1α (*Leishmania donovani*) | 100.0 | 75.5 | 75.0 | 75.5 |
| EF11_HUMAN (*Homo sapiens*) | 77.7 | 100.0 | 81.1 | 99.8 |
| 1G7C.A (*Saccharomyces Cerevisiae*) | 73.5 | 77.3 | 100.0 | 77.3 |
| AAH0406 (*Mus musculus*) | 77.7 | 99.8 | 81.1 | 100.0 |

TABLE 4

| ATOM | 1064 | N   | ALA | 140 | 15.361 | 36.882 | 35.423 | 1.00 | 99.99 |
|------|------|-----|-----|-----|--------|--------|--------|------|-------|
| ATOM | 1065 | CA  | ALA | 140 | 15.421 | 35.447 | 35.623 | 1.00 | 99.99 |
| ATOM | 1066 | C   | ALA | 140 | 14.226 | 34.895 | 36.396 | 1.00 | 99.99 |
| ATOM | 1067 | O   | ALA | 140 | 13.576 | 33.915 | 35.991 | 1.00 | 99.99 |
| ATOM | 1068 | CB  | ALA | 140 | 16.736 | 35.081 | 36.326 | 1.00 | 99.99 |
| ATOM | 1069 | N   | PHE | 141 | 13.804 | 35.577 | 37.436 | 1.00 | 99.99 |
| ATOM | 1070 | CA  | PHE | 141 | 12.675 | 35.123 | 38.269 | 1.00 | 99.99 |
| ATOM | 1071 | C   | PHE | 141 | 11.407 | 35.122 | 37.432 | 1.00 | 99.99 |
| ATOM | 1072 | O   | PHE | 141 | 10.620 | 34.173 | 37.459 | 1.00 | 99.99 |
| ATOM | 1073 | CB  | PHE | 141 | 12.498 | 36.060 | 39.459 | 1.00 | 99.99 |
| ATOM | 1074 | CG  | PHE | 141 | 11.343 | 35.588 | 40.306 | 1.00 | 99.99 |
| ATOM | 1075 | CD1 | PHE | 141 | 11.503 | 34.488 | 41.158 | 1.00 | 99.99 |
| ATOM | 1076 | CD2 | PHE | 141 | 10.111 | 36.249 | 40.241 | 1.00 | 99.99 |
| ATOM | 1077 | CE1 | PHE | 141 | 10.431 | 34.050 | 41.945 | 1.00 | 99.99 |
| ATOM | 1078 | CE2 | PHE | 141 | 9.038  | 35.809 | 41.027 | 1.00 | 99.99 |
| ATOM | 1079 | CZ  | PHE | 141 | 9.199  | 34.710 | 41.879 | 1.00 | 99.99 |
| ATOM | 1080 | N   | THR | 142 | 11.235 | 36.224 | 36.696 | 1.00 | 99.99 |
| ATOM | 1081 | CA  | THR | 142 | 10.040 | 36.379 | 35.849 | 1.00 | 99.99 |
| ATOM | 1082 | C   | THR | 142 | 9.939  | 35.281 | 34.801 | 1.00 | 99.99 |
| ATOM | 1083 | O   | THR | 142 | 8.855  | 34.740 | 34.509 | 1.00 | 99.99 |
| ATOM | 1084 | CB  | THR | 142 | 10.039 | 37.761 | 35.183 | 1.00 | 99.99 |
| ATOM | 1085 | OG1 | THR | 142 | 10.103 | 38.782 | 36.209 | 1.00 | 99.99 |
| ATOM | 1086 | CG2 | THR | 142 | 8.765  | 37.975 | 34.368 | 1.00 | 99.99 |
| ATOM | 1087 | N   | LEU | 143 | 11.062 | 34.879 | 34.219 | 1.00 | 99.99 |
| ATOM | 1088 | CA  | LEU | 143 | 11.141 | 33.883 | 33.162 | 1.00 | 99.99 |
| ATOM | 1089 | C   | LEU | 143 | 11.091 | 32.465 | 33.716 | 1.00 | 99.99 |
| ATOM | 1090 | O   | LEU | 143 | 11.213 | 31.511 | 32.929 | 1.00 | 99.99 |

TABLE 4-continued

| | | | | | | | | |
|---|---|---|---|---|---|---|---|---|
| ATOM | 1091 | CB | LEU | 143 | 12.399 | 34.141 | 32.316 | 1.00 99.99 |
| ATOM | 1092 | CG | LEU | 143 | 12.542 | 35.476 | 31.554 | 1.00 99.99 |
| ATOM | 1093 | CD1 | LEU | 143 | 13.931 | 35.629 | 30.959 | 1.00 99.99 |
| ATOM | 1094 | CD2 | LEU | 143 | 11.456 | 35.618 | 30.506 | 1.00 99.99 |
| ATOM | 1095 | N | GLY | 144 | 10.933 | 32.283 | 35.017 | 1.00 99.99 |
| ATOM | 1096 | CA | GLY | 144 | 10.799 | 30.967 | 35.607 | 1.00 99.99 |
| ATOM | 1097 | C | GLY | 144 | 12.115 | 30.325 | 35.994 | 1.00 99.99 |
| ATOM | 1098 | O | GLY | 144 | 12.126 | 29.090 | 36.190 | 1.00 99.99 |
| ATOM | 1099 | N | VAL | 145 | 13.187 | 31.091 | 36.089 | 1.00 99.99 |
| ATOM | 1100 | CA | VAL | 145 | 14.462 | 30.502 | 36.559 | 1.00 99.99 |
| ATOM | 1101 | C | VAL | 145 | 14.239 | 30.404 | 38.062 | 1.00 99.99 |
| ATOM | 1102 | O | VAL | 145 | 14.262 | 31.423 | 38.755 | 1.00 99.99 |
| ATOM | 1103 | CB | VAL | 145 | 15.659 | 31.390 | 36.222 | 1.00 99.99 |
| ATOM | 1104 | CG1 | VAL | 145 | 16.949 | 30.769 | 36.795 | 1.00 99.99 |
| ATOM | 1105 | CG2 | VAL | 145 | 15.822 | 31.635 | 34.727 | 1.00 99.99 |
| ATOM | 1106 | N | LYS | 146 | 13.886 | 29.268 | 38.639 | 1.00 99.99 |
| ATOM | 1107 | CA | LYS | 146 | 13.577 | 29.208 | 40.048 | 1.00 99.99 |
| ATOM | 1108 | C | LYS | 146 | 14.752 | 28.799 | 40.934 | 1.00 99.99 |
| ATOM | 1109 | O | LYS | 146 | 14.616 | 29.051 | 42.125 | 1.00 99.99 |
| ATOM | 1110 | CB | LYS | 146 | 12.466 | 28.193 | 40.293 | 1.00 99.99 |
| ATOM | 1111 | CG | LYS | 146 | 11.159 | 28.718 | 39.711 | 1.00 99.99 |
| ATOM | 1112 | CD | LYS | 146 | 10.034 | 27.738 | 40.022 | 1.00 99.99 |
| ATOM | 1113 | CE | LYS | 146 | 8.741 | 28.225 | 39.376 | 1.00 99.99 |
| ATOM | 1114 | NZ | LYS | 146 | 7.646 | 27.306 | 39.715 | 1.00 99.99 |
| ATOM | 1115 | N | GLN | 147 | 15.787 | 28.256 | 40.334 | 1.00 99.99 |
| ATOM | 1116 | CA | GLN | 147 | 16.964 | 27.888 | 41.155 | 1.00 99.99 |
| ATOM | 1117 | C | GLN | 147 | 17.990 | 29.020 | 41.119 | 1.00 99.99 |
| ATOM | 1118 | O | GLN | 147 | 18.199 | 29.657 | 40.079 | 1.00 99.99 |
| ATOM | 1119 | CB | GLN | 147 | 17.594 | 26.631 | 40.570 | 1.00 99.99 |
| ATOM | 1120 | CG | GLN | 147 | 16.591 | 25.449 | 40.562 | 1.00 99.99 |
| ATOM | 1121 | CD | GLN | 147 | 17.240 | 24.152 | 40.203 | 1.00 99.99 |
| ATOM | 1122 | OE1 | GLN | 147 | 18.120 | 23.638 | 40.897 | 1.00 99.99 |
| ATOM | 1123 | NE2 | GLN | 147 | 16.840 | 23.605 | 39.050 | 1.00 99.99 |
| ATOM | 1124 | N | MET | 148 | 18.561 | 29.252 | 42.289 | 1.00 99.99 |
| ATOM | 1125 | CA | MET | 148 | 19.544 | 30.312 | 42.454 | 1.00 99.99 |
| ATOM | 1126 | C | MET | 148 | 20.628 | 29.844 | 43.423 | 1.00 99.99 |
| ATOM | 1127 | O | MET | 148 | 20.382 | 29.108 | 44.371 | 1.00 99.99 |
| ATOM | 1128 | CB | MET | 148 | 18.870 | 31.562 | 43.010 | 1.00 99.99 |
| ATOM | 1129 | CG | MET | 148 | 17.910 | 32.129 | 41.971 | 1.00 99.99 |
| ATOM | 1130 | SD | MET | 148 | 18.831 | 32.696 | 40.519 | 1.00 99.99 |
| ATOM | 1131 | CE | MET | 148 | 19.672 | 34.102 | 41.218 | 1.00 99.99 |
| ATOM | 1132 | N | VAL | 149 | 21.866 | 30.199 | 43.065 | 1.00 99.99 |
| ATOM | 1133 | CA | VAL | 149 | 23.014 | 29.986 | 43.969 | 1.00 99.99 |
| ATOM | 1134 | C | VAL | 149 | 23.604 | 31.360 | 44.199 | 1.00 99.99 |
| ATOM | 1135 | O | VAL | 149 | 23.753 | 32.136 | 43.221 | 1.00 99.99 |
| ATOM | 1136 | CB | VAL | 149 | 24.024 | 29.051 | 43.313 | 1.00 99.99 |
| ATOM | 1137 | CG1 | VAL | 149 | 25.342 | 29.108 | 44.079 | 1.00 99.99 |
| ATOM | 1138 | CG2 | VAL | 149 | 23.487 | 27.624 | 43.334 | 1.00 99.99 |
| ATOM | 1139 | N | VAL | 150 | 24.019 | 31.658 | 45.428 | 1.00 99.99 |
| ATOM | 1140 | CA | VAL | 150 | 24.706 | 32.930 | 45.690 | 1.00 99.99 |
| ATOM | 1141 | C | VAL | 150 | 26.158 | 32.627 | 46.035 | 1.00 99.99 |
| ATOM | 1142 | O | VAL | 150 | 26.374 | 31.762 | 46.902 | 1.00 99.99 |
| ATOM | 1143 | CB | VAL | 150 | 24.072 | 33.699 | 46.868 | 1.00 99.99 |
| ATOM | 1144 | CG1 | VAL | 150 | 24.969 | 34.887 | 47.280 | 1.00 99.99 |
| ATOM | 1145 | CG2 | VAL | 150 | 22.713 | 34.268 | 46.399 | 1.00 99.99 |
| ATOM | 1146 | N | CYS | 151 | 27.131 | 33.302 | 45.422 | 1.00 99.99 |
| ATOM | 1147 | CA | CYS | 151 | 28.535 | 33.135 | 45.812 | 1.00 99.99 |
| ATOM | 1148 | C | CYS | 151 | 29.003 | 34.476 | 46.349 | 1.00 99.99 |
| ATOM | 1149 | O | CYS | 151 | 28.876 | 35.476 | 45.628 | 1.00 99.99 |
| ATOM | 1150 | CB | CYS | 151 | 29.364 | 32.721 | 44.601 | 1.00 99.99 |
| ATOM | 1151 | SG | CYS | 151 | 29.137 | 31.020 | 44.026 | 1.00 99.99 |
| ATOM | 1152 | N | CYS | 152 | 29.525 | 34.518 | 47.570 | 1.00 99.99 |
| ATOM | 1153 | CA | CYS | 152 | 30.016 | 35.758 | 48.158 | 1.00 99.99 |
| ATOM | 1154 | C | CYS | 152 | 31.523 | 35.803 | 47.870 | 1.00 99.99 |
| ATOM | 1155 | O | CYS | 152 | 32.229 | 35.033 | 48.492 | 1.00 99.99 |
| ATOM | 1156 | CB | CYS | 152 | 29.748 | 35.762 | 49.659 | 1.00 99.99 |
| ATOM | 1157 | SG | CYS | 152 | 28.024 | 36.000 | 50.158 | 1.00 99.99 |
| ATOM | 1158 | N | ASN | 153 | 31.879 | 36.610 | 46.871 | 1.00 99.99 |
| ATOM | 1159 | CA | ASN | 153 | 33.267 | 36.656 | 46.406 | 1.00 99.99 |
| ATOM | 1160 | C | ASN | 153 | 34.073 | 37.684 | 47.162 | 1.00 99.99 |
| ATOM | 1161 | O | ASN | 153 | 33.544 | 38.500 | 47.939 | 1.00 99.99 |
| ATOM | 1162 | CB | ASN | 153 | 33.230 | 36.981 | 44.905 | 1.00 99.99 |
| ATOM | 1163 | CG | ASN | 153 | 34.526 | 36.631 | 44.199 | 1.00 99.99 |
| ATOM | 1164 | OD1 | ASN | 153 | 35.378 | 35.889 | 44.700 | 1.00 99.99 |
| ATOM | 1165 | ND2 | ASN | 153 | 34.693 | 37.237 | 43.013 | 1.00 99.99 |
| ATOM | 1166 | N | LYS | 154 | 35.391 | 37.675 | 46.934 | 1.00 99.99 |
| ATOM | 1167 | CA | LYS | 154 | 36.297 | 38.654 | 47.545 | 1.00 99.99 |
| ATOM | 1168 | C | LYS | 154 | 36.331 | 38.439 | 49.064 | 1.00 99.99 |
| ATOM | 1169 | O | LYS | 154 | 36.578 | 39.371 | 49.834 | 1.00 99.99 |

TABLE 4-continued

| | | | | | | | | |
|---|---|---|---|---|---|---|---|---|
| ATOM | 1170 | CB | LYS | 154 | 35.949 | 40.114 | 47.285 | 1.00 99.99 |
| ATOM | 1171 | CG | LYS | 154 | 35.502 | 40.618 | 45.942 | 1.00 99.99 |
| ATOM | 1172 | CD | LYS | 154 | 36.512 | 40.595 | 44.845 | 1.00 99.99 |
| ATOM | 1173 | CE | LYS | 154 | 36.047 | 41.282 | 43.575 | 1.00 99.99 |
| ATOM | 1174 | NZ | LYS | 154 | 36.349 | 42.748 | 43.518 | 1.00 99.99 |
| ATOM | 1175 | N | MET | 155 | 36.207 | 37.195 | 49.515 | 1.00 99.99 |
| ATOM | 1176 | CA | MET | 155 | 36.228 | 36.926 | 50.956 | 1.00 99.99 |
| ATOM | 1177 | C | MET | 155 | 37.604 | 37.243 | 51.514 | 1.00 99.99 |
| ATOM | 1178 | O | MET | 155 | 37.670 | 37.630 | 52.677 | 1.00 99.99 |
| ATOM | 1179 | CB | MET | 155 | 35.782 | 35.519 | 51.327 | 1.00 99.99 |
| ATOM | 1180 | CG | MET | 155 | 34.263 | 35.305 | 51.205 | 1.00 99.99 |
| ATOM | 1181 | SD | MET | 155 | 33.295 | 36.371 | 52.264 | 1.00 99.99 |
| ATOM | 1182 | CE | MET | 155 | 33.822 | 35.835 | 53.891 | 1.00 99.99 |
| ATOM | 1183 | N | ASP | 156 | 38.669 | 37.148 | 50.717 | 1.00 99.99 |
| ATOM | 1184 | CA | ASP | 156 | 39.984 | 37.540 | 51.257 | 1.00 99.99 |
| ATOM | 1185 | C | ASP | 156 | 40.032 | 38.990 | 51.696 | 1.00 99.99 |
| ATOM | 1186 | O | ASP | 156 | 40.675 | 39.369 | 52.699 | 1.00 99.99 |
| ATOM | 1187 | CB | ASP | 156 | 41.025 | 37.464 | 50.123 | 1.00 99.99 |
| ATOM | 1188 | CG | ASP | 156 | 41.210 | 36.043 | 49.667 | 1.00 99.99 |
| ATOM | 1189 | OD1 | ASP | 156 | 41.356 | 35.233 | 50.604 | 1.00 99.99 |
| ATOM | 1190 | OD2 | ASP | 156 | 41.210 | 35.754 | 48.459 | 1.00 99.99 |
| ATOM | 1191 | N | THR | 159 | 39.349 | 39.858 | 50.962 | 1.00 99.99 |
| ATOM | 1192 | CA | THR | 159 | 39.386 | 41.303 | 51.242 | 1.00 99.99 |
| ATOM | 1193 | C | THR | 159 | 38.742 | 41.655 | 52.571 | 1.00 99.99 |
| ATOM | 1194 | O | THR | 159 | 38.928 | 42.777 | 53.058 | 1.00 99.99 |
| ATOM | 1195 | CB | THR | 159 | 38.641 | 42.062 | 50.149 | 1.00 99.99 |
| ATOM | 1196 | OG1 | THR | 159 | 39.412 | 42.042 | 48.945 | 1.00 99.99 |
| ATOM | 1197 | CG2 | THR | 159 | 38.427 | 43.506 | 50.590 | 1.00 99.99 |
| ATOM | 1198 | N | VAL | 160 | 37.938 | 40.770 | 53.134 | 1.00 99.99 |
| ATOM | 1199 | CA | VAL | 160 | 37.302 | 40.958 | 54.424 | 1.00 99.99 |
| ATOM | 1200 | C | VAL | 160 | 37.815 | 39.914 | 55.399 | 1.00 99.99 |
| ATOM | 1201 | O | VAL | 160 | 37.174 | 39.569 | 56.386 | 1.00 99.99 |
| ATOM | 1202 | CB | VAL | 160 | 35.790 | 40.816 | 54.283 | 1.00 99.99 |
| ATOM | 1203 | CG1 | VAL | 160 | 35.162 | 40.667 | 55.665 | 1.00 99.99 |
| ATOM | 1204 | CG2 | VAL | 160 | 35.223 | 42.055 | 53.599 | 1.00 99.99 |
| ATOM | 1205 | N | THR | 161 | 39.019 | 39.411 | 55.123 | 1.00 99.99 |
| ATOM | 1206 | CA | THR | 161 | 39.730 | 38.470 | 55.973 | 1.00 99.99 |
| ATOM | 1207 | C | THR | 161 | 38.982 | 37.234 | 56.370 | 1.00 99.99 |
| ATOM | 1208 | O | THR | 161 | 39.105 | 36.669 | 57.466 | 1.00 99.99 |
| ATOM | 1209 | CB | THR | 161 | 40.128 | 39.149 | 57.279 | 1.00 99.99 |
| ATOM | 1210 | OG1 | THR | 161 | 41.186 | 40.078 | 57.030 | 1.00 99.99 |
| ATOM | 1211 | CG2 | THR | 161 | 40.602 | 38.096 | 58.275 | 1.00 99.99 |
| ATOM | 1212 | N | TYR | 162 | 38.085 | 36.725 | 55.481 | 1.00 99.99 |
| ATOM | 1213 | CA | TYR | 162 | 37.296 | 35.540 | 55.775 | 1.00 99.99 |
| ATOM | 1214 | C | TYR | 162 | 36.563 | 35.679 | 57.115 | 1.00 99.99 |
| ATOM | 1215 | O | TYR | 162 | 36.422 | 34.708 | 57.839 | 1.00 99.99 |
| ATOM | 1216 | CB | TYR | 162 | 38.203 | 34.316 | 55.847 | 1.00 99.99 |
| ATOM | 1217 | CG | TYR | 162 | 37.375 | 33.092 | 56.150 | 1.00 99.99 |
| ATOM | 1218 | CD1 | TYR | 162 | 36.606 | 32.499 | 55.142 | 1.00 99.99 |
| ATOM | 1219 | CD2 | TYR | 162 | 37.377 | 32.547 | 57.440 | 1.00 99.99 |
| ATOM | 1220 | CE1 | TYR | 162 | 35.839 | 31.362 | 55.423 | 1.00 99.99 |
| ATOM | 1221 | CE2 | TYR | 162 | 36.608 | 31.411 | 57.722 | 1.00 99.99 |
| ATOM | 1222 | CZ | TYR | 162 | 35.840 | 30.819 | 56.713 | 1.00 99.99 |
| ATOM | 1223 | OH | TYR | 162 | 35.093 | 29.714 | 56.988 | 1.00 99.99 |
| ATOM | 1224 | N | ALA | 163 | 36.039 | 36.865 | 57.388 | 1.00 99.99 |
| ATOM | 1225 | CA | ALA | 163 | 35.347 | 37.067 | 58.672 | 1.00 99.99 |
| ATOM | 1226 | C | ALA | 163 | 33.948 | 36.485 | 58.650 | 1.00 99.99 |
| ATOM | 1227 | O | ALA | 163 | 33.185 | 36.816 | 57.747 | 1.00 99.99 |
| ATOM | 1228 | CB | ALA | 163 | 35.291 | 38.554 | 59.001 | 1.00 99.99 |
| ATOM | 1229 | N | GLN | 164 | 33.634 | 35.657 | 59.644 | 1.00 99.99 |
| ATOM | 1230 | CA | GLN | 164 | 32.340 | 34.994 | 59.705 | 1.00 99.99 |
| ATOM | 1231 | C | GLN | 164 | 31.191 | 35.973 | 59.856 | 1.00 99.99 |
| ATOM | 1232 | O | GLN | 164 | 30.186 | 35.842 | 59.166 | 1.00 99.99 |
| ATOM | 1233 | CB | GLN | 164 | 32.301 | 34.042 | 60.896 | 1.00 99.99 |
| ATOM | 1234 | CG | GLN | 164 | 33.240 | 32.869 | 60.642 | 1.00 99.99 |
| ATOM | 1235 | CD | GLN | 164 | 32.676 | 31.934 | 59.582 | 1.00 99.99 |
| ATOM | 1236 | OE1 | GLN | 164 | 31.594 | 32.174 | 59.051 | 1.00 99.99 |
| ATOM | 1237 | NE2 | GLN | 164 | 33.415 | 30.866 | 59.274 | 1.00 99.99 |
| ATOM | 1238 | N | SER | 165 | 31.353 | 36.980 | 60.738 | 1.00 99.99 |
| ATOM | 1239 | CA | SER | 165 | 30.249 | 37.921 | 60.919 | 1.00 99.99 |
| ATOM | 1240 | C | SER | 165 | 29.918 | 38.659 | 59.634 | 1.00 99.99 |
| ATOM | 1241 | O | SER | 165 | 28.751 | 38.850 | 59.289 | 1.00 99.99 |
| ATOM | 1242 | CB | SER | 165 | 30.617 | 38.955 | 61.977 | 1.00 99.99 |
| ATOM | 1243 | OG | SER | 165 | 30.609 | 38.341 | 63.268 | 1.00 99.99 |
| ATOM | 1244 | N | ARG | 166 | 30.935 | 39.082 | 58.902 | 1.00 99.99 |
| ATOM | 1245 | CA | ARG | 166 | 30.785 | 39.751 | 57.635 | 1.00 99.99 |
| ATOM | 1246 | C | ARG | 166 | 30.037 | 38.857 | 56.641 | 1.00 99.99 |
| ATOM | 1247 | O | ARG | 166 | 29.099 | 39.338 | 55.991 | 1.00 99.99 |
| ATOM | 1248 | CB | ARG | 166 | 32.130 | 40.232 | 57.086 | 1.00 99.99 |

TABLE 4-continued

| | | | | | | | | |
|---|---|---|---|---|---|---|---|---|
| ATOM | 1249 | CG | ARG | 166 | 31.945 | 40.996 | 55.775 | 1.00 99.99 |
| ATOM | 1250 | CD | ARG | 166 | 31.124 | 42.281 | 55.948 | 1.00 99.99 |
| ATOM | 1251 | NE | ARG | 166 | 30.932 | 42.866 | 54.618 | 1.00 99.99 |
| ATOM | 1252 | CZ | ARG | 166 | 29.936 | 43.679 | 54.299 | 1.00 99.99 |
| ATOM | 1253 | NH1 | ARG | 166 | 29.019 | 44.005 | 55.205 | 1.00 99.99 |
| ATOM | 1254 | NH2 | ARG | 166 | 29.851 | 44.124 | 53.052 | 1.00 99.99 |
| ATOM | 1255 | N | TYR | 167 | 30.418 | 37.593 | 56.596 | 1.00 99.99 |
| ATOM | 1256 | CA | TYR | 167 | 29.703 | 36.661 | 55.688 | 1.00 99.99 |
| ATOM | 1257 | C | TYR | 167 | 28.249 | 36.543 | 56.122 | 1.00 99.99 |
| ATOM | 1258 | O | TYR | 167 | 27.348 | 36.586 | 55.261 | 1.00 99.99 |
| ATOM | 1259 | CB | TYR | 167 | 30.357 | 35.285 | 55.738 | 1.00 99.99 |
| ATOM | 1260 | CG | TYR | 167 | 29.626 | 34.345 | 54.811 | 1.00 99.99 |
| ATOM | 1261 | CD1 | TYR | 167 | 29.829 | 34.426 | 53.428 | 1.00 99.99 |
| ATOM | 1262 | CD2 | TYR | 167 | 28.743 | 33.393 | 55.333 | 1.00 99.99 |
| ATOM | 1263 | CE1 | TYR | 167 | 29.151 | 33.554 | 52.568 | 1.00 99.99 |
| ATOM | 1264 | CE2 | TYR | 167 | 28.063 | 32.521 | 54.473 | 1.00 99.99 |
| ATOM | 1265 | CZ | TYR | 167 | 28.268 | 32.602 | 53.091 | 1.00 99.99 |
| ATOM | 1266 | OH | TYR | 167 | 27.607 | 31.754 | 52.256 | 1.00 99.99 |
| ATOM | 1267 | N | ASP | 168 | 28.007 | 36.389 | 57.419 | 1.00 99.99 |
| ATOM | 1268 | CA | ASP | 168 | 26.626 | 36.277 | 57.903 | 1.00 99.99 |
| ATOM | 1269 | C | ASP | 168 | 25.797 | 37.518 | 57.599 | 1.00 99.99 |
| ATOM | 1270 | O | ASP | 168 | 24.612 | 37.326 | 57.256 | 1.00 99.99 |
| ATOM | 1271 | CB | ASP | 168 | 26.621 | 36.074 | 59.414 | 1.00 99.99 |
| ATOM | 1272 | CG | ASP | 168 | 27.110 | 34.666 | 59.742 | 1.00 99.99 |
| ATOM | 1273 | OD1 | ASP | 168 | 26.507 | 33.705 | 59.193 | 1.00 99.99 |
| ATOM | 1274 | OD2 | ASP | 168 | 28.082 | 34.563 | 60.537 | 1.00 99.99 |
| ATOM | 1275 | N | GLU | 169 | 26.378 | 38.719 | 57.795 | 1.00 99.99 |
| ATOM | 1276 | CA | GLU | 169 | 25.614 | 39.934 | 57.499 | 1.00 99.99 |
| ATOM | 1277 | C | GLU | 169 | 25.355 | 40.059 | 55.997 | 1.00 99.99 |
| ATOM | 1278 | O | GLU | 169 | 24.252 | 40.481 | 55.600 | 1.00 99.99 |
| ATOM | 1279 | CB | GLU | 169 | 26.340 | 41.187 | 57.997 | 1.00 99.99 |
| ATOM | 1280 | CG | GLU | 169 | 26.477 | 41.275 | 59.530 | 1.00 99.99 |
| ATOM | 1281 | CD | GLU | 169 | 25.140 | 41.157 | 60.248 | 1.00 99.99 |
| ATOM | 1282 | OE1 | GLU | 169 | 24.155 | 41.752 | 59.744 | 1.00 99.99 |
| ATOM | 1283 | OE2 | GLU | 169 | 25.029 | 40.451 | 61.280 | 1.00 99.99 |
| ATOM | 1284 | N | ILE | 170 | 26.338 | 39.608 | 55.188 | 1.00 99.99 |
| ATOM | 1285 | CA | ILE | 170 | 26.048 | 39.653 | 53.732 | 1.00 99.99 |
| ATOM | 1286 | C | ILE | 170 | 24.949 | 38.679 | 53.395 | 1.00 99.99 |
| ATOM | 1287 | O | ILE | 170 | 24.101 | 38.987 | 52.540 | 1.00 99.99 |
| ATOM | 1288 | CB | ILE | 170 | 27.346 | 39.315 | 52.963 | 1.00 99.99 |
| ATOM | 1289 | CG1 | ILE | 170 | 28.336 | 40.483 | 53.054 | 1.00 99.99 |
| ATOM | 1290 | CG2 | ILE | 170 | 27.042 | 39.033 | 51.486 | 1.00 99.99 |
| ATOM | 1291 | CD1 | ILE | 170 | 29.760 | 40.050 | 52.699 | 1.00 99.99 |
| ATOM | 1292 | N | SER | 171 | 24.896 | 37.498 | 53.995 | 1.00 99.99 |
| ATOM | 1293 | CA | SER | 171 | 23.882 | 36.480 | 53.718 | 1.00 99.99 |
| ATOM | 1294 | C | SER | 171 | 22.522 | 37.056 | 54.099 | 1.00 99.99 |
| ATOM | 1295 | O | SER | 171 | 21.575 | 36.904 | 53.373 | 1.00 99.99 |
| ATOM | 1296 | CB | SER | 171 | 24.168 | 35.226 | 54.538 | 1.00 99.99 |
| ATOM | 1297 | OG | SER | 171 | 25.314 | 34.559 | 54.005 | 1.00 99.99 |
| ATOM | 1298 | N | LYS | 172 | 22.444 | 37.710 | 55.264 | 1.00 99.99 |
| ATOM | 1299 | CA | LYS | 172 | 21.170 | 38.315 | 55.676 | 1.00 99.99 |
| ATOM | 1300 | C | LYS | 172 | 20.716 | 39.389 | 54.694 | 1.00 99.99 |
| ATOM | 1301 | O | LYS | 172 | 19.532 | 39.366 | 54.272 | 1.00 99.99 |
| ATOM | 1302 | CB | LYS | 172 | 21.336 | 39.013 | 57.046 | 1.00 99.99 |
| ATOM | 1303 | CG | LYS | 172 | 21.285 | 38.137 | 58.265 | 1.00 99.99 |
| ATOM | 1304 | CD | LYS | 172 | 21.731 | 38.876 | 59.551 | 1.00 99.99 |
| ATOM | 1305 | CE | LYS | 172 | 21.204 | 40.296 | 59.624 | 1.00 99.99 |
| ATOM | 1306 | NZ | LYS | 172 | 21.590 | 41.066 | 60.850 | 1.00 99.99 |
| ATOM | 1307 | N | GLU | 173 | 21.613 | 40.305 | 54.345 | 1.00 99.99 |
| ATOM | 1308 | CA | GLU | 173 | 21.242 | 41.386 | 53.428 | 1.00 99.99 |
| ATOM | 1309 | C | GLU | 173 | 20.916 | 40.861 | 52.036 | 1.00 99.99 |
| ATOM | 1310 | O | GLU | 173 | 19.979 | 41.389 | 51.418 | 1.00 99.99 |
| ATOM | 1311 | CB | GLU | 173 | 22.325 | 42.473 | 53.363 | 1.00 99.99 |
| ATOM | 1312 | CG | GLU | 173 | 22.412 | 43.258 | 54.665 | 1.00 99.99 |
| ATOM | 1313 | CD | GLU | 173 | 23.325 | 44.444 | 54.698 | 1.00 99.99 |
| ATOM | 1314 | OE1 | GLU | 173 | 23.153 | 45.373 | 53.869 | 1.00 99.99 |
| ATOM | 1315 | OE2 | GLU | 173 | 24.250 | 44.457 | 55.555 | 1.00 99.99 |
| ATOM | 1316 | N | VAL | 174 | 21.691 | 39.887 | 51.565 | 1.00 99.99 |
| ATOM | 1317 | CA | VAL | 174 | 21.392 | 39.334 | 50.237 | 1.00 99.99 |
| ATOM | 1318 | C | VAL | 174 | 20.099 | 38.536 | 50.228 | 1.00 99.99 |
| ATOM | 1319 | O | VAL | 174 | 19.373 | 38.497 | 49.208 | 1.00 99.99 |
| ATOM | 1320 | CB | VAL | 174 | 22.519 | 38.407 | 49.795 | 1.00 99.99 |
| ATOM | 1321 | CG1 | VAL | 174 | 22.057 | 37.577 | 48.601 | 1.00 99.99 |
| ATOM | 1322 | CG2 | VAL | 174 | 23.734 | 39.237 | 49.395 | 1.00 99.99 |
| ATOM | 1323 | N | GLY | 175 | 19.743 | 37.894 | 51.336 | 1.00 99.99 |
| ATOM | 1324 | CA | GLY | 175 | 18.489 | 37.148 | 51.469 | 1.00 99.99 |
| ATOM | 1325 | C | GLY | 175 | 17.330 | 38.150 | 51.363 | 1.00 99.99 |
| ATOM | 1326 | O | GLY | 175 | 16.374 | 37.828 | 50.664 | 1.00 99.99 |
| ATOM | 1327 | N | ALA | 176 | 17.514 | 39.323 | 51.967 | 1.00 99.99 |

TABLE 4-continued

| | | | | | | | | |
|---|---|---|---|---|---|---|---|---|
| ATOM | 1328 | CA | ALA | 176 | 16.453 | 40.343 | 51.802 | 1.00 99.99 |
| ATOM | 1329 | C | ALA | 176 | 16.335 | 40.775 | 50.342 | 1.00 99.99 |
| ATOM | 1330 | O | ALA | 176 | 15.240 | 40.822 | 49.776 | 1.00 99.99 |
| ATOM | 1331 | CB | ALA | 176 | 16.747 | 41.544 | 52.692 | 1.00 99.99 |
| ATOM | 1332 | N | TYR | 177 | 17.472 | 41.072 | 49.707 | 1.00 99.99 |
| ATOM | 1333 | CA | TYR | 177 | 17.516 | 41.456 | 48.290 | 1.00 99.99 |
| ATOM | 1334 | C | TYR | 177 | 16.811 | 40.444 | 47.426 | 1.00 99.99 |
| ATOM | 1335 | O | TYR | 177 | 15.996 | 40.847 | 46.569 | 1.00 99.99 |
| ATOM | 1336 | CB | TYR | 177 | 18.965 | 41.559 | 47.825 | 1.00 99.99 |
| ATOM | 1337 | CG | TYR | 177 | 19.001 | 41.956 | 46.370 | 1.00 99.99 |
| ATOM | 1338 | CD1 | TYR | 177 | 18.757 | 43.283 | 45.999 | 1.00 99.99 |
| ATOM | 1339 | CD2 | TYR | 177 | 19.279 | 40.996 | 45.389 | 1.00 99.99 |
| ATOM | 1340 | CE1 | TYR | 177 | 18.791 | 43.652 | 44.649 | 1.00 99.99 |
| ATOM | 1341 | CE2 | TYR | 177 | 19.311 | 41.364 | 44.038 | 1.00 99.99 |
| ATOM | 1342 | CZ | TYR | 177 | 19.068 | 42.692 | 43.669 | 1.00 99.99 |
| ATOM | 1343 | OH | TYR | 177 | 19.100 | 43.049 | 42.356 | 1.00 99.99 |
| ATOM | 1344 | N | LEU | 178 | 17.134 | 39.151 | 47.590 | 1.00 99.99 |
| ATOM | 1345 | CA | LEU | 178 | 16.561 | 38.157 | 46.676 | 1.00 99.99 |
| ATOM | 1346 | C | LEU | 178 | 15.109 | 37.850 | 47.006 | 1.00 99.99 |
| ATOM | 1347 | O | LEU | 178 | 14.381 | 37.463 | 46.105 | 1.00 99.99 |
| ATOM | 1348 | CB | LEU | 178 | 17.350 | 36.855 | 46.764 | 1.00 99.99 |
| ATOM | 1349 | CG | LEU | 178 | 18.700 | 37.029 | 46.076 | 1.00 99.99 |
| ATOM | 1350 | CD1 | LEU | 178 | 19.467 | 38.166 | 46.745 | 1.00 99.99 |
| ATOM | 1351 | CD2 | LEU | 178 | 19.500 | 35.738 | 46.191 | 1.00 99.99 |
| ATOM | 1352 | N | LYS | 179 | 14.719 | 38.003 | 48.273 | 1.00 99.99 |
| ATOM | 1353 | CA | LYS | 179 | 13.317 | 37.773 | 48.656 | 1.00 99.99 |
| ATOM | 1354 | C | LYS | 179 | 12.407 | 38.823 | 48.033 | 1.00 99.99 |
| ATOM | 1355 | O | LYS | 179 | 11.273 | 38.505 | 47.618 | 1.00 99.99 |
| ATOM | 1356 | CB | LYS | 179 | 13.239 | 37.832 | 50.196 | 1.00 99.99 |
| ATOM | 1357 | CG | LYS | 179 | 11.849 | 37.465 | 50.724 | 1.00 99.99 |
| ATOM | 1358 | CD | LYS | 179 | 11.867 | 37.351 | 52.257 | 1.00 99.99 |
| ATOM | 1359 | CE | LYS | 179 | 10.492 | 36.860 | 52.717 | 1.00 99.99 |
| ATOM | 1360 | NZ | LYS | 179 | 9.385 | 37.548 | 51.997 | 1.00 99.99 |
| ATOM | 1361 | N | ARG | 180 | 12.903 | 40.064 | 47.969 | 1.00 99.99 |
| ATOM | 1362 | CA | ARG | 180 | 12.121 | 41.142 | 47.349 | 1.00 99.99 |
| ATOM | 1363 | C | ARG | 180 | 11.968 | 40.862 | 45.862 | 1.00 99.99 |
| ATOM | 1364 | O | ARG | 180 | 10.924 | 41.130 | 45.290 | 1.00 99.99 |
| ATOM | 1365 | CB | ARG | 180 | 12.833 | 42.476 | 47.542 | 1.00 99.99 |
| ATOM | 1366 | CG | ARG | 180 | 13.142 | 42.679 | 49.021 | 1.00 99.99 |
| ATOM | 1367 | CD | ARG | 180 | 13.787 | 44.046 | 49.223 | 1.00 99.99 |
| ATOM | 1368 | NE | ARG | 180 | 14.296 | 44.193 | 50.605 | 1.00 99.99 |
| ATOM | 1369 | CZ | ARG | 180 | 14.988 | 45.254 | 51.013 | 1.00 99.99 |
| ATOM | 1370 | NH1 | ARG | 180 | 15.274 | 46.266 | 50.198 | 1.00 99.99 |
| ATOM | 1371 | NH2 | ARG | 180 | 15.397 | 45.284 | 52.278 | 1.00 99.99 |
| ATOM | 1372 | N | VAL | 181 | 12.974 | 40.262 | 45.222 | 1.00 99.99 |
| ATOM | 1373 | CA | VAL | 181 | 12.809 | 39.863 | 43.807 | 1.00 99.99 |
| ATOM | 1374 | C | VAL | 181 | 11.782 | 38.734 | 43.771 | 1.00 99.99 |
| ATOM | 1375 | O | VAL | 181 | 10.849 | 38.710 | 42.967 | 1.00 99.99 |
| ATOM | 1376 | CB | VAL | 181 | 14.143 | 39.387 | 43.244 | 1.00 99.99 |
| ATOM | 1377 | CG1 | VAL | 181 | 13.907 | 38.660 | 41.923 | 1.00 99.99 |
| ATOM | 1378 | CG2 | VAL | 181 | 15.055 | 40.585 | 43.007 | 1.00 99.99 |
| ATOM | 1379 | N | GLY | 182 | 11.899 | 37.722 | 44.678 | 1.00 99.99 |
| ATOM | 1380 | CA | GLY | 182 | 10.904 | 36.679 | 44.738 | 1.00 99.99 |
| ATOM | 1381 | C | GLY | 182 | 11.444 | 35.320 | 45.163 | 1.00 99.99 |
| ATOM | 1382 | O | GLY | 182 | 10.649 | 34.400 | 45.399 | 1.00 99.99 |
| ATOM | 1383 | N | TYR | 183 | 12.774 | 35.184 | 45.193 | 1.00 99.99 |
| ATOM | 1384 | CA | TYR | 183 | 13.330 | 33.866 | 45.529 | 1.00 99.99 |
| ATOM | 1385 | C | TYR | 183 | 13.182 | 33.542 | 47.012 | 1.00 99.99 |
| ATOM | 1386 | O | TYR | 183 | 13.155 | 34.446 | 47.819 | 1.00 99.99 |
| ATOM | 1387 | CB | TYR | 183 | 14.838 | 33.904 | 45.226 | 1.00 99.99 |
| ATOM | 1388 | CG | TYR | 183 | 15.111 | 33.978 | 43.735 | 1.00 99.99 |
| ATOM | 1389 | CD1 | TYR | 183 | 15.087 | 32.803 | 42.994 | 1.00 99.99 |
| ATOM | 1390 | CD2 | TYR | 183 | 15.382 | 35.168 | 43.119 | 1.00 99.99 |
| ATOM | 1391 | CE1 | TYR | 183 | 15.342 | 32.824 | 41.632 | 1.00 99.99 |
| ATOM | 1392 | CE2 | TYR | 183 | 15.642 | 35.216 | 41.761 | 1.00 99.99 |
| ATOM | 1393 | CZ | TYR | 183 | 15.628 | 34.036 | 41.037 | 1.00 99.99 |
| ATOM | 1394 | OH | TYR | 183 | 15.888 | 34.135 | 39.683 | 1.00 99.99 |
| ATOM | 1395 | N | ASN | 184 | 13.052 | 32.248 | 47.319 | 1.00 99.99 |
| ATOM | 1396 | CA | ASN | 184 | 13.006 | 31.837 | 48.736 | 1.00 99.99 |
| ATOM | 1397 | C | ASN | 184 | 14.432 | 31.543 | 49.169 | 1.00 99.99 |
| ATOM | 1398 | O | ASN | 184 | 14.967 | 30.526 | 48.734 | 1.00 99.99 |
| ATOM | 1399 | CB | ASN | 184 | 12.198 | 30.546 | 48.836 | 1.00 99.99 |
| ATOM | 1400 | CG | ASN | 184 | 12.170 | 29.965 | 50.235 | 1.00 99.99 |
| ATOM | 1401 | OD1 | ASN | 184 | 12.744 | 30.467 | 51.191 | 1.00 99.99 |
| ATOM | 1402 | ND2 | ASN | 184 | 11.425 | 28.836 | 50.367 | 1.00 99.99 |
| ATOM | 1403 | N | PRO | 185 | 15.009 | 32.320 | 50.071 | 1.00 99.99 |
| ATOM | 1404 | CA | PRO | 185 | 16.395 | 32.133 | 50.474 | 1.00 99.99 |
| ATOM | 1405 | C | PRO | 185 | 16.716 | 30.772 | 51.076 | 1.00 99.99 |
| ATOM | 1406 | O | PRO | 185 | 17.860 | 30.326 | 50.979 | 1.00 99.99 |

TABLE 4-continued

| | | | | | | | | |
|---|---|---|---|---|---|---|---|---|
| ATOM | 1407 | CB | PRO | 185 | 16.679 | 33.273 | 51.429 | 1.00 | 99.99 |
| ATOM | 1408 | CG | PRO | 185 | 15.633 | 34.308 | 51.150 | 1.00 | 99.99 |
| ATOM | 1409 | CD | PRO | 185 | 14.433 | 33.545 | 50.659 | 1.00 | 99.99 |
| ATOM | 1410 | N | GLU | 186 | 15.693 | 30.064 | 51.597 | 1.00 | 99.99 |
| ATOM | 1411 | CA | GLU | 186 | 15.973 | 28.749 | 52.161 | 1.00 | 99.99 |
| ATOM | 1412 | C | GLU | 186 | 16.337 | 27.722 | 51.108 | 1.00 | 99.99 |
| ATOM | 1413 | O | GLU | 186 | 16.918 | 26.695 | 51.486 | 1.00 | 99.99 |
| ATOM | 1414 | CB | GLU | 186 | 14.746 | 28.232 | 52.904 | 1.00 | 99.99 |
| ATOM | 1415 | CG | GLU | 186 | 14.527 | 29.054 | 54.151 | 1.00 | 99.99 |
| ATOM | 1416 | CD | GLU | 186 | 15.600 | 28.712 | 55.182 | 1.00 | 99.99 |
| ATOM | 1417 | OE1 | GLU | 186 | 16.663 | 29.386 | 55.155 | 1.00 | 99.99 |
| ATOM | 1418 | OE2 | GLU | 186 | 15.347 | 27.775 | 55.988 | 1.00 | 99.99 |
| ATOM | 1419 | N | LYS | 187 | 16.013 | 27.961 | 49.844 | 1.00 | 99.99 |
| ATOM | 1420 | CA | LYS | 187 | 16.299 | 27.070 | 48.758 | 1.00 | 99.99 |
| ATOM | 1421 | C | LYS | 187 | 17.628 | 27.417 | 48.047 | 1.00 | 99.99 |
| ATOM | 1422 | O | LYS | 187 | 17.937 | 26.798 | 47.030 | 1.00 | 99.99 |
| ATOM | 1423 | CB | LYS | 187 | 15.182 | 27.140 | 47.722 | 1.00 | 99.99 |
| ATOM | 1424 | CG | LYS | 187 | 13.912 | 26.528 | 48.299 | 1.00 | 99.99 |
| ATOM | 1425 | CD | LYS | 187 | 12.818 | 26.530 | 47.238 | 1.00 | 99.99 |
| ATOM | 1426 | CE | LYS | 187 | 11.525 | 25.986 | 47.838 | 1.00 | 99.99 |
| ATOM | 1427 | NZ | LYS | 187 | 10.483 | 25.944 | 46.803 | 1.00 | 99.99 |
| ATOM | 1428 | N | VAL | 188 | 18.327 | 28.422 | 48.567 | 1.00 | 99.99 |
| ATOM | 1429 | CA | VAL | 188 | 19.528 | 28.941 | 47.927 | 1.00 | 99.99 |
| ATOM | 1430 | C | VAL | 188 | 20.818 | 28.703 | 48.710 | 1.00 | 99.99 |
| ATOM | 1431 | O | VAL | 188 | 21.031 | 29.242 | 49.820 | 1.00 | 99.99 |
| ATOM | 1432 | CB | VAL | 188 | 19.367 | 30.484 | 47.761 | 1.00 | 99.99 |
| ATOM | 1433 | CG1 | VAL | 188 | 20.590 | 31.188 | 47.168 | 1.00 | 99.99 |
| ATOM | 1434 | CG2 | VAL | 188 | 18.143 | 30.830 | 46.914 | 1.00 | 99.99 |
| ATOM | 1435 | N | ARG | 189 | 21.774 | 28.048 | 48.104 | 1.00 | 99.99 |
| ATOM | 1436 | CA | ARG | 189 | 23.083 | 27.890 | 48.770 | 1.00 | 99.99 |
| ATOM | 1437 | C | ARG | 189 | 23.834 | 29.224 | 48.813 | 1.00 | 99.99 |
| ATOM | 1438 | O | ARG | 189 | 23.818 | 29.921 | 47.767 | 1.00 | 99.99 |
| ATOM | 1439 | CB | ARG | 189 | 23.932 | 26.876 | 48.011 | 1.00 | 99.99 |
| ATOM | 1440 | CG | ARG | 189 | 23.144 | 25.583 | 47.834 | 1.00 | 99.99 |
| ATOM | 1441 | CD | ARG | 189 | 24.020 | 24.545 | 47.141 | 1.00 | 99.99 |
| ATOM | 1442 | NE | ARG | 189 | 23.228 | 23.354 | 46.759 | 1.00 | 99.99 |
| ATOM | 1443 | CZ | ARG | 189 | 23.733 | 22.344 | 46.055 | 1.00 | 99.99 |
| ATOM | 1444 | NH1 | ARG | 189 | 24.997 | 22.335 | 45.640 | 1.00 | 99.99 |
| ATOM | 1445 | NH2 | ARG | 189 | 22.932 | 21.322 | 45.767 | 1.00 | 99.99 |
| ATOM | 1446 | N | PHE | 190 | 24.469 | 29.568 | 49.920 | 1.00 | 99.99 |
| ATOM | 1447 | CA | PHE | 190 | 25.354 | 30.731 | 49.995 | 1.00 | 99.99 |
| ATOM | 1448 | C | PHE | 190 | 26.787 | 30.258 | 50.171 | 1.00 | 99.99 |
| ATOM | 1449 | O | PHE | 190 | 27.048 | 29.607 | 51.198 | 1.00 | 99.99 |
| ATOM | 1450 | CB | PHE | 190 | 24.894 | 31.632 | 51.155 | 1.00 | 99.99 |
| ATOM | 1451 | CG | PHE | 190 | 23.580 | 32.326 | 50.914 | 1.00 | 99.99 |
| ATOM | 1452 | CD1 | PHE | 190 | 22.377 | 31.701 | 51.209 | 1.00 | 99.99 |
| ATOM | 1453 | CD2 | PHE | 190 | 23.580 | 33.621 | 50.392 | 1.00 | 99.99 |
| ATOM | 1454 | CE1 | PHE | 190 | 21.184 | 32.405 | 50.941 | 1.00 | 99.99 |
| ATOM | 1455 | CE2 | PHE | 190 | 22.396 | 34.304 | 50.167 | 1.00 | 99.99 |
| ATOM | 1456 | CZ | PHE | 190 | 21.197 | 33.702 | 50.455 | 1.00 | 99.99 |
| ATOM | 1457 | N | ILE | 191 | 27.598 | 30.531 | 49.123 | 1.00 | 99.99 |
| ATOM | 1458 | CA | ILE | 191 | 28.974 | 29.981 | 49.204 | 1.00 | 99.99 |
| ATOM | 1459 | C | ILE | 191 | 29.984 | 31.105 | 49.280 | 1.00 | 99.99 |
| ATOM | 1460 | O | ILE | 191 | 30.051 | 31.937 | 48.372 | 1.00 | 99.99 |
| ATOM | 1461 | CB | ILE | 191 | 29.268 | 29.135 | 47.970 | 1.00 | 99.99 |
| ATOM | 1462 | CG1 | ILE | 191 | 28.393 | 27.887 | 47.989 | 1.00 | 99.99 |
| ATOM | 1463 | CG2 | ILE | 191 | 30.738 | 28.726 | 47.973 | 1.00 | 99.99 |
| ATOM | 1464 | CD1 | ILE | 191 | 28.507 | 27.164 | 46.650 | 1.00 | 99.99 |
| ATOM | 1465 | N | PRO | 192 | 30.830 | 31.138 | 50.306 | 1.00 | 99.99 |
| ATOM | 1466 | CA | PRO | 192 | 31.893 | 32.126 | 50.413 | 1.00 | 99.99 |
| ATOM | 1467 | C | PRO | 192 | 33.058 | 31.666 | 49.548 | 1.00 | 99.99 |
| ATOM | 1468 | O | PRO | 192 | 33.458 | 30.488 | 49.627 | 1.00 | 99.99 |
| ATOM | 1469 | CB | PRO | 192 | 32.278 | 32.103 | 51.892 | 1.00 | 99.99 |
| ATOM | 1470 | CG | PRO | 192 | 31.950 | 30.709 | 52.337 | 1.00 | 99.99 |
| ATOM | 1471 | CD | PRO | 192 | 30.834 | 30.193 | 51.449 | 1.00 | 99.99 |
| ATOM | 1472 | N | ILE | 193 | 33.454 | 32.496 | 48.588 | 1.00 | 99.99 |
| ATOM | 1473 | CA | ILE | 193 | 34.518 | 32.064 | 47.670 | 1.00 | 99.99 |
| ATOM | 1474 | C | ILE | 193 | 35.564 | 33.148 | 47.512 | 1.00 | 99.99 |
| ATOM | 1475 | O | ILE | 193 | 35.441 | 34.294 | 47.962 | 1.00 | 99.99 |
| ATOM | 1476 | CB | ILE | 193 | 33.957 | 31.758 | 46.256 | 1.00 | 99.99 |
| ATOM | 1477 | CG1 | ILE | 193 | 33.416 | 33.043 | 45.593 | 1.00 | 99.99 |
| ATOM | 1478 | CG2 | ILE | 193 | 32.861 | 30.686 | 46.288 | 1.00 | 99.99 |
| ATOM | 1479 | CD1 | ILE | 193 | 33.197 | 32.931 | 44.076 | 1.00 | 99.99 |
| ATOM | 1480 | N | SER | 194 | 36.675 | 32.734 | 46.892 | 1.00 | 99.99 |
| ATOM | 1481 | CA | SER | 194 | 37.632 | 33.687 | 46.351 | 1.00 | 99.99 |
| ATOM | 1482 | C | SER | 194 | 37.853 | 33.266 | 44.898 | 1.00 | 99.99 |
| ATOM | 1483 | O | SER | 194 | 38.471 | 32.220 | 44.630 | 1.00 | 99.99 |
| ATOM | 1484 | CB | SER | 194 | 38.973 | 33.734 | 47.065 | 1.00 | 99.99 |
| ATOM | 1485 | OG | SER | 194 | 39.853 | 34.606 | 46.314 | 1.00 | 99.99 |

TABLE 4-continued

| | | | | | | | | |
|---|---|---|---|---|---|---|---|---|
| ATOM | 1486 | N | GLY | 195 | 37.269 | 33.998 | 43.924 | 1.00 99.99 |
| ATOM | 1487 | CA | GLY | 195 | 37.466 | 33.614 | 42.521 | 1.00 99.99 |
| ATOM | 1488 | C | GLY | 195 | 38.929 | 33.766 | 42.095 | 1.00 99.99 |
| ATOM | 1489 | O | GLY | 195 | 39.425 | 32.974 | 41.285 | 1.00 99.99 |
| ATOM | 1490 | N | TRP | 196 | 39.663 | 34.663 | 42.703 | 1.00 99.99 |
| ATOM | 1491 | CA | TRP | 196 | 41.045 | 34.924 | 42.375 | 1.00 99.99 |
| ATOM | 1492 | C | TRP | 196 | 41.981 | 33.876 | 42.951 | 1.00 99.99 |
| ATOM | 1493 | O | TRP | 196 | 42.976 | 33.503 | 42.309 | 1.00 99.99 |
| ATOM | 1494 | CB | TRP | 196 | 41.433 | 36.294 | 42.982 | 1.00 99.99 |
| ATOM | 1495 | CG | TRP | 196 | 42.662 | 36.807 | 42.287 | 1.00 99.99 |
| ATOM | 1496 | CD1 | TRP | 196 | 43.963 | 36.611 | 42.668 | 1.00 99.99 |
| ATOM | 1497 | CD2 | TRP | 196 | 42.696 | 37.582 | 41.084 | 1.00 99.99 |
| ATOM | 1498 | NE1 | TRP | 196 | 44.803 | 37.203 | 41.758 | 1.00 99.99 |
| ATOM | 1499 | CE2 | TRP | 196 | 44.055 | 37.830 | 40.793 | 1.00 99.99 |
| ATOM | 1500 | CE3 | TRP | 196 | 41.718 | 38.109 | 40.242 | 1.00 99.99 |
| ATOM | 1501 | CZ2 | TRP | 196 | 44.460 | 38.564 | 39.679 | 1.00 99.99 |
| ATOM | 1502 | CZ3 | TRP | 196 | 42.121 | 38.840 | 39.129 | 1.00 99.99 |
| ATOM | 1503 | CH2 | TRP | 196 | 43.482 | 39.064 | 38.865 | 1.00 99.99 |
| ATOM | 1504 | N | GLN | 197 | 41.704 | 33.389 | 44.152 | 1.00 99.99 |
| ATOM | 1505 | CA | GLN | 197 | 42.615 | 32.450 | 44.798 | 1.00 99.99 |
| ATOM | 1506 | C | GLN | 197 | 42.083 | 31.019 | 44.811 | 1.00 99.99 |
| ATOM | 1507 | O | GLN | 197 | 42.719 | 30.119 | 45.347 | 1.00 99.99 |
| ATOM | 1508 | CB | GLN | 197 | 42.848 | 32.867 | 46.246 | 1.00 99.99 |
| ATOM | 1509 | CG | GLN | 197 | 43.658 | 34.158 | 46.280 | 1.00 99.99 |
| ATOM | 1510 | CD | GLN | 197 | 45.104 | 33.910 | 45.876 | 1.00 99.99 |
| ATOM | 1511 | OE1 | GLN | 197 | 45.482 | 32.780 | 45.576 | 1.00 99.99 |
| ATOM | 1512 | NE2 | GLN | 197 | 45.912 | 34.972 | 45.869 | 1.00 99.99 |
| ATOM | 1513 | N | GLY | 198 | 40.890 | 30.796 | 44.296 | 1.00 99.99 |
| ATOM | 1514 | CA | GLY | 198 | 40.333 | 29.461 | 44.189 | 1.00 99.99 |
| ATOM | 1515 | C | GLY | 198 | 39.614 | 28.977 | 45.408 | 1.00 99.99 |
| ATOM | 1516 | O | GLY | 198 | 39.080 | 27.865 | 45.312 | 1.00 99.99 |
| ATOM | 1517 | N | ASP | 199 | 39.557 | 29.671 | 46.541 | 1.00 99.99 |
| ATOM | 1518 | CA | ASP | 199 | 38.895 | 29.110 | 47.715 | 1.00 99.99 |
| ATOM | 1519 | C | ASP | 199 | 37.438 | 28.767 | 47.441 | 1.00 99.99 |
| ATOM | 1520 | O | ASP | 199 | 36.679 | 29.623 | 47.011 | 1.00 99.99 |
| ATOM | 1521 | CB | ASP | 199 | 38.894 | 30.130 | 48.837 | 1.00 99.99 |
| ATOM | 1522 | CG | ASP | 199 | 40.295 | 30.525 | 49.264 | 1.00 99.99 |
| ATOM | 1523 | OD1 | ASP | 199 | 40.938 | 31.217 | 48.470 | 1.00 99.99 |
| ATOM | 1524 | OD2 | ASP | 199 | 40.630 | 30.074 | 50.375 | 1.00 99.99 |
| ATOM | 1525 | N | ASN | 200 | 37.056 | 27.544 | 47.772 | 1.00 99.99 |
| ATOM | 1526 | CA | ASN | 200 | 35.707 | 27.027 | 47.643 | 1.00 99.99 |
| ATOM | 1527 | C | ASN | 200 | 35.187 | 27.040 | 46.222 | 1.00 99.99 |
| ATOM | 1528 | O | ASN | 200 | 33.976 | 27.096 | 45.994 | 1.00 99.99 |
| ATOM | 1529 | CB | ASN | 200 | 34.734 | 27.816 | 48.556 | 1.00 99.99 |
| ATOM | 1530 | CG | ASN | 200 | 34.835 | 27.319 | 49.986 | 1.00 99.99 |
| ATOM | 1531 | OD1 | ASN | 200 | 35.284 | 26.199 | 50.240 | 1.00 99.99 |
| ATOM | 1532 | ND2 | ASN | 200 | 34.404 | 28.148 | 50.941 | 1.00 99.99 |
| ATOM | 1533 | N | MET | 201 | 36.061 | 27.054 | 45.216 | 1.00 99.99 |
| ATOM | 1534 | CA | MET | 201 | 35.586 | 26.989 | 43.828 | 1.00 99.99 |
| ATOM | 1535 | C | MET | 201 | 35.391 | 25.543 | 43.420 | 1.00 99.99 |
| ATOM | 1536 | O | MET | 201 | 34.292 | 25.062 | 43.158 | 1.00 99.99 |
| ATOM | 1537 | CB | MET | 201 | 36.540 | 27.748 | 42.884 | 1.00 99.99 |
| ATOM | 1538 | CG | MET | 201 | 36.577 | 29.227 | 43.265 | 1.00 99.99 |
| ATOM | 1539 | SD | MET | 201 | 35.126 | 30.040 | 42.508 | 1.00 99.99 |
| ATOM | 1540 | CE | MET | 201 | 35.473 | 29.868 | 40.759 | 1.00 99.99 |
| ATOM | 1541 | N | ILE | 202 | 36.522 | 24.824 | 43.375 | 1.00 99.99 |
| ATOM | 1542 | CA | ILE | 202 | 36.554 | 23.411 | 43.048 | 1.00 99.99 |
| ATOM | 1543 | C | ILE | 202 | 36.997 | 22.632 | 44.295 | 1.00 99.99 |
| ATOM | 1544 | O | ILE | 202 | 36.549 | 21.486 | 44.456 | 1.00 99.99 |
| ATOM | 1545 | CB | ILE | 202 | 37.537 | 23.165 | 41.909 | 1.00 99.99 |
| ATOM | 1546 | CG1 | ILE | 202 | 37.006 | 23.804 | 40.631 | 1.00 99.99 |
| ATOM | 1547 | CG2 | ILE | 202 | 37.700 | 21.663 | 41.695 | 1.00 99.99 |
| ATOM | 1548 | CD1 | ILE | 202 | 38.087 | 23.770 | 39.556 | 1.00 99.99 |
| ATOM | 1549 | N | GLU | 203 | 37.863 | 23.233 | 45.093 | 1.00 99.99 |
| ATOM | 1550 | CA | GLU | 203 | 38.296 | 22.588 | 46.339 | 1.00 99.99 |
| ATOM | 1551 | C | GLU | 203 | 37.920 | 23.465 | 47.535 | 1.00 99.99 |
| ATOM | 1552 | O | GLU | 203 | 37.905 | 24.694 | 47.446 | 1.00 99.99 |
| ATOM | 1553 | CB | GLU | 203 | 39.840 | 22.442 | 46.283 | 1.00 99.99 |
| ATOM | 1554 | CG | GLU | 203 | 40.220 | 21.492 | 45.138 | 1.00 99.99 |
| ATOM | 1555 | CD | GLU | 203 | 41.706 | 21.617 | 44.839 | 1.00 99.99 |
| ATOM | 1556 | OE1 | GLU | 203 | 42.411 | 21.320 | 45.834 | 1.00 99.99 |
| ATOM | 1557 | OE2 | GLU | 203 | 42.061 | 22.023 | 43.710 | 1.00 99.99 |
| ATOM | 1558 | N | ARG | 204 | 37.697 | 22.845 | 48.696 | 1.00 99.99 |
| ATOM | 1559 | CA | ARG | 204 | 37.302 | 23.615 | 49.877 | 1.00 99.99 |
| ATOM | 1560 | C | ARG | 204 | 38.403 | 24.521 | 50.375 | 1.00 99.99 |
| ATOM | 1561 | O | ARG | 204 | 39.594 | 24.178 | 50.300 | 1.00 99.99 |
| ATOM | 1562 | CB | ARG | 204 | 36.931 | 22.668 | 51.013 | 1.00 99.99 |
| ATOM | 1563 | CG | ARG | 204 | 35.890 | 21.668 | 50.524 | 1.00 99.99 |
| ATOM | 1564 | CD | ARG | 204 | 35.465 | 20.770 | 51.680 | 1.00 99.99 |

TABLE 4-continued

| ATOM | 1565 | NE  | ARG | 204 | 34.621 | 19.653 | 51.200 | 1.00 | 99.99 |
| ATOM | 1566 | CZ  | ARG | 204 | 34.198 | 18.672 | 51.994 | 1.00 | 99.99 |
| ATOM | 1567 | NH1 | ARG | 204 | 34.510 | 18.626 | 53.286 | 1.00 | 99.99 |
| ATOM | 1568 | NH2 | ARG | 204 | 33.442 | 17.717 | 51.458 | 1.00 | 99.99 |
| ATOM | 1569 | N   | SER | 205 | 38.010 | 25.637 | 50.986 | 1.00 | 99.99 |
| ATOM | 1570 | CA  | SER | 205 | 38.959 | 26.578 | 51.560 | 1.00 | 99.99 |
| ATOM | 1571 | C   | SER | 205 | 39.609 | 26.056 | 52.852 | 1.00 | 99.99 |
| ATOM | 1572 | O   | SER | 205 | 38.977 | 25.261 | 53.543 | 1.00 | 99.99 |
| ATOM | 1573 | CB  | SER | 205 | 38.252 | 27.887 | 51.896 | 1.00 | 99.99 |
| ATOM | 1574 | OG  | SER | 205 | 37.940 | 28.584 | 50.689 | 1.00 | 99.99 |
| ATOM | 1575 | N   | ASP | 206 | 40.804 | 26.573 | 53.134 | 1.00 | 99.99 |
| ATOM | 1576 | CA  | ASP | 206 | 41.469 | 26.349 | 54.414 | 1.00 | 99.99 |
| ATOM | 1577 | C   | ASP | 206 | 41.595 | 27.687 | 55.145 | 1.00 | 99.99 |
| ATOM | 1578 | O   | ASP | 206 | 42.325 | 27.833 | 56.132 | 1.00 | 99.99 |
| ATOM | 1579 | CB  | ASP | 206 | 42.856 | 25.759 | 54.182 | 1.00 | 99.99 |
| ATOM | 1580 | CG  | ASP | 206 | 42.723 | 24.310 | 53.718 | 1.00 | 99.99 |
| ATOM | 1581 | OD1 | ASP | 206 | 42.058 | 23.530 | 54.451 | 1.00 | 99.99 |
| ATOM | 1582 | OD2 | ASP | 206 | 43.286 | 23.997 | 52.635 | 1.00 | 99.99 |
| ATOM | 1583 | N   | ASN | 207 | 40.899 | 28.740 | 54.722 | 1.00 | 99.99 |
| ATOM | 1584 | CA  | ASN | 207 | 41.011 | 30.052 | 55.326 | 1.00 | 99.99 |
| ATOM | 1585 | C   | ASN | 207 | 39.846 | 30.398 | 56.242 | 1.00 | 99.99 |
| ATOM | 1586 | O   | ASN | 207 | 39.755 | 31.540 | 56.703 | 1.00 | 99.99 |
| ATOM | 1587 | CB  | ASN | 207 | 41.105 | 31.102 | 54.213 | 1.00 | 99.99 |
| ATOM | 1588 | CG  | ASN | 207 | 42.437 | 31.168 | 53.506 | 1.00 | 99.99 |
| ATOM | 1589 | OD1 | ASN | 207 | 42.572 | 31.108 | 52.266 | 1.00 | 99.99 |
| ATOM | 1590 | ND2 | ASN | 207 | 43.497 | 31.309 | 54.289 | 1.00 | 99.99 |
| ATOM | 1591 | N   | MET | 208 | 38.960 | 29.426 | 56.462 | 1.00 | 99.99 |
| ATOM | 1592 | CA  | MET | 208 | 37.762 | 29.718 | 57.265 | 1.00 | 99.99 |
| ATOM | 1593 | C   | MET | 208 | 37.330 | 28.530 | 58.083 | 1.00 | 99.99 |
| ATOM | 1594 | O   | MET | 208 | 36.412 | 27.756 | 57.775 | 1.00 | 99.99 |
| ATOM | 1595 | CB  | MET | 208 | 36.607 | 30.107 | 56.349 | 1.00 | 99.99 |
| ATOM | 1596 | CG  | MET | 208 | 36.916 | 31.439 | 55.675 | 1.00 | 99.99 |
| ATOM | 1597 | SD  | MET | 208 | 36.997 | 32.756 | 56.915 | 1.00 | 99.99 |
| ATOM | 1598 | CE  | MET | 208 | 35.283 | 32.840 | 57.389 | 1.00 | 99.99 |
| ATOM | 1599 | N   | PRO | 209 | 37.928 | 28.315 | 59.262 | 1.00 | 99.99 |
| ATOM | 1600 | CA  | PRO | 209 | 37.628 | 27.152 | 60.058 | 1.00 | 99.99 |
| ATOM | 1601 | C   | PRO | 209 | 36.173 | 27.166 | 60.513 | 1.00 | 99.99 |
| ATOM | 1602 | O   | PRO | 209 | 35.649 | 26.083 | 60.751 | 1.00 | 99.99 |
| ATOM | 1603 | CB  | PRO | 209 | 38.623 | 27.141 | 61.206 | 1.00 | 99.99 |
| ATOM | 1604 | CG  | PRO | 209 | 39.679 | 28.118 | 60.794 | 1.00 | 99.99 |
| ATOM | 1605 | CD  | PRO | 209 | 39.095 | 29.075 | 59.780 | 1.00 | 99.99 |
| ATOM | 1606 | N   | TRP | 210 | 35.523 | 28.324 | 60.590 | 1.00 | 99.99 |
| ATOM | 1607 | CA  | TRP | 210 | 34.130 | 28.397 | 60.991 | 1.00 | 99.99 |
| ATOM | 1608 | C   | TRP | 210 | 33.180 | 27.870 | 59.915 | 1.00 | 99.99 |
| ATOM | 1609 | O   | TRP | 210 | 32.011 | 27.668 | 60.227 | 1.00 | 99.99 |
| ATOM | 1610 | CB  | TRP | 210 | 33.739 | 29.857 | 61.259 | 1.00 | 99.99 |
| ATOM | 1611 | CG  | TRP | 210 | 34.082 | 30.810 | 60.137 | 1.00 | 99.99 |
| ATOM | 1612 | CD1 | TRP | 210 | 35.212 | 31.589 | 60.059 | 1.00 | 99.99 |
| ATOM | 1613 | CD2 | TRP | 210 | 33.300 | 31.125 | 58.977 | 1.00 | 99.99 |
| ATOM | 1614 | NE1 | TRP | 210 | 35.173 | 32.365 | 58.916 | 1.00 | 99.99 |
| ATOM | 1615 | CE2 | TRP | 210 | 34.030 | 32.060 | 58.222 | 1.00 | 99.99 |
| ATOM | 1616 | CE3 | TRP | 210 | 32.067 | 30.672 | 58.502 | 1.00 | 99.99 |
| ATOM | 1617 | CZ2 | TRP | 210 | 33.565 | 32.610 | 57.013 | 1.00 | 99.99 |
| ATOM | 1618 | CZ3 | TRP | 210 | 31.601 | 31.179 | 57.291 | 1.00 | 99.99 |
| ATOM | 1619 | CH2 | TRP | 210 | 32.329 | 32.149 | 56.580 | 1.00 | 99.99 |
| ATOM | 1620 | N   | TYR | 211 | 33.636 | 27.841 | 58.673 | 1.00 | 99.99 |
| ATOM | 1621 | CA  | TYR | 211 | 32.757 | 27.446 | 57.577 | 1.00 | 99.99 |
| ATOM | 1622 | C   | TYR | 211 | 32.425 | 25.974 | 57.600 | 1.00 | 99.99 |
| ATOM | 1623 | O   | TYR | 211 | 33.309 | 25.133 | 57.438 | 1.00 | 99.99 |
| ATOM | 1624 | CB  | TYR | 211 | 33.426 | 27.749 | 56.241 | 1.00 | 99.99 |
| ATOM | 1625 | CG  | TYR | 211 | 32.510 | 27.340 | 55.114 | 1.00 | 99.99 |
| ATOM | 1626 | CD1 | TYR | 211 | 31.410 | 28.139 | 54.779 | 1.00 | 99.99 |
| ATOM | 1627 | CD2 | TYR | 211 | 32.759 | 26.160 | 54.402 | 1.00 | 99.99 |
| ATOM | 1628 | CE1 | TYR | 211 | 30.561 | 27.760 | 53.733 | 1.00 | 99.99 |
| ATOM | 1629 | CE2 | TYR | 211 | 31.909 | 25.780 | 53.357 | 1.00 | 99.99 |
| ATOM | 1630 | CZ  | TYR | 211 | 30.810 | 26.580 | 53.023 | 1.00 | 99.99 |
| ATOM | 1631 | OH  | TYR | 211 | 29.985 | 26.209 | 52.006 | 1.00 | 99.99 |
| ATOM | 1632 | N   | LYS | 212 | 31.130 | 25.683 | 57.731 | 1.00 | 99.99 |
| ATOM | 1633 | CA  | LYS | 212 | 30.725 | 24.277 | 57.774 | 1.00 | 99.99 |
| ATOM | 1634 | C   | LYS | 212 | 30.138 | 23.817 | 56.438 | 1.00 | 99.99 |
| ATOM | 1635 | O   | LYS | 212 | 29.741 | 22.657 | 56.377 | 1.00 | 99.99 |
| ATOM | 1636 | CB  | LYS | 212 | 29.652 | 24.078 | 58.854 | 1.00 | 99.99 |
| ATOM | 1637 | CG  | LYS | 212 | 30.121 | 24.330 | 60.278 | 1.00 | 99.99 |
| ATOM | 1638 | CD  | LYS | 212 | 29.919 | 25.774 | 60.713 | 1.00 | 99.99 |
| ATOM | 1639 | CE  | LYS | 212 | 30.542 | 25.959 | 62.104 | 1.00 | 99.99 |
| ATOM | 1640 | NZ  | LYS | 212 | 30.860 | 27.363 | 62.498 | 1.00 | 99.99 |
| ATOM | 1641 | N   | GLY | 213 | 30.042 | 24.714 | 55.457 | 1.00 | 99.99 |
| ATOM | 1642 | CA  | GLY | 213 | 29.474 | 24.366 | 54.165 | 1.00 | 99.99 |
| ATOM | 1643 | C   | GLY | 213 | 28.190 | 25.163 | 53.928 | 1.00 | 99.99 |

TABLE 4-continued

| | | | | | | | | |
|---|---|---|---|---|---|---|---|---|
| ATOM | 1644 | O | GLY | 213 | 27.728 | 25.961 | 54.764 | 1.00 99.99 |
| ATOM | 1645 | N | PRO | 214 | 30.384 | 21.968 | 50.119 | 1.00 99.99 |
| ATOM | 1646 | CA | PRO | 214 | 31.323 | 23.006 | 50.495 | 1.00 99.99 |
| ATOM | 1647 | C | PRO | 214 | 31.609 | 24.012 | 49.363 | 1.00 99.99 |
| ATOM | 1648 | O | PRO | 214 | 31.814 | 25.200 | 49.551 | 1.00 99.99 |
| ATOM | 1649 | CB | PRO | 214 | 32.497 | 22.138 | 50.781 | 1.00 99.99 |
| ATOM | 1650 | CG | PRO | 214 | 32.294 | 20.881 | 49.969 | 1.00 99.99 |
| ATOM | 1651 | CD | PRO | 214 | 31.066 | 20.588 | 49.778 | 1.00 99.99 |
| ATOM | 1652 | N | THR | 215 | 31.771 | 23.481 | 48.162 | 1.00 99.99 |
| ATOM | 1653 | CA | THR | 215 | 32.243 | 24.351 | 47.060 | 1.00 99.99 |
| ATOM | 1654 | C | THR | 215 | 31.172 | 24.843 | 46.107 | 1.00 99.99 |
| ATOM | 1655 | O | THR | 215 | 30.056 | 24.326 | 46.061 | 1.00 99.99 |
| ATOM | 1656 | CB | THR | 215 | 33.274 | 23.602 | 46.206 | 1.00 99.99 |
| ATOM | 1657 | OG1 | THR | 215 | 32.611 | 22.531 | 45.516 | 1.00 99.99 |
| ATOM | 1658 | CG2 | THR | 215 | 34.348 | 23.000 | 47.094 | 1.00 99.99 |
| ATOM | 1659 | N | LEU | 216 | 31.581 | 25.822 | 45.285 | 1.00 99.99 |
| ATOM | 1660 | CA | LEU | 216 | 30.658 | 26.333 | 44.256 | 1.00 99.99 |
| ATOM | 1661 | C | LEU | 216 | 30.425 | 25.258 | 43.207 | 1.00 99.99 |
| ATOM | 1662 | O | LEU | 216 | 29.298 | 25.130 | 42.692 | 1.00 99.99 |
| ATOM | 1663 | CB | LEU | 216 | 31.278 | 27.623 | 43.665 | 1.00 99.99 |
| ATOM | 1664 | CG | LEU | 216 | 30.391 | 28.245 | 42.582 | 1.00 99.99 |
| ATOM | 1665 | CD1 | LEU | 216 | 29.018 | 28.680 | 43.046 | 1.00 99.99 |
| ATOM | 1666 | CD2 | LEU | 216 | 31.149 | 29.464 | 42.026 | 1.00 99.99 |
| ATOM | 1667 | N | LEU | 217 | 31.467 | 24.462 | 42.877 | 1.00 99.99 |
| ATOM | 1668 | CA | LEU | 217 | 31.282 | 23.400 | 41.907 | 1.00 99.99 |
| ATOM | 1669 | C | LEU | 217 | 30.275 | 22.375 | 42.469 | 1.00 99.99 |
| ATOM | 1670 | O | LEU | 217 | 29.426 | 21.901 | 41.700 | 1.00 99.99 |
| ATOM | 1671 | CB | LEU | 217 | 32.580 | 22.705 | 41.500 | 1.00 99.99 |
| ATOM | 1672 | CG | LEU | 217 | 32.479 | 21.855 | 40.217 | 1.00 99.99 |
| ATOM | 1673 | CD1 | LEU | 217 | 32.304 | 22.749 | 39.008 | 1.00 99.99 |
| ATOM | 1674 | CD2 | LEU | 217 | 33.717 | 20.972 | 40.130 | 1.00 99.99 |
| ATOM | 1675 | N | ASP | 218 | 30.300 | 22.097 | 43.762 | 1.00 99.99 |
| ATOM | 1676 | CA | ASP | 218 | 29.288 | 21.186 | 44.320 | 1.00 99.99 |
| ATOM | 1677 | C | ASP | 218 | 27.901 | 21.813 | 44.250 | 1.00 99.99 |
| ATOM | 1678 | O | ASP | 218 | 26.941 | 21.060 | 44.010 | 1.00 99.99 |
| ATOM | 1679 | CB | ASP | 218 | 29.613 | 20.881 | 45.778 | 1.00 99.99 |
| ATOM | 1680 | CG | ASP | 218 | 30.832 | 19.964 | 45.849 | 1.00 99.99 |
| ATOM | 1681 | OD1 | ASP | 218 | 30.779 | 18.885 | 45.200 | 1.00 99.99 |
| ATOM | 1682 | OD2 | ASP | 218 | 31.806 | 20.352 | 46.548 | 1.00 99.99 |
| ATOM | 1683 | N | ALA | 219 | 27.794 | 23.128 | 44.472 | 1.00 99.99 |
| ATOM | 1684 | CA | ALA | 219 | 26.462 | 23.767 | 44.407 | 1.00 99.99 |
| ATOM | 1685 | C | ALA | 219 | 25.920 | 23.670 | 42.975 | 1.00 99.99 |
| ATOM | 1686 | O | ALA | 219 | 24.738 | 23.386 | 42.778 | 1.00 99.99 |
| ATOM | 1687 | CB | ALA | 219 | 26.541 | 25.202 | 44.874 | 1.00 99.99 |
| ATOM | 1688 | N | LEU | 220 | 26.770 | 23.844 | 41.965 | 1.00 99.99 |
| ATOM | 1689 | CA | LEU | 220 | 26.293 | 23.714 | 40.580 | 1.00 99.99 |
| ATOM | 1690 | C | LEU | 220 | 25.938 | 22.278 | 40.257 | 1.00 99.99 |
| ATOM | 1691 | O | LEU | 220 | 24.905 | 22.025 | 39.628 | 1.00 99.99 |
| ATOM | 1692 | CB | LEU | 220 | 27.380 | 24.172 | 39.613 | 1.00 99.99 |
| ATOM | 1693 | CG | LEU | 220 | 27.497 | 25.692 | 39.660 | 1.00 99.99 |
| ATOM | 1694 | CD1 | LEU | 220 | 27.828 | 26.130 | 41.083 | 1.00 99.99 |
| ATOM | 1695 | CD2 | LEU | 220 | 28.603 | 26.147 | 38.716 | 1.00 99.99 |
| ATOM | 1696 | N | ASP | 221 | 26.698 | 21.295 | 40.747 | 1.00 99.99 |
| ATOM | 1697 | CA | ASP | 221 | 26.379 | 19.886 | 40.498 | 1.00 99.99 |
| ATOM | 1698 | C | ASP | 221 | 25.055 | 19.523 | 41.165 | 1.00 99.99 |
| ATOM | 1699 | O | ASP | 221 | 24.372 | 18.581 | 40.760 | 1.00 99.99 |
| ATOM | 1700 | CB | ASP | 221 | 27.497 | 19.003 | 41.046 | 1.00 99.99 |
| ATOM | 1701 | CG | ASP | 221 | 27.463 | 17.593 | 40.483 | 1.00 99.99 |
| ATOM | 1702 | OD1 | ASP | 221 | 27.353 | 17.484 | 39.248 | 1.00 99.99 |
| ATOM | 1703 | OD2 | ASP | 221 | 27.524 | 16.630 | 41.301 | 1.00 99.99 |
| ATOM | 1704 | N | MET | 222 | 24.705 | 20.250 | 42.223 | 1.00 99.99 |
| ATOM | 1705 | CA | MET | 222 | 23.474 | 20.015 | 42.970 | 1.00 99.99 |
| ATOM | 1706 | C | MET | 222 | 22.242 | 20.635 | 42.344 | 1.00 99.99 |
| ATOM | 1707 | O | MET | 222 | 21.108 | 20.421 | 42.828 | 1.00 99.99 |
| ATOM | 1708 | CB | MET | 222 | 23.600 | 20.598 | 44.373 | 1.00 99.99 |
| ATOM | 1709 | CG | MET | 222 | 24.645 | 19.815 | 45.159 | 1.00 99.99 |
| ATOM | 1710 | SD | MET | 222 | 24.088 | 18.111 | 45.406 | 1.00 99.99 |
| ATOM | 1711 | CE | MET | 222 | 22.741 | 18.387 | 46.536 | 1.00 99.99 |
| ATOM | 1712 | N | LEU | 223 | 22.416 | 21.405 | 41.248 | 1.00 99.99 |
| ATOM | 1713 | CA | LEU | 223 | 21.241 | 21.947 | 40.541 | 1.00 99.99 |
| ATOM | 1714 | C | LEU | 223 | 20.331 | 20.786 | 40.188 | 1.00 99.99 |
| ATOM | 1715 | O | LEU | 223 | 20.769 | 19.700 | 39.804 | 1.00 99.99 |
| ATOM | 1716 | CB | LEU | 223 | 21.686 | 22.668 | 39.273 | 1.00 99.99 |
| ATOM | 1717 | CG | LEU | 223 | 22.345 | 23.992 | 39.644 | 1.00 99.99 |
| ATOM | 1718 | CD1 | LEU | 223 | 23.539 | 23.726 | 40.554 | 1.00 99.99 |
| ATOM | 1719 | CD2 | LEU | 223 | 22.816 | 24.698 | 38.378 | 1.00 99.99 |
| ATOM | 1720 | N | GLU | 224 | 19.016 | 21.027 | 40.313 | 1.00 99.99 |
| ATOM | 1721 | CA | GLU | 224 | 18.065 | 19.951 | 40.053 | 1.00 99.99 |
| ATOM | 1722 | C | GLU | 224 | 17.797 | 19.793 | 38.574 | 1.00 99.99 |

TABLE 4-continued

| | | | | | | | | |
|---|---|---|---|---|---|---|---|---|
| ATOM | 1723 | O | GLU | 224 | 17.604 | 20.803 | 37.921 | 1.00 99.99 |
| ATOM | 1724 | CB | GLU | 224 | 16.742 | 20.249 | 40.749 | 1.00 99.99 |
| ATOM | 1725 | CG | GLU | 224 | 16.922 | 20.138 | 42.244 | 1.00 99.99 |
| ATOM | 1726 | CD | GLU | 224 | 17.076 | 18.668 | 42.631 | 1.00 99.99 |
| ATOM | 1727 | OE1 | GLU | 224 | 18.243 | 18.196 | 42.648 | 1.00 99.99 |
| ATOM | 1728 | OE2 | GLU | 224 | 16.023 | 18.031 | 42.904 | 1.00 99.99 |
| ATOM | 1729 | N | PRO | 225 | 17.779 | 18.540 | 38.162 | 1.00 99.99 |
| ATOM | 1730 | CA | PRO | 225 | 17.508 | 18.158 | 36.791 | 1.00 99.99 |
| ATOM | 1731 | C | PRO | 225 | 16.106 | 18.566 | 36.353 | 1.00 99.99 |
| ATOM | 1732 | O | PRO | 225 | 15.124 | 17.995 | 36.802 | 1.00 99.99 |
| ATOM | 1733 | CB | PRO | 225 | 17.650 | 16.685 | 36.949 | 1.00 99.99 |
| ATOM | 1734 | CG | PRO | 225 | 17.360 | 16.391 | 38.401 | 1.00 99.99 |
| ATOM | 1735 | CD | PRO | 225 | 17.667 | 17.347 | 39.189 | 1.00 99.99 |
| ATOM | 1736 | N | PRO | 226 | 16.017 | 19.531 | 35.463 | 1.00 99.99 |
| ATOM | 1737 | CA | PRO | 226 | 14.748 | 19.985 | 34.908 | 1.00 99.99 |
| ATOM | 1738 | C | PRO | 226 | 14.204 | 19.036 | 33.848 | 1.00 99.99 |
| ATOM | 1739 | O | PRO | 226 | 14.946 | 18.320 | 33.178 | 1.00 99.99 |
| ATOM | 1740 | CB | PRO | 226 | 15.126 | 21.348 | 34.336 | 1.00 99.99 |
| ATOM | 1741 | CG | PRO | 226 | 16.534 | 21.153 | 33.863 | 1.00 99.99 |
| ATOM | 1742 | CD | PRO | 226 | 17.183 | 20.226 | 34.858 | 1.00 99.99 |
| ATOM | 1743 | N | VAL | 227 | 12.895 | 18.926 | 33.699 | 1.00 99.99 |
| ATOM | 1744 | CA | VAL | 227 | 12.260 | 18.030 | 32.737 | 1.00 99.99 |
| ATOM | 1745 | C | VAL | 227 | 12.210 | 18.650 | 31.349 | 1.00 99.99 |
| ATOM | 1746 | O | VAL | 227 | 11.637 | 19.735 | 31.223 | 1.00 99.99 |
| ATOM | 1747 | CB | VAL | 227 | 10.832 | 17.724 | 33.177 | 1.00 99.99 |
| ATOM | 1748 | CG1 | VAL | 227 | 10.069 | 17.087 | 32.020 | 1.00 99.99 |
| ATOM | 1749 | CG2 | VAL | 227 | 10.858 | 16.762 | 34.359 | 1.00 99.99 |
| ATOM | 1750 | N | ARG | 228 | 12.761 | 17.982 | 30.333 | 1.00 99.99 |
| ATOM | 1751 | CA | ARG | 228 | 12.747 | 18.551 | 28.984 | 1.00 99.99 |
| ATOM | 1752 | C | ARG | 228 | 11.467 | 18.199 | 28.235 | 1.00 99.99 |
| ATOM | 1753 | O | ARG | 228 | 10.909 | 17.113 | 28.410 | 1.00 99.99 |
| ATOM | 1754 | CB | ARG | 228 | 13.962 | 18.112 | 28.178 | 1.00 99.99 |
| ATOM | 1755 | CG | ARG | 228 | 15.314 | 18.448 | 28.787 | 1.00 99.99 |
| ATOM | 1756 | CD | ARG | 228 | 15.485 | 19.921 | 29.138 | 1.00 99.99 |
| ATOM | 1757 | NE | ARG | 228 | 16.790 | 20.182 | 29.750 | 1.00 99.99 |
| ATOM | 1758 | CZ | ARG | 228 | 17.063 | 21.232 | 30.518 | 1.00 99.99 |
| ATOM | 1759 | NH1 | ARG | 228 | 16.144 | 22.153 | 30.787 | 1.00 99.99 |
| ATOM | 1760 | NH2 | ARG | 228 | 18.261 | 21.424 | 31.068 | 1.00 99.99 |
| ATOM | 1761 | N | PRO | 229 | 11.043 | 19.071 | 27.331 | 1.00 99.99 |
| ATOM | 1762 | CA | PRO | 229 | 9.797 | 18.917 | 26.608 | 1.00 99.99 |
| ATOM | 1763 | C | PRO | 229 | 9.799 | 18.007 | 25.394 | 1.00 99.99 |
| ATOM | 1764 | O | PRO | 229 | 9.104 | 18.283 | 24.420 | 1.00 99.99 |
| ATOM | 1765 | CB | PRO | 229 | 9.464 | 20.366 | 26.195 | 1.00 99.99 |
| ATOM | 1766 | CG | PRO | 229 | 10.811 | 20.968 | 25.962 | 1.00 99.99 |
| ATOM | 1767 | CD | PRO | 229 | 11.670 | 20.398 | 27.074 | 1.00 99.99 |
| ATOM | 1768 | N | VAL | 230 | 10.497 | 16.878 | 25.465 | 1.00 99.99 |
| ATOM | 1769 | CA | VAL | 230 | 10.538 | 15.919 | 24.371 | 1.00 99.99 |
| ATOM | 1770 | C | VAL | 230 | 9.175 | 15.357 | 24.000 | 1.00 99.99 |
| ATOM | 1771 | O | VAL | 230 | 8.918 | 15.050 | 22.841 | 1.00 99.99 |
| ATOM | 1772 | CB | VAL | 230 | 11.424 | 14.737 | 24.750 | 1.00 99.99 |
| ATOM | 1773 | CG1 | VAL | 230 | 11.191 | 13.592 | 23.769 | 1.00 99.99 |
| ATOM | 1774 | CG2 | VAL | 230 | 12.887 | 15.159 | 24.700 | 1.00 99.99 |

Analysis of Molecular Modeling of EF-1α

Comparison of models shows that the 3-D structures of EF-1α proteins from *S. cerevisiae*, *L. donovani*, *Mus musculu* and from *Homo sapiens* resemble each other closely. Aside from differences in irregular C-terminal loop regions, the only notable difference in the structures of the human and *leishmania* proteins is attributed to an isolated fragment corresponding to the twelve amino acid insertion in the *H. sapien's* protein sequence at position 214, that is missing from pathogen EF-1α. The structure of this fragment was identified as a hairpin motif comprised of two anti-parallel β strands each of which is four amino acids in length. *L. donovani* EF-1α has a proline residue at position 214 corresponding to point of insertion of the hairpin fold in the *H. sapien's* EF-1α. This proline likely stabilizes the backbone of the pathogen EF-1α by preserving local structural similarity. However, this proline "stitching" at the point of the deletion in the 3-D structure of the pathogen EF-1α does not compensate for a nearly 5.4Å wide gap in the pathogen structure corresponding to the distance between top edges of the hairpin.

The indel sequence (hairpin from the human form), GWKVT$^{217}$RKDGNASGT (SEQ ID NO:26) was searched against the PROSITE™ database that contains information about protein motifs with defined functions. This analysis showed that human EF-1α contains consensus phosphorylation sites (PROSITE™ matches PS00005 and PS00006) for protenin kinase C (30) and casein kinase II (31) at threonine$^{217}$ in the hairpin loop. This shows that the hairpin loop present in human EF-1α proteins and from other higher eukaryotes but missing pn pathogen EF-1α, contributes to the observed differences in protein function and subcellular distribution.

The structure of EF-1α proteins from *S. cerevisiae* reveals that the hairpin is 20Å long and is in close proximity to the main body of the human protein. The side chains of the hairpin form a complex network of hydrophobic and polar interactions involving the α-helix formed by amino acids 226-231, the β-strand formed by residues 233-236 and the low complexity region of amino acids 182-191 in the main body of the human protein. For example, Glu$^{215}$ in the hairpin reaches a proximity of 2A with the side chain of Leu$^{184}$ in the main part of the protein making possible the formation of hydrogen bonds between the residues.

The absence of the twelve residue hairpin in the structure of pathogen EF-1α provides the basis to design molecules capable of specifically binding to the indel complementarity region of the pathogen protein. This "unshielded" region of the pathogen EF-1α contains several highly polar residues such as Asp$^{218}$, Glu$^{224}$, Met$^{222}$, Lys$^{187}$ and Arg$^{189}$ with their charged side chains pointed directly toward the predicted location of the missing hairpin. The bulky amino acids, Trp$^{210}$, Phe$^{211}$, Trp$^{214}$ and Tyr$^{217}$ in the hairpin contribute to blocking an attacking reagent from reaching the corresponding structural region of the *Homo sapien's* homologue. Moieties that bind to the indel complementarity region may be used for identification or segregation of the pathogen protein or to block the area and remove the pathogenic (virulence) characteristic of the pathogen protein as is accomplished by the hairpin region in the human form.

Identification of Binding Moieties

Targeting sites on a pathogen protein may be identified by locating the regions of tight atomic packing. Once such regions are identified, sites that are "too exposed" to solvent may be filtered out. For example, sites that are on protrusions are unlikely to be good candidates as active sites.

In order to identify the cavities best suited for small molecule binding, the Analytic Connoly™ surface for the indel complementarity region on EF1-α of *L. donovani* was calculated using the MOE™ software. Connoly surfaces are identified according to local hydrophobicity. Other types of surfaces (Gauss-Connoly, Gauss accessible, interaction surface) were also computed to give more insight into properties of the indel complementarity region. The calculated surfaces show two pockets as potential binding sites. The first pocket is surrounded by residues: GLN164, TYR167, ASP168, ARG189, PHE190, ILE191, TRP210, TYR211, LYS212, GLY213, PRO214, THR215, ASP218, ALA219, MET222.

The first pocket is relatively large, C-shaped, with two distinct compartments. Both compartments have roughly similar size, very tightly packed and have deeply bured hydrophobic areas. One compartment is open ended and has additional hydrophobic areas formed by TRP210 and TYR167.

The second pocket is surrounded by residues: LYS146, GLN147, MET148, VAL149, LYS187, VAL188, ARG189, ALA199, LEU220, MET222, LEU223, GLU224. It is smaller and deeper than the first pocket; channel shaped; not very tightly packed and has less hydrophobic interior.

The "MultiFragment search" package of the MOE™ program may be used to identify small molecules capable of binding to a selected target with evaluation for energy of binding. For the smaller binding pocket (pocket 2) the top candidate binding moieties are shown in Table 5.

TABLE 5

| Name | dU | dE |
| --- | --- | --- |
| methyltetrazolium | 16.55671 | −13.1568 |
| acetaldehyde | −1.18469 | −6.79805 |
| methylsulfonate | 10.27105 | −5.99061 |
| acetate ion | 4.78712 | −2.04924 |
| 5-methylimidazole | −1.32273 | −1.38834 |

The primary field in the Table is dE—interaction energy in kcal/mol (with solvent model) calculated as E(complex)—E (receptor)—E(fragment). The negative values of dE indicate favourable interaction of the molecular fragment with the protein. As it can be seen, only very small molecular fragments could effectively fit into the smaller pocket. The best is methyltetrazolium, whose nitrogens interact with the carboxylic group GLU224 and methyl group forms a hydrophobic contact with the side chain LYS187.

The best binding moieties for the larger pocket are (in order of highest affinity to lowest): 3-methylindole, benzene, phenol, 1,2-dimethylpyrrolidine, methylguanidinium, thiazole, n,n-dimethylacetamide, 2-butene, cyclohexane, butane, n-methylacetamide, isobutane, 2-butyne, methylamidinium, propane, 5-methylimidazole, ethylthiol, acetamide, N-methylformamide, propyne, dimethylether, ethane, piperidinium, methylthiol, ethanol, methylchloride, methylsulfonamide, acetaldehyde, methane, dimethylsulfone, methanol, acetonitrile, methylammonium, trimethylammonium and trifluoromethane.

3-methylindole binds into the larger pocket with extremely high kinetics. This compound fits perfectly between ARG189, THR215, and ASP218 and appears to mimic the side chain of tryptophan 212 of the human protein. The latter amino acid is located on the indel of the human homologue and knits perfectly with the Arg, Thr, and Asp pocket of the complementarity region.

Production of Peptides and Antibody Generation

The three-dimensional model of the *leishmania* identifies the peptide sequences that are normally concealed (indel complementarity region) by the hairpin loop (indel) present on human EF-1α. Using publicly available protein structure visualization programs, short peptide sequences derived from *leishmania* EF-1α were selected for development of antibodies. Three such sequences so identified are the above-described peptides labelled SEQ ID NO:1, 2, and 3.

Peptides were synthesized at the University of British Columbia Nucleic Acid and Protein Services laboratory using a Perkin Elmer peptide synthesizer. The synthesis was started with a resin column. The amino acid bound to the resin is protected and the first step of the protocol consists of washing the column with 20% v/v solution of piperidine/N,N-dimethylformamide (DMF) in order to de-protect the C terminus residue. The next residue, an Fmoc protected L-amino acid was dissolved and delivered to the reaction vessel or column. The protocol for synthesis consisted of a number of cycles, each one performing the following operations: deprotection of previous residue with piperidine, washing the column or vessel with DMF, and attachment of the next residue. After synthesis, the peptides were cleaved from the column by the following steps: 1) resin washed with dichloromethane, 2) resin is dried, 3) TFA/Scavenger mixture of choice is added to extract the peptide from the resin, 4) supernatant removed, 5) diethyl ether added (at this point the peptide precipitates), 6) precipitate collected and peptide qualitatively analyzed then purified or freeze dried as desired.

Peptides prepared as described above were primed by first emulsifying with complete Freunds adjuvant and phosphate buffered saline (PBS) to ensure high titers of peptide specific antibodies. For each peptide, 4 mice were injected intraperitoneally with the mixture (100 μg of peptide) using a 22-gauge needle. Mice were boosted 3 weeks later with a second intraperitoneal injection containing 50 μg of peptide with incomplete Freunds adjuvant. Mice were bled 7 days following the booster injection, with a total of 200 μl of blood collected. The blood was allowed to clot, after which the serum was transferred to a clean tube. Antibody titer was determined by spectroscopy, and mice with sufficient titer were boosted with a further 50 μg of peptide intraperitoneally.

The following protocol may be followed for subsequent work in preparation of monoclonal antibodies. Three days after the booster injection mice are sacrificed, spleen cells isolated, and seeded into 96 well plates at a titer of 10,000 cells per well. Transformed myeloma cells are incubated with the mice spleen cells, and fusion promoted with a polyethylene glycol mixture and centrifugation. Fused cells are then dispersed in culture plates under conditions that select for fusion cells. Following a 4 to 6 week incubation time, the medium in the culture wells is tested for immunogenicity to the desired antigen, and positive wells are subcloned to isolate specific antibody producing hybridomas. The individual hybridomas are expanded by culture, catalogue and frozen in liquid nitrogen for stable storage. Hybridoma cell lines may be thawed and grown in culture. Culture media may be collected and the desired antibody purified from the media by precipitation, followed by column chromatography. Antibodies may be tested for specificity using independent assay systems which determine: (1) whether they bind to the pathogen derived antigen but not the host protein, (2) whether they interfere with the function of pathogen EF-1α in in vitro translation assays, (3) whether they block the interaction of pathogen EF-1α with SHP-1 in vitro, and (4) whether upon introduction into *leishmania* infected macrophages, they affect parasite viability.

Peptides having the sequence of SEQ ID NO:1 and 3 generated polyclonal sera in mice that is specific for the detection of protozoal pathogen EF-1α with absolutely no detection of the host macrophage EF-1α. In the case of SEQ ID NO:3, serum from immunized mice yielded a high titre of polyclonal antibody, that once diluted 1 in 5000 fold, was able to clearly detect the *leishmania* EF-1α-protein, and displayed no other cross reactivity from total cell lysate or mammalian EF-1α. These antibodies are particularly suitable for use in a diagnostic test for Leishmaniasis. First, peripheral blood monocytes are isolated from individuals who are suspected of suffering from Leishmaniasis by withdrawing a small amount of blood, the monocytes are subjected to a simple lysis step, and the presence of *leishmania* EF-1α is detected by standard ELISA assay.

Confocal microscopy of macrophage infected with *leishmania* and probed with EF-1α antibodies showed the *leishmania* promastigote within macrophage vacuoles. Macrophage probed with a *leishmania* specific anti-EF-1α antibody shows that *leishmania* EF-1α leaves the vaculuolar bound protozoal parasite and is found within the macrophage cytoplasm. Macrophages not infected and probed with the *leishmania* specific anti-EF-1α shows no cross-reactivity. Immunofluorescence results from a species non-specific anti-EF-1α indicates the distribution of macrophage EF-1α throughout the macrophage cytoplasm. This shows that the *leishmania* specific anti-EF-1α antibody serves to diagnose humans infected with *leishmania.*

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the invention as described and claimed herein. All patents, patent applications and publications referred to herein are hereby incorporated by reference.

REFERENCES

1. Reiner, N. E. (1994) *Immunol. Today* 15, 374-381.
2. Nandan, D., Knutson, K. L., Lo, R., and Reiner, N. E. (2000) *J Leukocyte Biology* 67, 464-470.
3. Nandan, D. and Reiner, N. E. (1995) *Infect. Immun.* 63, 4495-4500.
4. Nandan, D., Lo, R., and Reiner, N. E. (1999) *Infection and Immunity* 67, 4055-4063.
5. Olivier, M., Romero-Gallo, B. J., Matte, C., Blanchette, J., Posner, B. I., Tremblay, M. J., and Faure, R. (1998) *J. Biol. Chem.* 273, 13944-13949.
6. Blanchette, J., Racette, N., Faure, R., Siminovitch, K. A., and Olivier, M. (1999) *Eur. J. Immunol.* 29, 3737-3744.
7. Forget, G., Siminovitch, K. A., Rivest, S., and Olivier, M., *Journal of Leukocyte Biology Supplement* 1999, 31. 1999. Ref Type: Abstract
8. Pathak, M. K. and Yi, T. (2001) *J Immunol.* 167, 3391-3397.
9. Jiao, H., Berrada, K., Yang, W., Tabrizi, M., Platanias, L. C., and Yi, T. (1996) *Mol. Cell. Biol.* 16, 6985-6992.
10. Reiner, N. E. (1982) *Infect. Immun.* 38, 1223-1230.
11. Guex, N. and Peitsch, M. C. (1997) *Electrophoresis* 18, 2714-2723.
12. Berg, K. L., Carlberg, K., Rohrschneider, L. R., Siminovitch, K. A., and Stanley, E. R. (1998) *Oncogene* 17, 2535-2541.
13. Frearson, J. A. and Alexander, D. R. (1997) *BioEssays* 19, 417-427.
14. Blery, M., Olcese, L., and Vivier, E. (2000) *Hum. Immunol.* 61, 51-64.
15. Condeelis, J. (1995) *Trends Biochem. Sci.* 20, 169-170.
16. Kaur, K. J. and Ruben, L. (1994) *J. Biol. Chem.* 269, 23045-23050.
17. Murray, J. W., Edmonds, B. T., Liu, G., and Condeelis, J. (1996) *J. Cell Biol.* 135, 1309-1321.
18. Ganatra, J. B., Chandler, D., Santos, C., Kuppermann, B., and Margolis, T. P. (2000) *Am. J Ophthalmol.* 129, 166-172.
19. Andersen, G. R., Valente, L., Pedersen, L., Kinzy, T. G., and Nyborg, J. (2001) *Nat. Struct. Biol.* 8, 531-534.
20. Siegal, G., Davis, B., Kristensen, S. M., Sankar, A., Linacre, J., Stein, R. C., Panayotou, G., Waterfield, M. D., and Driscoll, P. C. (1998) *J. Mol. Biol.* 276, 461-478.
21. Pathak, M. K. and Yi, T. (2001) *J Immunol.* 167, 3391-3397.
22. Billaut-Mulot, O., Fernandez-Gomez, R., Loyens, M., and Ouaissi, A. (1996) *Gene* 174, 19-26.
23. Songyang, Z., Shoelson, S. E., Chaudhuri, M., Gish, G., Pawson, T., Haser, W. G., King, F., Roberts, T., Ratnofsky, S., and Lechleider, R. J. (1993) *Cell* 72, 767-778.
24. Fantl, W. J., Escobedo, J. A., Martin, G. A., Turck, C. W., Del Rosario, M., McCormick, F., and Williams, L. T. (1992) *Cell* 69, 413-423.
25. Damen, J. E., Cutler, R. L., Jiao, H., Yi, T., and Krystal, G. (1995) *J. Biol. Chem.* 270, 23402-23408.
26. Stein, R. C. and Waterfield, M. D. (2000) *Mol. Med. Today* 6, 347-357.
27. Hoedemaeker, F. J., Siegal, G., Roe, S. M., Driscoll, P. C., and Abrahams, J. P. (1999) *J Mol. Biol.* 292, 763-770.
28. Yohannan, J., Wienands, J., Coggeshall, K. M., and Justement, L. B. (1999) *J Biol. Chem.* 274, 18769-18776.
29. Vanhaesebroeck, B., Jones, G. E., Allen, W. E., Zicha, D., Hooshmand-Rad, R., Sawyer, C., Wells, C., Waterfield, M. D., and Ridley, A. J. (1999) *Nat. Cell Biol.* 1, 69-71.

30. Kishimoto, A., Nishiyama, K., Nakanishi, H., Uratsuji, Y., Nomura, H., Takeyama, Y., and Nishizuka, Y. (1985) *J Biol. Chem.* 260, 12492-12499.
31. Pinna, L. A. (1990) *Biochim. Biophys. Acta* 1054, 267-284.
32. Sakamoto, K. M., et al., *Proceedings of the National Academy of Sciences of the United States of America*, 2001. 98(15): p. 8554-9.
33. Tellam, J., et al., *Journal of Biological Chemistry*, 2001. 276(36): p. 33353-60.
34. Joshi, P. B., et al., *Gene*, 1995. 156(1): p. 145-9.
35. Laban, A. and D. F. Wirth, *Proceedings of the National Academy of Sciences of the United States of America*, 1989. 86(23): p. 9119-23.
36. LeBowitz, J. H., et al., *Proceedings of the National Academy of Sciences of the United States of America*, 1990. 87(24): p. 9736-40.
37. Kelly, J. M., et al., *Nucleic Acids Research*, 1992. 20(15): p. 3963-9.
38. Ooms, F., *Current Medicinal Chemistry*, 2000. 7(2): p. 141-58.
39. Kurogi, Y. and O. F. Guner, *Current Medicinal Chemistry*, 2001. 8(9): p. 1035-55.
40. Gradler, U., et al., *Journal of Molecular Biology*, 2001. 306(3): p. 455-67.
41. Aronov, A. M., et al., *Biochemistry*, 2000. 39(16): p. 4684-91.
42. Button, L. L., et al., *Gene*, 1993. 134(1): p. 75-81.

We claim:

1. A method for testing a compound for specific binding to a pathogen protein, comprising:
    a) selecting a protein conserved between a pathogen and a host to the pathogen
    b) identifying an indel in the conserved protein, wherein the pathogen protein has an indel not present in the host protein and
    c) contacting a compound to be tested with each of the pathogen protein and the host protein to compare binding; wherein binding of the compound to the pathogen protein and the absence or reduced binding of the compound to the host protein is indicative of the compound being capable of said specific binding to the pathogen protein.

2. The method of claim 1, wherein the pathogen protein and the host protein of the pair have 70% sequence identity or more.

3. The method of claim 1, wherein the host protein and the pathogen protein are proteins for which absence thereof affects viability of both host and pathogen respectively.

4. The method of claim 1, wherein the pathogen is selected from virus, bacteria, fungi and protozoa.

5. The method of claim 1, wherein the host is an animal.

6. The method of claim 5, wherein the host is a mammal.

7. The method of claim 4, wherein the host is human.

8. The method of claim 1, wherein the indel is 6 consecutive amino acids.

9. The method of claim 8, wherein the indel is 10 consecutive amino acids.

10. The method of claim 8, wherein the indel is 15 consecutive amino acids.

11. The method of claim 8, wherein the indel is 20 consecutive amino acids.

12. The method of claim 8, wherein the indel is 25 consecutive amino acids.

13. The method of claim 1, wherein the compound being capable of said specific binding exhibits no detectable binding to the host protein.

14. The method of claim 1, wherein the compound is an antibody or antibody fragment.

15. The method of claim 1, further comprising joining the provided compound to a moiety for use as a diagnostic or therapeutic agent specific for the pathogen form.

16. The method of claim 15, wherein the moiety is a ligand or a label.

17. The method of claim 15, wherein the moiety antagonizes a function of the pathogen form.

18. The method of claim 1, wherein the host protein is EF1-α.

19. The method of claim 1, wherein the host is a plant.

20. The method of claim 1, wherein the indel is 4 consecutive amino acids.

21. The method of claim 1, wherein the compound being capable of said specific binding exhibits disruption of pathogen protein function.

* * * * *

UNITED STATES PATENT AND TRADEMARK OFFICE
CERTIFICATE OF CORRECTION

PATENT NO. : 7,572,589 B2  Page 1 of 1
APPLICATION NO. : 10/494175
DATED : August 11, 2009
INVENTOR(S) : Reiner et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (305) days Delete the phrase "by 305 days" and insert -- by 721 days --

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,572,589 B2  Page 1 of 1
APPLICATION NO. : 10/494175
DATED : August 11, 2009
INVENTOR(S) : Reiner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1099 days.

Signed and Sealed this

Seventh Day of September, 2010

David J. Kappos
*Director of the United States Patent and Trademark Office*